(12) United States Patent
Geng et al.

(10) Patent No.: US 8,202,523 B2
(45) Date of Patent: Jun. 19, 2012

(54) GLYCOSYLATED POLYPEPTIDES PRODUCED IN YEAST MUTANTS AND METHODS OF USE THEREOF

(75) Inventors: Yu Geng, San Diego, CA (US); Robert James Luallen, San Diego, CA (US)

(73) Assignee: ProSci, Inc., Poway, CA (US)

( * ) Notice: Subject to any disclaimer, the term of this patent is extended or adjusted under 35 U.S.C. 154(b) by 1157 days.

(21) Appl. No.: 11/525,673

(22) Filed: Sep. 22, 2006

(65) Prior Publication Data

US 2008/0038286 A1 Feb. 14, 2008

Related U.S. Application Data

(60) Provisional application No. 60/719,952, filed on Sep. 22, 2005.

(51) Int. Cl.
| | |
|---|---|
| A01N 63/00 | (2006.01) |
| A01N 63/04 | (2006.01) |
| A61K 39/00 | (2006.01) |
| A61K 39/38 | (2006.01) |
| A61K 45/00 | (2006.01) |
| A61K 47/00 | (2006.01) |

(52) U.S. Cl. ............... 424/279.1; 424/184.1; 424/278.1; 424/282.1; 424/93.51

(58) Field of Classification Search .......................... None
See application file for complete search history.

(56) References Cited

U.S. PATENT DOCUMENTS

| | | | |
|---|---|---|---|
| 4,235,877 A | 11/1980 | Fullerton | |
| 4,372,945 A | 2/1983 | Likhite | |
| 4,474,757 A | 10/1984 | Arnon et al. | |
| 4,803,070 A | 2/1989 | Cantrell et al. | |
| 4,894,229 A | 1/1990 | Polson et al. | |
| 5,139,936 A | 8/1992 | Botstein et al. | |
| 5,245,015 A | 9/1993 | Fung et al. | |
| 5,266,478 A | 11/1993 | Chang et al. | |
| 5,298,419 A | 3/1994 | Masuho et al. | |
| 5,445,960 A | 8/1995 | Masuho et al. | |
| 5,559,010 A * | 9/1996 | Klionsky et al. ............. 435/69.1 | |
| 5,585,089 A | 12/1996 | Queen et al. | |
| 5,614,612 A | 3/1997 | Haigwood et al. | |
| 5,653,985 A | 8/1997 | Haigwood et al. | |
| 5,679,355 A | 10/1997 | Alexander et al. | |
| 5,693,761 A | 12/1997 | Queen et al. | |
| 5,696,238 A | 12/1997 | Haigwood et al. | |
| 5,705,616 A | 1/1998 | Lehle et al. | |
| 5,712,373 A | 1/1998 | Eda et al. | |
| 5,750,332 A | 5/1998 | Robey et al. | |
| 5,763,160 A | 6/1998 | Wang | |
| 5,795,737 A | 8/1998 | Seed et al. | |
| 5,798,226 A | 8/1998 | Lehle et al. | |
| 5,798,251 A | 8/1998 | Robinson | |
| 5,814,321 A | 9/1998 | Miyahara et al. | |
| 5,827,723 A | 10/1998 | Matsushita | |
| 5,840,313 A | 11/1998 | Vahlne et al. | |
| 5,852,186 A | 12/1998 | Sodroski et al. | |
| 5,854,031 A | 12/1998 | Jigami et al. | |
| 5,854,400 A | 12/1998 | Chang et al. | |
| 5,863,542 A | 1/1999 | Paoletti et al. | |
| 5,914,109 A | 6/1999 | Zolla-Pazner et al. | |
| 5,919,651 A | 7/1999 | Hitzeman et al. | |
| 5,922,325 A | 7/1999 | Tilley et al. | |
| 6,030,772 A | 2/2000 | Devico et al. | |
| 6,090,392 A | 7/2000 | Berman | |
| 6,103,238 A | 8/2000 | Essex et al. | |
| 6,114,143 A | 9/2000 | Eda et al. | |
| 6,156,541 A | 12/2000 | Paul et al. | |
| 6,190,871 B1 | 2/2001 | Ho et al. | |
| 6,350,861 B1 | 2/2002 | Co et al. | |
| 6,391,567 B1 | 5/2002 | Littman et al. | |
| 6,491,919 B2 | 12/2002 | Crane | |
| 6,596,278 B2 | 7/2003 | Gander et al. | |
| 6,630,144 B1 | 10/2003 | Hart et al. | |
| 6,632,976 B1 | 10/2003 | Tomizuka et al. | |
| 6,713,069 B1 | 3/2004 | Gallaher | |
| 6,737,056 B1 | 5/2004 | Presta | |
| 6,797,276 B1 | 9/2004 | Glenn et al. | |
| 6,803,225 B2 | 10/2004 | Contreras et al. | |
| 6,815,201 B2 | 11/2004 | Pinter | |
| 7,029,872 B2 | 4/2006 | Gerngross | |
| 7,252,933 B2 * | 8/2007 | Contreras et al. ................ 435/6 |
| 7,259,007 B2 * | 8/2007 | Bobrowicz et al. ........ 435/255.5 |
| 7,332,299 B2 * | 2/2008 | Hamilton ..................... 435/69.1 |
| 7,488,591 B2 * | 2/2009 | Miura et al. .................... 435/72 |
| 7,556,806 B2 * | 7/2009 | Wang .......................... 424/184.1 |
| 7,579,166 B2 * | 8/2009 | Chiba et al. .................. 435/69.1 |
| 7,598,055 B2 * | 10/2009 | Bobrowicz et al. .......... 435/69.1 |
| 7,728,106 B2 * | 6/2010 | Wang .......................... 530/324 |
| 7,807,405 B2 * | 10/2010 | Wang .......................... 435/68.1 |

(Continued)

FOREIGN PATENT DOCUMENTS

| | | | |
|---|---|---|---|
| JP | 2001/161376 A | * | 6/2001 |
| WO | WO-90/07861 A1 | | 7/1990 |
| WO | WO 01/14522 A1 | * | 3/2001 |
| WO | WO-02/15927 A1 | | 2/2002 |
| WO | WO-2004/003194 A2 | | 1/2004 |
| WO | WO-2004/003194 A3 | | 1/2004 |
| WO | WO-2004/033663 A2 | | 4/2004 |
| WO | WO-2004/033663 A3 | | 4/2004 |
| WO | WO-2006/099592 A2 | | 9/2006 |
| WO | WO-2006/099592 A3 | | 9/2006 |
| WO | WO 2007/035930 A2 | * | 3/2007 |
| WO | WO 2008/120107 A2 | * | 10/2008 |

OTHER PUBLICATIONS

Liu et al, J. Biotechnology, Aug. 20, 2009, 143/2:95-102.*
Abe et al, Glycobiology, 2009, 19/4:428-436.*
Wang et al, Sheng wu gong xue bao (Chinese journal of biotechnology), Sep. 2007, 23/5:907-914 (abstract only).*
Song et al, Applied and Environmental Microbiology, Jul. 2007, 73/14:4446-4454.*

(Continued)

*Primary Examiner* — Nita M Minnifield
(74) *Attorney, Agent, or Firm* — Morrison & Foerster LLP

(57) ABSTRACT

The invention provides various high mannose glycosylated polypeptides that are useful in a vaccine formulations. The invention also provides methods for making such glycosylated polypeptides and its uses in eliciting HIV-neutralizing antibodies.

18 Claims, 28 Drawing Sheets

U.S. PATENT DOCUMENTS

| | | | |
|---|---|---|---|
| 7,872,111 B2* | 1/2011 | Miura et al. | 536/23.2 |
| 2003/0096221 A1 | 5/2003 | Littman et al. | |
| 2004/0018588 A1 | 1/2004 | Contreras et al. | |
| 2004/0096823 A1 | 5/2004 | Greene et al. | |
| 2004/0132101 A1 | 7/2004 | Lazar et al. | |
| 2004/0228869 A1 | 11/2004 | Olson et al. | |
| 2004/0259785 A1 | 12/2004 | Combadiere et al. | |
| 2005/0064390 A1 | 3/2005 | Berger et al. | |
| 2005/0064539 A1* | 3/2005 | Chiba et al. | 435/68.1 |
| 2005/0106664 A1* | 5/2005 | Contreras et al. | 435/69.1 |
| 2005/0244424 A1 | 11/2005 | Wang | |
| 2006/0104975 A1 | 5/2006 | Geijtenbeek et al. | |
| 2006/0134100 A1 | 6/2006 | Amara et al. | |
| 2006/0148035 A1 | 7/2006 | Gerngross | |
| 2006/0148039 A1* | 7/2006 | Kobayashi et al. | 435/85 |
| 2006/0229432 A1* | 10/2006 | Danishefsky et al. | 530/300 |
| 2008/0038286 A1* | 2/2008 | Geng et al. | 424/188.1 |
| 2011/0070607 A1* | 3/2011 | Wang | 435/68.1 |

OTHER PUBLICATIONS

Luallen et al, J. Virology, Jul. 2008, 82/13:6447-6457.*
Luallen et al, J. Virology, May 2009, 83/10:4861-4870.*
Byrd et al, J Biological Chemistry, Dec. 25, 1982, 257/24:14657-14666.*
Wei et al, PNAS, Jul. 31, 2007, 104/31:12825-12830.*
Burgess et al, JCB, 1990, 111:2129-2138.*
Lazar et al, Molecular and Cellular Biology, 1988, 8:1247-1252.*
Creighton et al, In: Proteins: Structures and Molecular Properties, 1984, pp. 314-315.*
Greenspan et al, Nature Biotechnology, 1999, 17:936-937.*
Blythe et al, Proetin Science, 2005, 14:246-248.*
Houghten et al, Vaccine 86, 1986, pp. 21-25.*
Bixler et al, Synthetic Vaccines, 1987, 1:39-71.*
Bowie et al, Science, 1990, 247:1306-1310.*
Kumar et al, PNAS, 1991, 87:1337-1341.*
Creighton et al, In: Protein Structure: A Practical Approach, 1989, pp. 184-186.*
Nosoh et al, In: Protein Stability and Stabilization through Protein Engineering, 1991, chapter 7.*
International Search Report mailed on Sep. 25, 2007, for PCT Patent Application No. PCT/US 06/37302 filed on Sep. 22, 2006, 3 pages.
5. Supplementary European Search Report mailed Nov. 14, 2008, for EP Patent Application No. 06815367.5 filed Sep. 22, 2006, three pages.
Ada, G. et al. (2003). "Carbohydrate-Protein Conjugate Vaccines," *Clin. Microbiol. Infect.* 9(2):79-85.
Baca, A.M. et al. (2000). "Overcoming Codon Bias: A Method for High-Level Overexpression of *Plasmodium* and Other AT-Rich Parasite Genes in *Escherichia coli*," *Int. J. Parasitol.* 30:113-118.
Ballou, C.E. (Mar. 10, 1970). "A Study of the Immunochemistry of Three Yeast Mannans," *J. Biol. Chem.* 245(5):1197-1203.
Baribaud, F. (2001). "The Role of DC-SIGN and DC-SIGNR in HIV and SIV Attachment, Infection, and Transmission," *Virology* 286(1):1-6.
Barr, P.J. et al. (Jun. 1987). "Antigenicity and Immunogenicity of Domains of the Human Immunodeficiency Virus (HIV) Envelope Polypeptide Expressed in the Yeast *Saccharomyces cerevisiae*," *Vaccine* 5(2):90-101.
Bashirova, A.A. et al. (Mar. 19, 2001). "A Dendritic Cell-Specific Intercellular Adhesion Molecule 3-Grabbing Nonintegrin (DC-SIGN)-Related Protein is Highly Expressed on Human Liver Sinusoidal Endothelial Cells and Promotes HIV-1 Infection," *J. Exp. Med.* 193(6):671-678.
Berland, R. et al. (2002). "Origins and Functions of B-1 Cells with Notes on the Role of CD5," *Annu. Rev. Immunol.* 20:253-300.
Bewley, C.A. (May 2, 2001). "The Potent Anti-HIV Protein Cyanovirin-N Contains Two Novel Carbohydrate Binding Sites That Selectively Bind to $Man_8$ D1D3 and $Man_9$ with Nanomolar Affinity: Implications for Binding to the HIV Envelope Protein gp120," *J. Am. Chem. Soc.* 123(17):3892-3902.

Binley, J.M. et al. (Dec. 2004). "Comprehensive Cross-Clade Neutralization Analysis of a Panel of Anti-Human Immunodeficiency Virus Type 1 Monoclonal Antibodies," *J. Virol.* 78(23):13232-13252.
Bossart, K.N. et al. (2004). "Viral Glycoprotein-Mediated Cell Fusion Assays Using *Vaccinia virus* Vectors" Chapter 21 *In Methods in Molecular Biology*, Isaacs, S.N. ed., Humana Press Inc.: Totowa, NJ, 269:309-332.
Botos, I. et al. (Sep. 13, 2002). "Structures of the Complexes of a Potent Anti-HIV Protein Cyanovirin-N and High Mannose Oligosaccharides," *J. Biol. Chem.* 277(37):34336-34342.
Botos, I. et al. (2005). "Proteins That Bind High-Mannose Sugars of the HIV Envelope," *Prog. Biophys. Mol. Biol.* 88(2):233-282.
Boyd, M.R. et al. (Jul. 1997). "Discovery of Cyanovirin-N, a Novel Human Immunodeficiency Virus-Inactivating Protein that Binds Viral Surface Envelope Glycoprotein gp120: Potential Applications to Microbicide Development," *Antimicrob. Agents Chemother.* 41(7):1521-1530.
Brooks, S.A. et al. (2002). "N-Linked Glycoproteins" Chapter 4 *In Functional and Molecular Glycobiology*, BIOS Scientific Publishers Limited: Oxford, England, pp. 73-88.
Burton, D.R. et al. (Mar. 2004). "HIV Vaccine Design and the Neutralizing Antibody Problem," *Nat. Immunol.* 5(3):233-236.
Burton, D.R. et al. (Oct. 18, 2005). "Antibody vs. HIV in a Clash of Evolutionary Titans," *Proc. Natl. Acad. Sci. USA* 102(42):14943-14948.
Calarese, D.A. et al. (Jun. 27, 2003). "Antibody Domain Exchange Is an Immunological Solution to Carbohydrate Cluster Recognition," *Science* 300:2065-2071.
Calarese, D.A. et al. (Sep. 20, 2005). "Dissection of the Carbohydrate Specificity of the Broadly Neutralizing Anti-HIV-1 Antibody 2G12," *Proc. Natl. Acad. Sci USA.* 102(38):13372-13377.
Camirand, A. et al. (Aug. 15, 1991). "Glycoprotein Biosynthesis in *Saccharomyces cerevisiae*. Isolation and Characterization of the Gene Encoding a Specific Processing α-Mannosidase," *J. Biol. Chem.* 266(23):15120-15127.
Caro, L.H.P. et al. (Dec. 1997). "In silicio Identification of Glycosyl-Phosphatidylinositol-Anchored Plasma-Membrane and Cell Wall Proteins of *Saccharomyces cerevisiae*," *Yeast* 13(15):1477-1489.
Caruthers, M.H. (1980). "New Chemical Methods for Synthesizing Polynucleotides," *Nucleic Acids Res. Symp. Ser.* 7:215-223.
Chen, B. et al. (Feb. 24, 2005). "Structure of an Unliganded Simian Immunodeficiency Virus gp120 Core," *Nature* 433:834-841.
Chiba, Y. et al. (Oct. 9, 1998). "Production of Human Compatible High Mannose-Type ($Man_5GlcNAc_2$) Sugar Chains in *Saccharomyces cerevisiae*," *J. Biol. Chem.* 273(41):26298-26304.
Chin, L.-T. et al. (1994). "Site-Directed Primary in vitro Immunization: Production of HIV-1 Neutralizing Human Monoclonal Antibodies from Lymphocytes Obtained from Seronegative Donors," *Immunology* 81(3):428-438.
Chin, L-T. et al. (1995). "Mimicking the Humoral Immune Response in vitro Results in Antigen-Specific Isotype Switching Supported by Specific Autologous T Helper Cells: Generation of Human HIV-1-Neutralizing IgG Monoclonal Antibodies from Naïve Donors," *Eur. J. Immunol.* 25(3):657-663.
Choi, B-K. et al. (Apr. 29, 2003). "Use of Combinatorial Genetic Libraries to Humanize N-linked Glycosylation in the Yeast *Pichia pastoris*," 100(9):5022-5027.
Chong, P. et al. (Dec. 1997). "A Strategy for Rational Design of Fully Synthetic Glycopeptide Conjugate Vaccines," *Infect. Immun.* 65(12):4918-4925.
Cruz, L.J. et al. (2000). "Immunogenicity Comparison of a Multi-Antigenic Peptide Bearing V3 Sequences of the Human Immunodeficiency Virus Type 1 With TAB9 Protein in Mice," *J. Pept. Sci.* 6(5):217-224.
Curtis, B.M. et al. (Sep. 1992). "Sequence and Expression of a Membrane-Associated C-type Lectin that Exhibits CD4-Independent Binding of Human Immunodeficiency Virus Envelope Glycoprotein gp120," *Proc. Natl. Acad. Sci. USA* 89:8356-8360.
Cutalo, J.M. et al. (Nov. 2004). "Characterization of Glycopeptides from $HIV-1_{SF2}$ gp120 by Liquid Chromatography Mass Spectrometry," *J. Am. Soc. Mass. Spectrom.* 15(11):1545-1555.
Dacheux, L. et al. (Nov. 2004). "Evolutionary Dynamics of the Glycan Shield of the Human Immunodeficiency Virus Envelope during Natural Infection and Implications for Exposure of the 2G12 Epitope," *J. Virol.* 78(22):12625-12637.

Davis, C.W. (Feb. 2006). "West Nile Virus Discriminates Between DC-SIGN and DC-SIGNR for Cellular Attachment and Infection," *J. Virol.* 80(3):1290-1301.

De Groot, P.W.J. et al. (Jul. 15, 2003). "Genome-Wide Identification of Fungal GPI Proteins," *Yeast.* 20(9):781-796.

Dean, N. (Jan. 6, 1999). "Asparagine-Linked Glycosylation in the Yeast Golgi.," *Biochem. Biophys. Acta.* 1426(2):309-322.

Decroix, N. et al. (2001). "Induction in Mucosa of IgG and IgA Antibodies Against Parenterally Administered Soluble Immunogens," *Scand. J. Immunol.* 53(4):401-409.

Demotz, S. et al. (Jan. 15, 1989). "Delineation of Several DR-Restricted Tetanus Toxin T Cell Epitopes," *J. Immunol.* 142(2):394-402.

Deng, Y. et al. (Jun. 1988). "Animal Cell Lysosomes Rapidly Exchange Membrane Proteins," *Proc. Natl. Acad. Sci. USA* 85(11):3860-3864.

Destruelle, M. (Apr. 1994). "Identification and Characterization of a Novel Yeast Gene: The *YGP1* Gene Product Is a Highly Glycosylated Secreted Protein That Is Synthesized in Response to Nutrient Limitation," *Mol. Cell. Biol.* 14(4):2740-2754.

Dey, B. et al. (May 2000). "Multiple Antiviral Activities of Cyanovirin-N: Blocking of Human Immunodeficiency Virus Type 1 gp120 Interaction with CD4 and Coreceptor and Inhibition of Diverse Enveloped Viruses," *J. Virol.* 74(10):4562-4569.

Diethelm-Okita, B.M. et al. (Feb. 1997). "Epitope Repertoire of Human $CD4^+$ T Cells on Tetanus Toxin: Identification of Immunodominant Sequence Segments," *J. Infect. Dis.* 175(2):382-391.

Douek, D.C. et al. (Feb. 24, 2006). "The Rational Design of an AIDS Vaccine,"*Cell* 124:677-681.

Dudkin, V.Y. et al. (Aug. 11, 2004). "Toward Fully Synthetic Carbohydrate-Based HIV Antigen Design: On the Critical Role of Bivalency." *J. Am. Hem. Soc.* 126(31): 9560-9562.

Esser, M.T. et al. (May 1999). "Cyanovirin-N Binds to gp120 to Interfere with CD4-Dependent Human Immunodeficiency Virus Type 1 Virion Binding, Fusion, and Infectivity but Does Not Affect the CD4 Binding Site on gp120 or Soluble CD4-Induced Conformational Changes in gp120," *J. Virol.* 73(5):4360-4371.

Feinberg, H. et al. (Dec. 7, 2001). "Structural Basis for Selective Recognition of Oligosaccharides by DC-SIGN and DC-SIGNR," *Science* 294:2163-2166.

Feng, L. et al. (2000). "High-Level Expression and Mutagenesis of Recombinant Human Phosphatidylcholine Transfer Protein Using a Synthetic Gene: Evidence for a C-Terminal Membrane Binding Domain," *Biochemistry* 39(50):15399-15409.

Fishwild, D.M. et al. (Jul. 1996). "High-Avidity Human IgGκ Monoclonal Antibodies From a Novel Strain of Minilocus Transgenic Mice," *Nat. Biotech.* 14:845-851.

Fukuda, M. (2000). "Cell Surface Carbohydrates: Cell Type-Specific Expression" Chapter 1 *In Molecular and Cellular Glycobiology*, Fukuda, M. et al. eds., Oxford University Press: New.York, NY, pp. 1-61.

Funatsu, O. et al. (2001). "Structural Study of N-Linked Oligosaccharides of Human Intercellular Adhesion Molecule-3 (CD50)," *Eur. J. Biochem.* 268(4):1020-1029.

Gandhi, M.J. et al. (1999). "Properties of Cyanovirin-N (CV-N): Inactivation of HIV-1 by Sessile Cyanovirin-N (sCV-N)," *Advances in Transfusion Safety*, Dev. Biol. 102:141-148.

Garber, D.A. et al. (Jul. 2004). "Prospects for an AIDS Vaccine: Three Big Questions, No Easy Answers," *Lancet Infect. Dis.* 4(7):397-413.

Gaschen, B. et al. (Jun. 28, 2002). "Diversity Considerations in HIV-1 Vaccine Selection," *Science* 296:2354-2360.

Geijtenbeek, T.B.H. et al. (Mar. 3, 2000). "DC-SIGN, a Dendritic Cell-Specific HIV-1-Binding Protein that Enhances *Trans*-Infection of T Cells," *Cell* 100:587-597.

Gemmill, T.R. et al. (1999). "Overview of *N*- and *O*-Linked Oligosaccharide Structures Found in Various Yeast Species," *Biochim. Biophys. Acta.* 1426(2):227-237.

Geng, X. et al. (May 3, 2004). "In Pursuit of Carbohydrate-Based HIV Vaccines, Part 2: The Total Synthesis of High-Mannose-Type gp120 Fragments—Evaluation of Strategies Directed to Maximal Convergence," *Angew. Chem. Int. Ed.* 43(19):2562-2565.

Giaever, G. et al. (Jul. 25, 2002). "Functional Profiling of the *Saccaromyces cerevisiae* Genome," *Nature* 418:387-391.

Gurgo, C. et al. (1988). "Envelope Sequences of Two new United Statues HIV-1 Isolates," *Virol.* 164:531-536.

Hale, R.S. et al. (Mar. 1998). "Codon Optimization of the Gene Encoding a Domain from Human Type 1 Neurofibromin Protein Results in a Threefold Improvement in Expression Level in *Escherichia coli*," *Protein Expr. Purif.* 12(2):185-188.

Hamada, K. et al. (Jul. 1999). "Amino Acid Residues in the ω-Minus Region Participate in Cellular Localization of Yeast Glycosylphosphatidylinositol-Attached Proteins," *J. Bacteriol.* 181(13):3886-3889.

Hamilton, S.R. et al. (Aug. 29, 2003). "Production of Complex Human Glycoproteins in Yeast," *Science* 301:1244-1246.

Harmsen, M.M. et al. (1993). "Effect of a *pmr1* Disruption and Different Signal Sequences on the Intracellular Processing and Secretion of *Cyamopsis tetragonoloba* α-galactosidase by *Saccharomyces cerevisiae*," *Gene* 125(2):115-123.

Herscovics, A. (1999). "Processing Glycosidases of *Saccharomyces cerevisiae*," *Biochim. Biophys. Acta.* 1426:275-285.

Herscovics, A. (Dec. 6, 1999). "Importance of Glycosidases in Mammalian Glycoprotein Biosynthesis." *Biochim. Biophys. Acta.* 1473(1):96-107.

Hindsgaul, O. (1999). "Protein-Glycan Interactions" Chapter 4 *In Essentials of Glycobiology*, Varki, A.et al. eds., Cold Spring Harbor Laboratory Press: New York, pp. 41-56.

Hitzeman, R.A. et al. (1990). "Use of Heterologous and Homologous Signal Sequences for Secretion of Heterologous Proteins from Yeast" Chapter 35 *In Methods In Enzymology*, Goeddel, D.V. ed., Academic Press, Inc.: New York, NY, 185:421-440.

Hoogenboom, H.R. (Feb. 1997). "Designing and Optimizing Library Selection Strategies for Generating High-Affinity Antibodies," *Trends Biotechnol.* 15:62-70.

Horn, T. et al. (May 1980). "Synthesis of Oligonucleotides on Cellulose. Part II: Design and Synthetic Strategy to the Synthesis of 22 Oligodeoxynucleotides Coding for Gastric Inhibitory Polypeptide (GIP)," *Nucliec Acids Res. Symp. Ser.* 7:225-232.

Humphreys, D.P. (Nov. 2000). "High-Level Periplasmic Expression in *Escherichia coli* Using a Eukaryotic Signal Peptide: Importance of Codon Usage at the 5' End of the Coding Sequence," *Protein Expr. Purif.* 20(2):252-264.

Ji, X. et al. (2005). "Mannose Binding Lectin (MBL) and HIV," *Mol. Immunol.* 42(2):145-152.

Jigami, Y. et al. (1999). "Mannosylphosphate Transfer to Yeast Mannan," *Biochim. Biophys. Acta.* 1426(2):335-345.

Julenius, K. et al. (2005). "Prediction, Conservation Analysis, and Structural Characterization of Mammalian Mucin-type O-glycosylation Sites," *Glycobiology* 15(2):153-164.

Jung, U.S. et al. (1999). "Genome-wide Analysis of Gene Expression Regulated by the Yeast Cell Wall Integrity Signalling Pathway," *Mol. Microbiol.* 34(5)1049-1057.

Katz, B. (1997). "Structural and Mechanistic Determinants of Affinity and Specificity of Ligands Discovered or Engineered by Phage Display," *Annu. Rev. Biophys. Biomol. Struct.* 26:27-45.

Kilby, J.M. et al. (1999). "Natural History of HIV-1 Disease" *In Textbook of AIDS Medicine*, Second Edition, Merrigan, et al., eds., Williams & Wilkins, pp. 49-58.

Kumar, A. et al. (Mar. 1, 1992). "'Universal' T Helper Cell Determinants Enhance Immunogenicity of a *Plasmodium falciparum* Merozoite Surface Antigen Peptide," *J. Immunol* 148(5):1499-1505.

Kwong, P.D. et al. (Dec. 12, 2002). "HIV-1 Evades Antibody-Mediated Neutralization Through Conformational Masking of Receptor-Binding Sites," *Nature* 420:678-682.

Lagorce, A. et al. (May 30, 2003). "Genome-Wide Analysis of the Response to Cell Wall Mutations in the Yeast *Saccharomyces cerevisiae*," *J. Biol. Chem.* 278(22):20345-20357.

Lairmore, M.D. et al. (Oct. 1995). "Human T-Lymphotropic Virus Type 1 Peptides in Chimeric and Multivalent Constructs with Promiscuous T-Cell Epitopes Enhance Immunogenicity and Overcome Genetic Restriction," *J. Virol.* 69(10):6077-6089.

Land, A. et al. (2001). "Folding of the Human Immunodeficiency Virus Type 1 Envelope Glycoprotein in the Endoplasmic Reticulum," *Biochimie* 83:783-790.

Lee, B.H. et al. (Dec. 2001). "cis Expression of DC-SIGN Allows for More Efficient Entry of Human and Simian Immunodeficiency Viruses via CD4 and a Coreceptor," *J. Virol.* 75(24):12028-12038.

Lee, B.N. et al. (Oct. 26, 1999). "The MAPKKK Ste11 Regulates Vegetative Growth Through a Kinase Cascade of Shared Signaling Components," *Proc. Natl. Acad Sci.USA* 96(22)12679-12684.

Lee, H.K. et al. (Feb. 4, 2004). "Reactivity-Based One-Pot Synthesis of Oligomannoses: Defining Antigens Recognized by 2G12, a Broadly Neutralizing Anti-HIV-1 Antibody," *Angew. Chem. Int. Ed. Engl.* 43(8):1000-1003.

Lehle, L. et al. (Aug. 14, 1995). "Glycoprotein Biosynthesis in *Saccharomyces cerevisiae: ngd29*, an *N*-glycosylation Mutant Allelic to *och1* Having a Defect in the Initiation of Outer Chain Formation," *FEBS Lett.* 370(1-2):41-45.

Leonard, C.K. et al. (Jun. 25, 1990). "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells," *J. Biol. Chem.* 265(18):10373-10382.

Lesinski, G.B. et al. (2001). "Vaccines Against Polysaccharide Antigens," *Curr. Drug Targets Infect. Disord.* 1(3):325-334.

Lesinski, G.B. et al. (Nov. 2001). "Novel Vaccine Strategies to T-Independent Antigens," *J. Microbiol. Methods* 47(2):135-149.

Li, B. et al. (Nov. 27, 2005). "Highly Efficient Endoglycosidase-Catalyzed Synthesis of Glycopeptides Using Oligosaccharide Oxazolines as Donor Substrates," *J. Am. Chem. Soc.* 127(27):9692-9693.

Li, H. et al. (2004). "Design and Synthesis of a Template-Assembled Oligomannose Cluster as an Epitope Mimic for Human HIV-Neutralizing Antibody 2G12," *Org. Biomol. Chem.* 2(4):483-488.

Li, H. et al. (Nov. 25, 2005). "Chemoenzymatic Synthesis of HIV-1 V3 Glycopeptides Carrying Two *N*-Glycans and Effects of Glycosylation on the Peptide Domain," *J. Org. Chem.* 70(24):9990-9996.

Li, M. et al. (Aug. 2005). "Human Immunodeficiency Virus Type 1 *env* Clones from Acute and Early Subtype B Infections for Standardized Assessments of Vaccine-Elicited Neutralizing Antibodies," *J. Virol.* 79(16):10108-10125.

Lin, G. et al. (Jan. 2003). "Differential N-linked Glycosylation of Human Immunodeficiency Virus and Ebola Virus Envelope Glycoproteins Modulates Interactions with DC-SIGN and DC-SIGNR," *J. Virology* 77(2):1337-1346.

Liu, W.F. et al. (1998). "Expression of the Extracellular Domain of the Human Immunodeficiency Virus Type 1 Envelope Protein and its Fusion with β-galactosidase in *Saccharomyces cerevisiae*." *Clin Diagn lab Immunol.* 5(4):592-594.

Livi, G.P. et al. (1990). "Secretion of *N*-Glycosylated Human Recombinant Interleukin-1α in *Saccharomyces cerevisiae*," *Gene* 88(2):297-301.

Lockhart, S. (Oct. 2003). "Conjugate Vaccines," *Expert Rev. Vaccines* 2(5):633-648.

Mandal, M. et al. (May 3, 2004). "In Pursuit of Carbohydrate-Based HIV Vaccines, Part 1: The Total Synthesis of Hybrid-Type gp120 Fragments," *Angew. Chem. Int. Ed.* 43(19):2557-2561.

Mascola, J.R. et al. (Aug. 2005). "Recommendations for the Design and Use of Standard Virus Panels to Assess Neutralizing Antibody Responses Elicited by Candidate Human Immunodeficiency Virus Type 1 Vaccines," *J. Virol.* 79(16):10103-10107.

Mata, J.E. et al. (1997). "A Hexameric Phosphorothioate Oligonucleotide Telomerase Inhibitor Arrests Growth of Burkitt's Lymphoma Cells in Vitro and in Vivo," *Toxicol. Appl. Pharmacol.* 144:189-97.

McCutchan, F.E. et al. (1992). "Genetic Variants of HIV-1 in Thailand," *AIDS Res. Human Retroviruses* 8(11):1887-1895.

McMichael, A.J. et al. (Jul. 2003). "HIV Vaccines 1983-2003," *Nat. Med.* 9(7):874-880.

McMichael, A.J. (2006). "HIV Vaccines," *Annu. Rev. Immunol.* 24:227-255.

Mendez, M.J. et al. (Feb. 1997). "Functional Transplant of Megabase Human Immunoglobulin loci Recapitulates Human Antibody Response in Mice," *Nat. Genet.* 15(2):146-156.

Merrifield, B. (1997). "Concept and Early Development of Solid-Phase Peptide Synthesis" Chapter 1 *In Methods in Enzymology*, Acadmeic Press, Inc.: New York, NY, 289:3-13.

Mitchell, D.A. et al. (Aug. 3, 2001). "A Novel Mechanism of Carbohydrate Recognition by the C-Type Lectins DC-SIGN and DC-SIGNR. Subunit Organization and Binding to Multivalent Ligands," *J/Biol/Chem.* 276(31):28939-28945.

Modrow, S. et al. (Feb. 1987). "Computer-Assisted Analysis of Envelope Protein Sequences of Seven Human Immunodeficiency Virus Isolates: Prediction of Antigenic Epitopes in Conserved and Variable Regions," *J. Virol.* 61(2):570-578.

Mond, J.J. et al. (1995). "T Cell-Independent Antigens Type 2," *Annu. Rev. Immunol.* 13:655-692.

Mori, T. et al. (2002). "Functional Homolgs of Cyanovirin-N Amenable to Mass Production in Prokaryotic and Eukaryotic Hosts," *Protein Expr. Purif.* 26(1):42-49.

Muesing, M.A. et al. (Feb. 7, 1985). "Nucleic Acid Structure and Expression of the Human AIDS/Lymphadenopathy Retrovirus," *Nature.* 313:450-458.

Müller, W.E.G. et al. (Feb. 1990). "Polyclonal Antibodies to Mannan from Yeast also Recognize the Carbohydrate Structure of gp120 of the AIDS Virus: an Approach to Raise Neutralizing Antibodies to HIV-1 Infection in vitro," *AIDS* 4(2):159-162.

Myers, G. et al. eds. (1987). "Human Retroviruses and AIDS 1987: A Compilation and Analysis of Nucleic Acid and Amino Acid Sequences," *Theoretical Biology and Biophysics Group T-10, Los Alamos National Laboratory*, Preface, Introduction and Table of Contents Only, 8 pages.

Nakajima, T. et al. (Oct. 1975). "Yeast Manno-Protein Biosynthesis: Solubilization and Selective Assay of Four Mannosyltransferases," *Proc. Nat. Acad. Sci. USA* 72(10):3912-3916.

Nakanishi-Shindo, Y. et al. (Dec. 15, 1993). "Structure of the *N*-Linked Oligosaccharides That Show the Complete Loss of α-1,6-Polymannose Outer Chain from *och1*, *och1 mnn1*, and *och1 mnn1 alg3* Mutants of *Saccharomyces cerevisiae*," *J. Biol. Chem.* 268(35):26338-26345.

Nakayama, K. et al. (Jul. 1992). "*OCH1* Encodes a Novel Membrane Bound Mannosyltransferase: Outer Chain Elongation of Asparagine-Linked Oligosaccharides," *The EMBO Journal* 11(7):2511-2519.

Nakayama, K. et al. (Sep. 16, 1998). "The Involvement of *mnn4* and *mnn6* Mutations in Mannosylphosphorylation of *O*-Linked Oligosaccharide in Yeast *Saccharomyces cerevisiae*," *Biochim. Biophys. Acta.* 1425(1):255-262.

Narum, D.L. et al. (Dec. 2001). "Codon Optimization of Gene Fragments Encoding *Plasmodium falciparum* Merzoite Proteins Enhances DNA Vaccine Protein Expression and Immunogenicity in Mice," *Infect. Immun.* 69(12):7250-7253.

Odani, T. et al. (1996). "Cloning and Analysis of the *MNN4* Gene Required for Phosphorylation of *N*-linked Oligosaccharides in *Saccharomyces cerevisiae*," *Glycobiology* 6(8):805-810.

Oppermann, M. et al. (2004). "Chemokine Receptor CCR5: Insights into Structure, Function, and Regulation," *Cell. Signal.* 16:1201-1210.

Ou, C-Y. et al. (May 22, 1992). "Molecular Epidemiology of HIV Transmission in a Dental Practice," *Science* 256:1165-1171.

Outchkourov, N.S. et al. (Feb. 2002). "Optimization of the Expression of Equistatin in *Pichia pastoris*," *Protein Expr. Purif.* 24(1):18-24.

Ozinsky, A. et al. (Dec. 5, 2000). "The Repertoire for Pattern Recognition of Pathogens by the Innate Immune System is Defined by Cooperation Between Toll-Like Receptors," *Proc. Natl. Acad. Sci. USA* 97(25):13766-13771.

Panina-Bordignon, P. et al. (1989). "Universally Immunogenic T Cell Epitopes: Promiscuous Binding to Human MHC Class II and Promiscuous Recognition by T Cells," *Eur. J. Immunol.* 19(12):2237-2242.

Pantophlet, R. et al. (2006). "GP120: Target for Neutralizing HIV-1 Antibodies," *Annu. Rev. Immunol.* 24:739-769.

Paoletti, L.C. et al. (Dec. 1, 2002). "Neutralizing Antibody Induced in Mice by Novel Glycoconjugates of Human Immunodeficiency Virus Type 1 gp120 and env2-3," *J. Infect. Dis.* 186(11)1597-1602.

Pardo, M. et al. (Apr. 1999). "Two-Dimensional Analysis of Proteins Secreted by *Saccharomyces cerevisiae* Regenerating Protoplasts: a Novel Approach to Study the Cell Wall," *Yeast.* 15(6):459-472.

Pardo, M. (2004). "*PST1* and *ECM33* Encode Two Yeast Cell Surface GPI Proteins Important for Cell Wall Integrity," *Microbiology* 150:4157-4170.

Pawlowski, A. et al. (1999). "A New Method of Non-Cross-Linking Conjugation of Polysaccharides to Proteins via Thioether Bonds for the Preparation of Saccharide-Protein Conjugate Vaccines," *Vaccine* 17:1474-1483.

Perrin, L. et al. (Jan. 2003). "Travel and the Spread of HIV-1 Genetic Variants," *Lancet Infect. Dis.* 3(1): 22-27.

Philpott, S.M. (2003). "HIV-1 Coreceptor Usage, Transmission, and Disease Progression," *Curr. HIV Res.* 1(2):217-227.

Pöhlmann, S. et al. (Feb. 27, 2001). "DC-SIGNR, a DC-SIGN Homologue Expressed in Endothelial Cells, Binds to Human and Simian Immunodeficiency Viruses and Activates Infection in Trans," *Proc. Natl. Acad. Sci. USA* 98(5):2670-2675.

Pöhlmann, S. et al. (May 2001). "DC-SIGN Interactions with Human Immunodeficiency Virus Type 1 and 2 and Simian Immunodeficiency Virus," *J. Virol.* 75(10):4664-4672.

Pöhlmann, S. et al. (Nov. 2001). "DC-SIGN Interactions with Human Immunodeficiency Virus: Virus Binding and Transfer are Dissociable Functions," *J. Virol.* 75(21):10523-10526.

Pöhlmann, S. et al. (Dec. 2001). "DC-SIGN and DC-SIGNR: Helping Hands for HIV," *Trends Immunol.* 22(12):643-646.

Pöhlmann, S. et al. (Mar. 2002). "Evaluation of Current Approaches to Inhibit HIV Entry," *Curr. Drug Targets Infect. Disord.* 2(1):9-16.

Pöhlmann, S. et al. (Apr. 2003). "Hepatitis C Virus Glycoproteins Interact with DC-SIGN and DC-SIGNR," *J. Virol.* 77(7):4070-4080.

Raschke, W.C. et al. (Jul. 10, 1973). "Genetic Control of Yeast Mannan Structure. Isolation and Characterization of Mannan Mutants," *J. Biol. Chem.* 248(13):4660-4666.

Ratner, L. et al. (Jan. 24, 1985). "Complete Nucleotide Sequence of the AIDS Virus, HTLV-III," *Nature.* 313:227-284.

Reece, J.C. et al. (Dec. 1, 1993). "Mapping the Major Human T Helper Epitopes of Tetanus Toxin. The Emerging Picture," *J. Immunol.* 151(11):6175-6184.

Richman, D.D. et al. (Apr. 1, 2003). "Rapid Evolution of the Neutralizing Antibody Response to HIV Type 1 Infection," *Proc. Natl. Acad. Sci. USA* 100(7):4144-4149.

Roberge, J.Y. et al. (Jul. 14, 1995). "A Strategy for a Convergent Synthesis of N-Linked Glycopeptides on a Solid Support," *Science* 269:202-204.

Roux, K.H. et al. (2004). "Electron Microscopic and Immunochemical Analysis of the Broadly Neutralizing HIV-1-specific, Anti-Carbohydrate Antibody, 2G12," *Mol. Immunol.* 41(10):1001-1011.

Rudd, P.M. et al. (1997). "Glycosylation: Heterogeneity and the 3D Structure of Proteins," *Crit. Rev. Biochem. Mol. Biol.* 32(1):1-100.

Rudolph, H.K. et al. (Jul. 14, 1989). "The Yeast Secretory Pathway Is Perturbed by Mutations in *PMR1*, a Member of a $Ca^{2+}$ ATPase Family," *Cell* 58(1):133-145.

Samstag, W. et al. (Fall 1996). "Synthesis and Properties of New Antisense Oligodeoxynucleotides Containing Benzylphosphonate Linkages," *Antisense & Nucleic Acid Drug Dev.* 6(3):153-156.

Sanders, R.W. et al. (Jul. 2002). "The Mannose-Dependent Epitope for Neutralizing Antibody 2G12 on Human Immunodeficiency Virus Type 1 Glycoprotein gp120," *J. Virol.* 76(14):7293-7305.

Sandström, C. et al. (Nov. 9, 2004). "Atomic Mapping of the Interactions Between the Antiviral Agent Cyanovirin-N and Oligomannosides by Saturation-Transfer Difference NMR," *Biochemistry* 43(44):13926-13931.

Sato, M. et al. (Jul. 1, 2003). "Direct Binding of Toll-Like Receptor 2 to Zymosan, and Zymosan-Induced NF-κb Activation and TNF-α Secretion Are Down-Regulated by Lung Collectin Surfactant Protein A," *J. Immunol.* 171(1):417-425.

Scanlan, C.N. (Jul. 2002). "The Broadly Neutralizing Anti-Human Immunodeficiency Virus Type 1 Antibody 2G12 Recognizes a Cluster of α1->2 Mannose Residues on the Outer Face of gp120," *J. Virol.* 76(14):7306-7321.

Schmidt, M.A. et al. (Dec. 2003). "Sweet New World: Glycoproteins in Bacterial Pathogens," *Trends in Microbiology* 11(12):554-561.

Shattock, R.J. (Oct. 2003). "Inhibiting Sexual Transmission of HIV-1 Infection," *Nat. Rev. Microbiol.* 1(1):25-34.

Singh, S. et al. (2003). "Chemoenzymatic Synthesis of High-Mannose Type HIV-1 Gp120 Glycopeptides," *Bioorg. Med. Chem. Lett.* 13(3):327-330.

Smith, R.A. (Sep. 1985). "Heterologous Protein Secretion from Yeast," *Science* 229(4719):1219-1224.

Strahl-Bolsinger, S. et al. (1999). "Protein O-mannosylation," *Biochim. Biophys. Acta.* 1426(2):297-307.

Strauss-Soukup, J.K. et al. (1997). "Effects of Neutralization Pattern and Stereochemistry on DNA Bending by Methylphosphonate Substitutions," *Biochemistry* 36:8692-8698.

Sundaram, R. et al. (2004). "Structural and Immunogenicity Analysis of Chimeric B-cell Epitope Constructs Derived From the gp46 and gp21 Subunits of the Envelope Glycoproteins of HTLV-1," *J. Pept. Res.* 63(2):132-140.

Terashima, H. et al. (Sep. 2000). "Up-Regulation of Genes Encoding Glycosylphosphatidylinositol (GPI)-Attached Proteins in Response to Cell Wall Damage Caused by Disruption of *FKS1* in *Saccharomyces cerevisiae*," *Mol. Gen. Genet.* 264(1-2):64-74.

Trkola, A. et al. (Feb. 1996). "Human Monoclonal Antibody 2G12 Defines a Distinctive Neutralization Epitope on the gp120 Glycoprotein of Human Immunodeficiency Virus Type 1," *J. Virol.* 70(2):1100-1108.

Tsai, C.C. et al. (2003). "Cyanovirin-N Gel as a Topical Microbicide Prevents Rectal Transmission of SHIV89.6P in Macaques." *AIDS Res. Hum. Retroviruses* 19(7):535-541.

Tsai, C.C. et al. (2004). "Cyanovirin-N Inhibits AIDS Virus Infections in Vaginal Transmission Models." *AIDS Res. Hum. Retroviruses* 20(1):11-18.

Tuite, M.F. et al. (1999). "Expressing Cloned Genes in the Yeasts *Saccharomyces cerevisiae* and *Pichia pastoris*" Chapter 3 *In Protein Expression: A Practical Approach*, Higgins, S.J. et al., eds., Oxford University Press, pp. 61-100.

UNAIDS (Jun. 2004). "2004 Report on the Global AIDS Epidemic—4th Global Report," *Joint United Nations Programme on HIV/AIDS*, 231 pages.

UNAIDS (2006). "25 Years of AIDS: 2006 Report on the Global AIDS Epidemic," *Joint United Nations Programme on HIV/AIDS*, 66 pages.

UNAIDS (2006). "25 Years of AIDS: 2006 Report on the Global AIDS Epidemic, Executive Summary," *Joint United Nations Programme on HIV/AIDS*, 5 pages.

UNAIDS (2006). "Global Summary of the HIV and AIDS Epidemic, 2005," *Joint United Nations Programme on HIV/AIDS*, 11 pages.

UNAIDS (Dec. 2006). "2006 AIDS Epidemic Update: Global Summary of the AIDS Epidemic," *Joint United Nations Programme on HIV/AIDS*, two pages.

Valmori, D. et al. (Jul. 15, 1992). "Use of Human Universally Antigenic Tetanus Toxin T Cell Epitopes as Carriers for Human Vaccination," *J. Immunol.* 149(2):717-721.

Varki, A. et al. eds. (1999). *Essentials in Glycobiology*, Cold Spring Harbor Laboratory Press, Cold Spring Harbor, NY, pp. v-vi (Table of Contents Only.).

Veazey, R.S. et al. (Mar. 2003). "Prevention of Virus Transmission to Macaque Monkeys by a Vaginally Applied Monoclonal Antibody to HIV-1 gp120," *Nat. Med.* 9(3):343-346.

Verostek, M.F. et al. (Oct. 1995). "Mannosyltransferase Activities in Membranes from Various Yeast Strains." *Glycobiology* 5(7):671-681.

Vervecken, W. et al. (May 2004). "In Vivo Synthesis of Mammalian-Like, Hybrid-Type N-Glycans in *Pichia pastoris*," *Applied and Enviromental Microbiology*. 70(5):2639-2646.

Viitala, J. et al. (Jun. 1988). "Molecular Cloning of cDNAs Encoding Lamp A, A Human Lysosomal Membrane Glycoprotein with Apparent $M_r$=120,000," *Proc. Natl. Acad. Sci. USA* 85(11):3743-3747.

Vogel, F.R. et al. (2004). "Immunologic Adjuvants" Chapter 6 *In Vaccines*, Fourth Edition, Plotkin, et al. eds., Saunders. pp. 69-79.

Wainberg, M.A. (2004). "HIV-1 Subtype Distribution and the Problem of Drug Resistance," *AIDS* 18(Suppl 3):S63-S68.

Wang, L-X. (2006) "Toward Oligosaccharide-and Glycopeptide-Based HIV Vaccines," *Curr. Opin. Drug. Discov. Devel.* 9(2):194-206.

Wang, L-X. et al. (Jan. 2004). "Binding of High-Mannose-Type Oligosaccharides and Synthetic Oligomannose Clusters to Human Antibody 2G12: Implications for HIV-1 Vaccine Design," *Chem. Biol.* 11:127-34.

Wang, L-X. et al. (Jun. 2005). "Chemoenzymatic Synthesis of HIV-1 gp41 Glycopeptides: Effects of Glycosylation on the Anti-HIV Activity and α-Helix Bundle-Forming Ability of Peptide C34," *ChemBioChem.* 6(6):1068-1074.

Wei, X. et al. (Mar. 20, 2003). "Antibody Neutralization and Escape by HIV-1," *Nature* 422:307-312.

Wei, X. et al. (May 3, 2003). "Antibody Neutralization and Escape by HIV-1," *Nature* Erratum 423:197.

Weis, W.I. et al. (1998). "The C-Type Lectin Superfamily in the Immune System," *Immunol. Rev.* 163:19-34.

Wildt, S. et al. (Feb. 2005). "The Humanization of N-Glycosylation Pathways in Yeast," *Nature Reviews Microbiology.* 3(2):119-127.

Winzeler, E.A. et al. (Aug. 6, 1999). "Functional Characterization of the *S. cerevisiae* Genome by Gene Deletion and Parallel Analysis," *Science* 285:901-906.

Wolinsky, S.M. (Feb. 28, 1992). "Selective Transmission of Human Immunodeficiency Virus Type-1 Variants from Mothers to Infants," *Science* 255:1134-1137.

Woods, R.J. et al. (Aug. 1994). "Protein Surface Oligosaccharides and Protein Function," *Nature Struct. Biol.* 1(8):499-501.

Yeh, J.C. et al. (1993). "Site-Specific N-Glycosylation and Oligosaccharide Structures of Recombinant HIV-1 gp120 Derived From a Baculovirus Expression System," *Biochemistry* 32(41)11087-11099.

Yin, Q.Y. et al. (May 27, 2005). "Comprehensive Proteomic Analysis of *Saccharomyces cerevisiae* Cell Walls: Identification of Proteins Covalently Attached via Glycosylphosphatidylinositol Remnants or Mild Alkali-Sensitive Linkages," *J. Biol. Chem.* 280(21):20894-20901.

Yip, C.L. et al. (Mar. 1994). "Cloning and Analysis of the *Saccharomyces cerevisiae MNN9* and *MNN1* Genes Required for Complex Glycosylation of Secreted Proteins," *Proc. Natl. Acad. Sci. USA* 91:2723-2727.

Zhang, L.Q. et al. (1991). "Detection, Quantification and Sequencing of HIV-1 from the Plasma of Seropositive Individuals and from Factor VIII Concentrates," *AIDS* 5(6):675-681.

Zhu, X. et al. (Sep. 19, 2000). "Mass Spectrometric Characterization of the Glycosylation Pattern of HIV-gp120 Expressed in CHO Cells," *Biochemistry* 39(37):11194-11204.

Zolla-Pazner, S. (Mar. 2004). "Identifying Epitopes of HIV-1 That Induce Protective Antibodies," *Nat. Rev. Immunol.* 4(3):199-210.

Astronomo, R.D. et al. (Jul. 2008, e-pub. Apr. 23, 2008). "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," *Journal of Virology* 82(13):6359-6368.

Hessell, A.J. et al. (May 15, 2009). "Broadly Neutralizing Human Anti-HIV Antibodies 2G12 Is Effective in Protection Against Mucosal SHIV Challenge Even at Low Serum Neutralizing Titers," *PLOS Pathogens* 5(5):1-9.

Joos, B. et al. (May 2006). "Long-Term Multiple-Dose Pharmacokinetics of Human Monoclonal Antibodies (MAbs) Against Human Immunodeficiency Virus Type 1 Envelope gp102 (MAb 2G12) and gp41 (MAbs 4E10 and 2F5)," *Antimicrobial Agents and Chemotherapy* 50(5):1773-1779.

Krauss, I.J. et al. (2007, e-pub. Aug. 21, 2007). "Fully Synthetic Carbohydrate HIV Antigens Designed on the Logic of the 2G12 Antibody," *J. Am. Chem. Soc.* 129(36):11042-11044.

Luallen, R.J. et al. (Mar. 2009). "A Heterologous Yeast Glycoprotein to Target the Glycans on HIV-1," Poster 311, *presented at the Keystone Symposia On Molecular and Cellular Biology*, Keystone, Colorado, Mar. 22-27, 2009, two pages.

Luallen, R.J. et al. (Mar. 23, 2010). "Adjuvant Effect on the Induction of Glycan-Specific Antibodies Against HIV Env Using Single Yeast Glycoproteins," Poster 250, *presented at the Keystone Symposia On Molecular and Cellular Biology*, Banff, Alberta, Canada, Mar. 21-26, 2010, two pages.

Ni, J. et al. (2006, e-pub. Feb. 21, 2006). "Toward a Carbohydrate-Based HIV-1 Vaccine: Synthesis and Immunological Studies of Oligonmannose-Containing Glycoconjugates," *Bioconjugate Chem.* 17(2):493-500.

Wang, S-K. et al. (Mar. 11, 2008). "Targeting the Carbohydrates on HIV-1: Interaction of Oligonmannose Dendrons with Human Monoclonal Antibody 2G12 and DC-SIGN," *PNAS* 105(10):3690-3695.

Buchacher, A. et al. (Apr. 1994). "Generation of Human Monoclonal Antibodies Against HIV-1 Proteins; Electrofusion and Epstein-Barr Virus Transformation for Peripheral Blood Lymphocyte Immortalization," *AIDS Res Hum Retroviruses* 10(4):359-369.

Crawford, J.M. et al. (Dec. 1999). "Characterization of Primary Isolate-Like Variants of Simian-Human Immunodeficiency Virus," *Journal of Virology* 73(12):10199-10207.

Etemad-Moghadam, B. et al. (Oct. 1999). "Determinants of Neutralization Resistance in the Envelope Glycoproteins of a Simian-Human Immunodeficiency Virus Passaged In Vivo," *Journal of Virology* 73(10):8873-8879.

Katinger, H. (2010, last revised Aug. 30, 2010). "HIV-1gp120 Monoclonal (2G12), Data Sheet, Catalogue No. 1476, Lot Number: 17 098154 and Lot Number: 18 098204," *NIH AIDS Research & Reference Reagent Program*, two pages.

Mascola, J.R. et al. (May 1999). "Protection of Macaques Against Pathogenic Simian/Human Immunodeficiency Virus 89.6PD by Passive Transfer of Neutralizing Antibodies," *Journal of Virology* 73(5):4009-4018.

Doores, K.J. et al. (Aug. 3, 2010). "Envelope Glycans of Immunodeficiency Virions are Almost Entirely Oligomannose Antigens," *PNAS* 107(31):13800-13805.

Mizuochi, T. et al. (1999). "HIV Infection and Oligosaccharides: A Novel Approach to Preventing HIV Infection and the Onset of AIDS," *J. Infect. Chemother.* 5:190-195.

Walker, L.M. et al. (Aug. 2010). "A Limited Number of Antibody Specificities Mediate Broad and Potent Serum Neutralization in Selected HIV-1 Infected Individuals," *PLoS Pathogens* 6(8-e1001028):1-14.

White, T.A. et al. (Dec. 2010). "Molecular Architectures of Trimeric SIV and HIV-1 Envelope Glycoproteins on Intact Viruses: Strain-Dependent Variation in Quaternary Structure," *PLos Pathogens* 6(12-e1001249):1-14.

\* cited by examiner

FIGURE 4
A
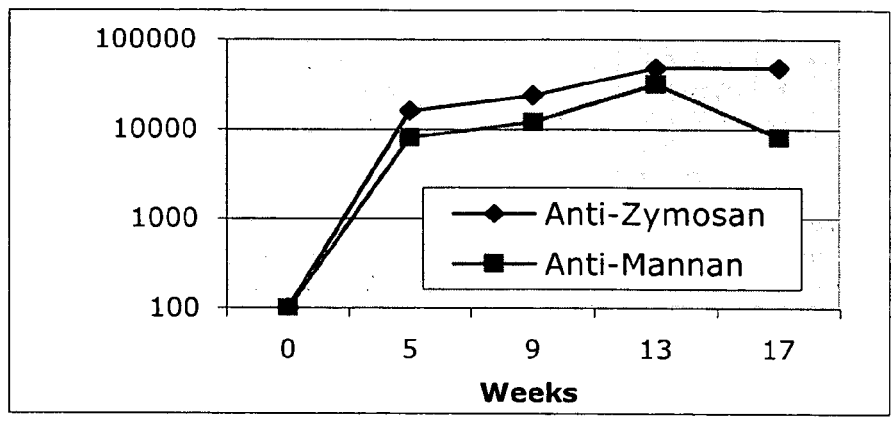
B
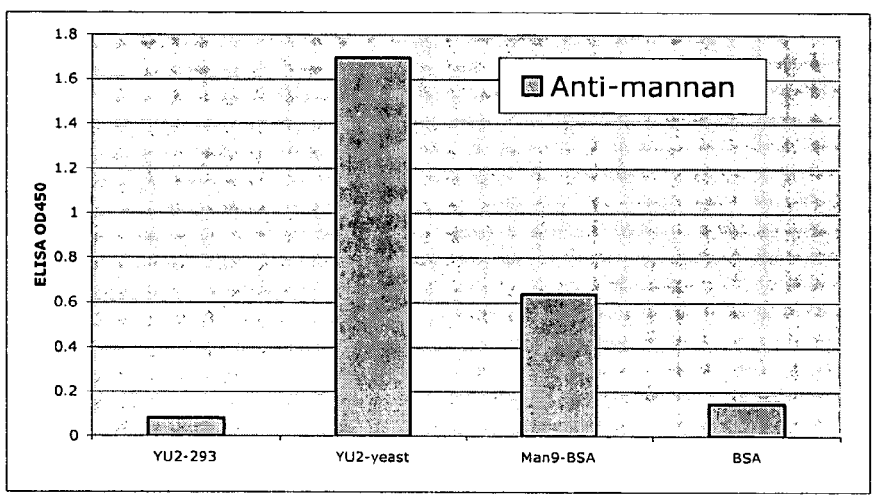
C
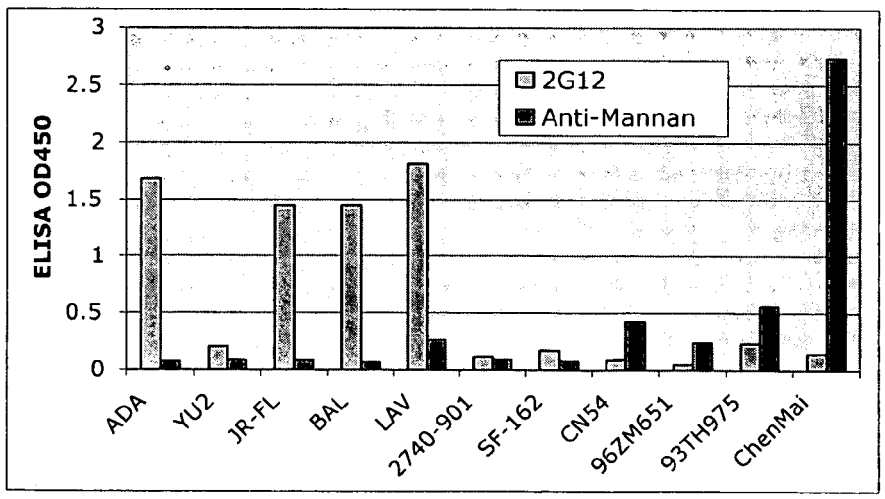

FIGURE 6
A
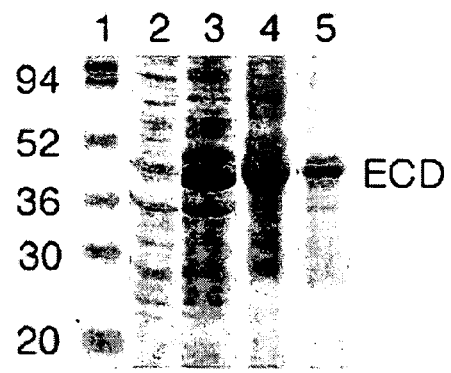
B
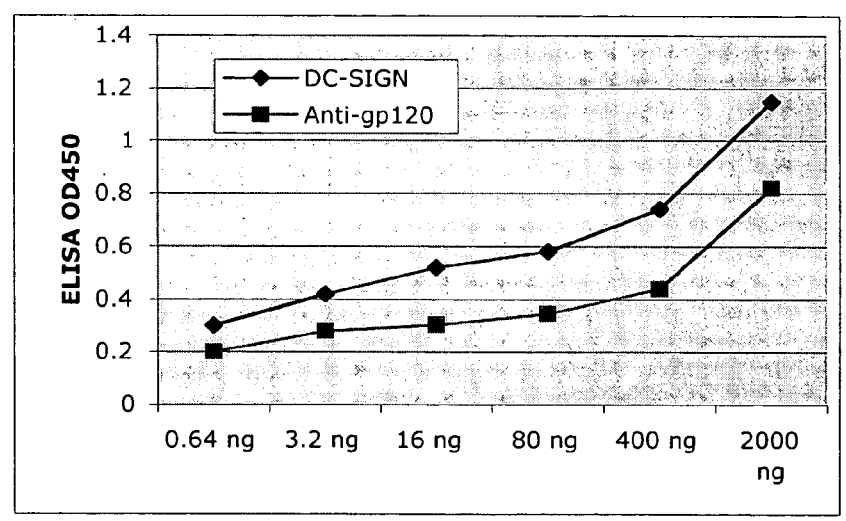

MQLHSLIASTALLITSALAATSSSSSIPSSCTISSHATATAQSDLDKYSRCDTLVGNLTIGGGLKTGALANVKEI
NGSLTIFNATNLTSFAADSLESITDSLNLQSLTILTSASFGSLQSVDSIKLITLPAISSFTSNIKSANNIYISDT
SLQSVDGFSALKKVNVFNVNNNKKLTSIKSPVETVSDSLQFSFNGNQTKITFDDLVWANNISLTDVHSVSFANLQ
KINSSLGFINNSISSLNFTKLNTIGQTFSIVSNDYLKNLSFSNLSTIGGALVVANNTGLQKIGGLDNLTTIGGTL
EVVGNFTSLNLDSLKSVKGGADVESKSSNFSCNALKALQKKGGIKGESFVCKNGASSTSVKLSSTSKSQSSQTTA
KVSKSSSKAEEKKFTSGDIKAAASASSVSSSGASSSSSKSSKGNAAIMAPIGQTTPLVGLLTAIIMSIM

Figure 13

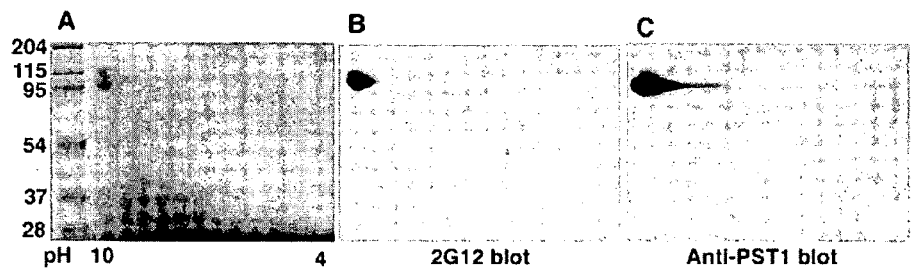

Figure 14

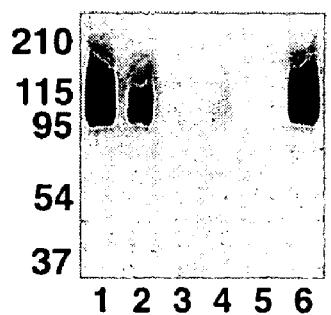

Figure 19

| PST1 HomoloGene among 18 Species | | |
|---|---|---|
| Mammalian | Homo sapiens | Human |
| | Pan troglodytes | Chimpanzee |
| | Canis familiaris | Dog |
| | Mus musculus | House mouse |
| | Rattus norvegicus | Rat |
| Bird | Gallus gallus | Chicken |
| Insect | Drosophila melanogaster | Fly |
| | Anopheles gambiae | Mosquito |
| Worm | Caenorhabditis elegans | Small soil nematode |
| Fungus | Saccharomyces cerevisiae | Yeast |
| | Schizosaccharomyces pombe | Yeast |
| | Kluyveromyces lactis | Yeast |
| | Eremothecium gossypii | Cotton pathogen |
| | Magnaporthe grisea | Rice blast fungus |
| | Neurospora crassa | Red bread mold |
| Plant | Arabidopsis thaliana | Small flowering plant |
| | Oryza sativa | Japanese rice |
| Parasite | Plasmodium falciparum | malaria parasite |

Figure 20

A
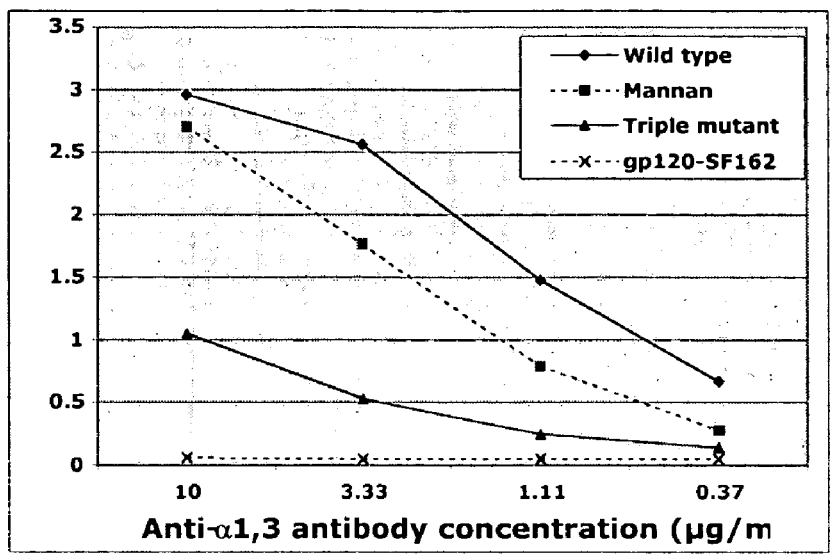
B
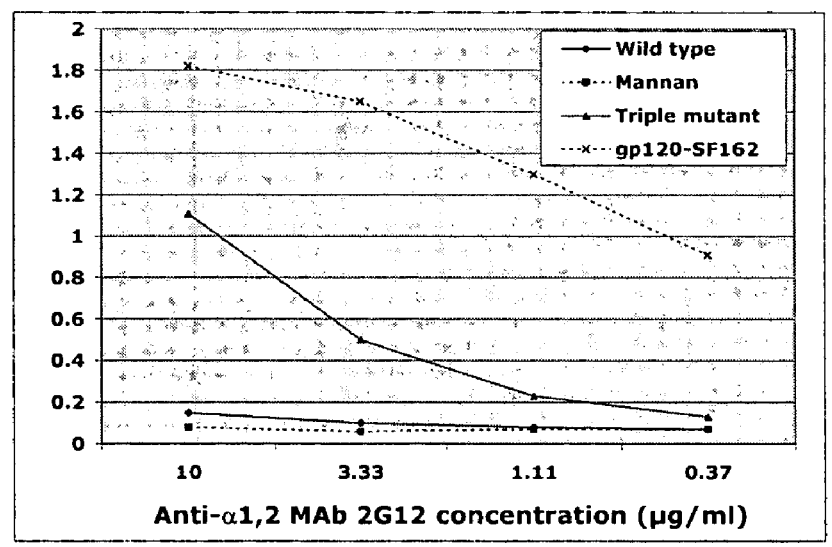
Figure 22

PST1

A.
MQLHSLIASTALLITSALAATSSSSSIPSSCTISSHATATAQSDLDKYSRCDTLVGNLTIGGGLKTGALANVKEINGSL
TIFNATNLTSFAADSLESITDSLNLQSLTILTSASFGSLQSVDSIKLITLPAISSFTSNIKSANNIYISDTSLQSVDGF
SALKKVNVFNVNNNKKLTSIKSPVETVSDSLQFSFNGNQTKITFDDLVWANNLSLTDVHSVSFANLQKINSSLGFINNS
ISSLNFTKLNTIGQTFSIVSNDYLKNLSFSNLSTIGGALVVANNTGLQKIGGLDNLTTIGGTLEVVGNFTSLNLDSLKS
VKGGADVESKSSNFSCNALKALQKKGGIKGESFVCKNGASSTSVKLSSTSKSQSSQTTAKVSKSSSKAEEKKFTSGDIK
AAASASSVSSSGASSSSSKSSKGNAAIMAPIGQTTPLVGLLTAIIMSIM

B.
```
                            .T.......SS.T.............................
.................................................................
.................................................................
.................................................................
.................................................................
......................................T....SS.T................T....
..........S....SSS...S..........................
```

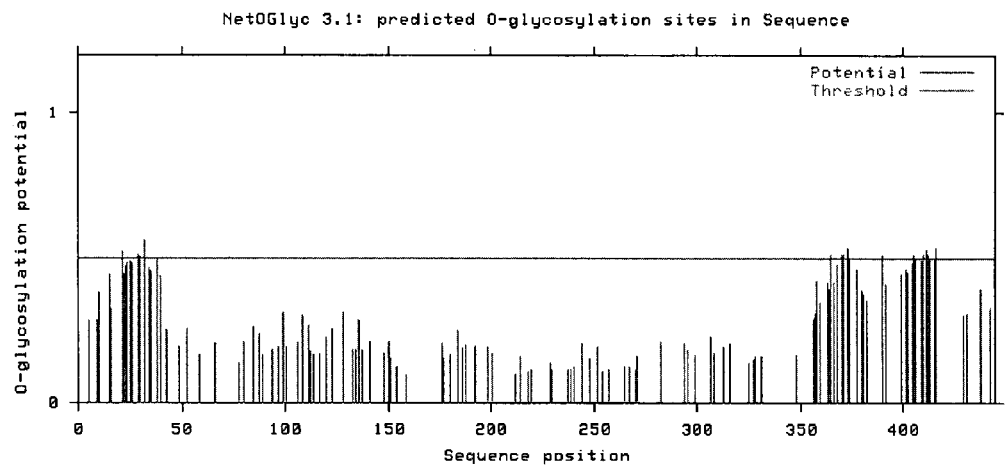

Figure 33

ECM33:

A.
MQFKNALTATAILSASALAAANSTTSIPSSCSIGTSATATAQADLDKISGCSTIVGNLTITGDLGSAALASIQEIDGSL
TIFNSSSLSSFSADSIKKITGDLNMQELIILTSASFGSLQEVDSINMVTLPAISTFSTDLQNANNIIVSDTTLESVEGF
STLKKVNVFNINNNRYLNSFQSSLESVSDSLQFSSNGDNTTLAFDNLVWANNITLRDVNSISFGSLQTVNASLGFINNT
LPSLNLTQLSKVGQSLSIVSNDELSKAAFSNLTTVGGGFIIANNTQLKVIDGFNKVQTVGGAIEVTGNFSTLDLSSLKS
VRGGANFDSSSNFSCNALKKLQSNGAIQGDSFVCKNGATSTSVKLSSTSTESSKSSATSSASSSGDASNAQANVSASA
SSSSSSSKKSKGAAPELVPATSFMGVVAAVGVAYYKIKATICVSIITLISSLMISLPFLFYYETVGSSLNFICR

B.
```
                           ...TT.........T..T............................
............................................................................
............................................................................
............................................................................
............................................................................
.........................................SSTST.SS.SS.TSS.SSS...S...........
......S.....................................................................
```

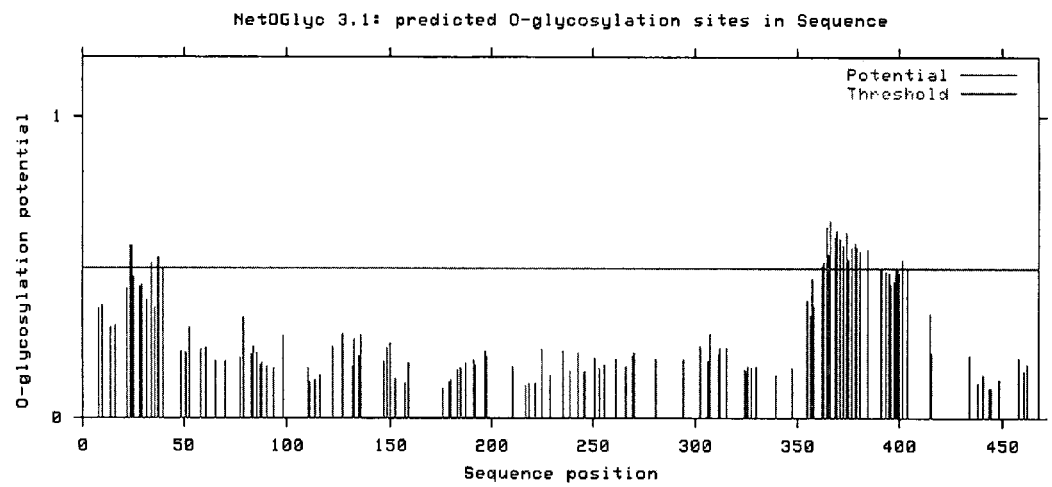

A.
MKFQVVLSALLACSSAVVA*SPIENLFKYRAVKASHSKNI*NSTLPAWNGSNSSNVTYANGTNSTTNTTTAESSQLQIIVT
GGQVPITNSSLTHTNYTRLFNSSSALNITELYNVARVVNETIQDKSSAGAVVVANAKSLEAVSFFFSIIFDTEKPIVVT
EDSAYAIPVANNKNATKRGVLSVTSDKLVYSGVFTPPTACSYGAGLPVAIVDDQDEVKWFFDASKPTLISSDSIIRKEY
SNFTTPYGLLENGVPIVPIVYDGGYSSSLIDSLSSAVQGLVVVSSGSTNSTSSTIESTEIPVVYAQANTPLNFIDNKDV
PKNAVGAGYLSPIKAQILLSIAAVNGVTSKSALESIFP

B.

```
................................................
................................................
................................................
..........................T..T..T...T...........
................................................
```

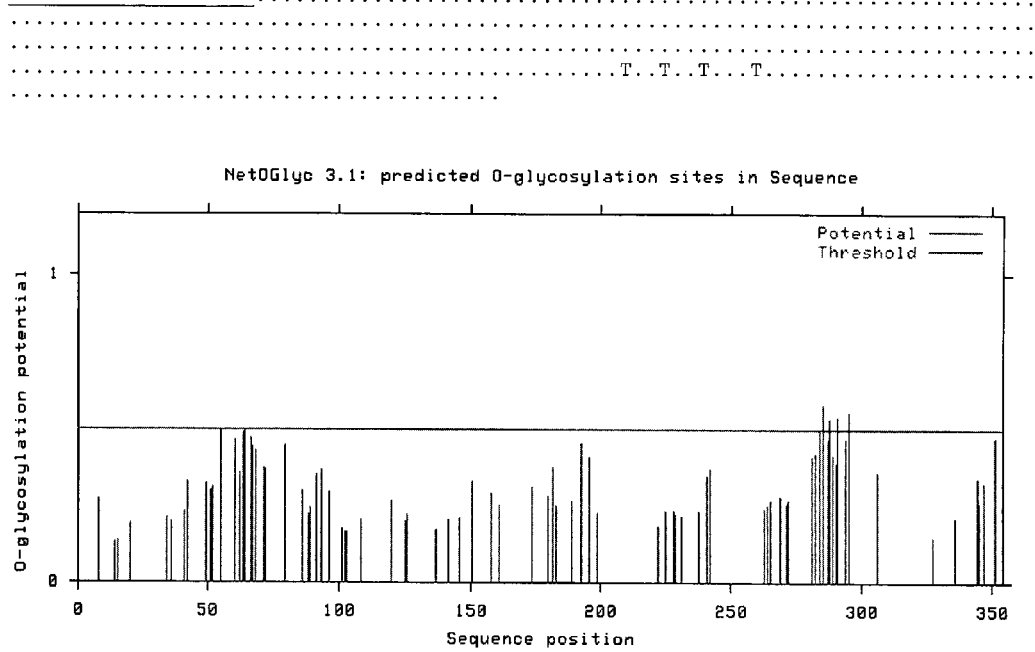

Figure 35

YJL171c

A.
MLQSIVLSVCMFMLHTVAASGPQSYQKLDFTNVGFTGSYVDVNKFKDITN<u>NES</u>CTCEVGDRVWFSGK<u>NAPLADYLSVHF</u>
<u>RGPLKLKQFAFYTSPGFTV</u>NNSRSSSDWNRLAYYESSSKTADNVIFLNHGGEASPCLGNALSYASSNGIGSASEATVLA
DGTLISSDQEYIIYSNVSCPKSGYDKGCGVYRSGIPAYYGYGGTTKMFLFEFEMPTETEKNSSIGYYDLPAIWLLNDH
IARTSQYPTNANCGCWASGCGEYDIFEAMNGTEKNHLYSTFHTFQGIEDLGTGIQSYGYITRNITGTMKGGVVFDSSGN
VVSFISDATPFNGTVSADTVNDLLAAIPENETYSSQLMSISATAPSTTSLSNGVRLTNMQNGVWYYILAIFTAFTQVVL
I

B.

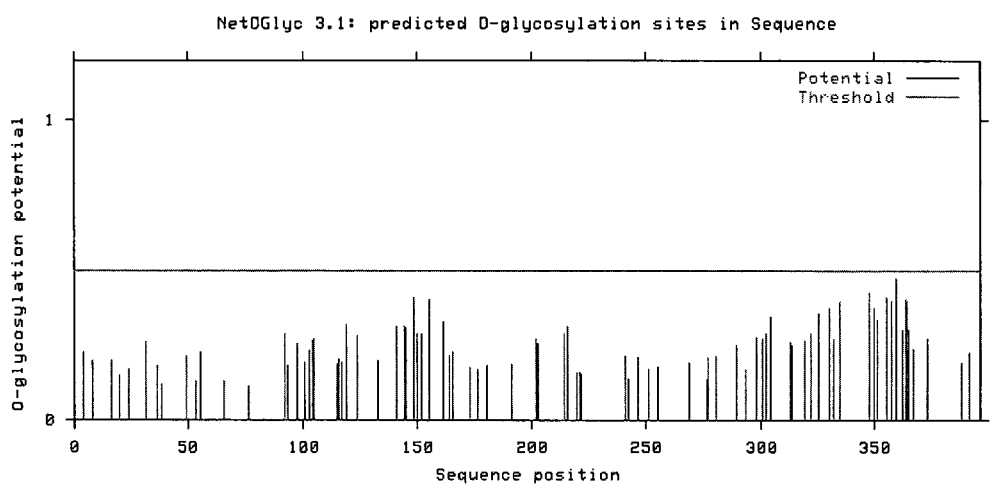

Figure 36

Gas1

A.

MLFKSLSKLATAAAFFAGVATADDVPAIEVVGNKFFYSNNGSQFYIRGVAYQADTANETSGSTVNDPLANYESCSRDIP
YLKKLNTNVIRVYAINTTLDHSECMKALNDADIYVIADLAAPATSINRDDPTWTVDLFNSYKTVVDTFANYTNVLGFFA
GNEVTNNYTNTDASAFVKAAIRDVRQYISDKNYRKIPVGYSSNDDEDTRVKMADYFACGDDDVKADFYGINMYEWCGKS
DFKTSGYADRTAEFKNLSIPVFFSEYGCNEVTPRLFTEVEALYGSNMTDVWSGGIVYMYFEETNKYGLVSIDGNDVKTL
DDFNNYSSEINKISPTSANTKSYSATTSDVACPATGKYWSAATELPPTPNGGLCSCMNAANSCVVSDDVDSDDYETLFN
WICNEVDCSGISANGTAGKYGAYSFCTPKEQLSFVMNLYYEKSGGSKSDCSFSGSATLQTATTQASCSSALKEIGSMGT
NSASGSVDLGSGTESSTASSNASGSSSKSNSGSSGSSSSSSSSSASSSSSSKKNAATNVKANLAQVVFTSIISLSIAAG
VGFALV

B.

```
_____........................
..........................................................
..........................................................
..........................................................
..........................................................
.............................T...........T...............
..........................................................
.............T...T.SS..S.SSS.S.S.SS.SSSSSSSSS.SSS.........
......
```

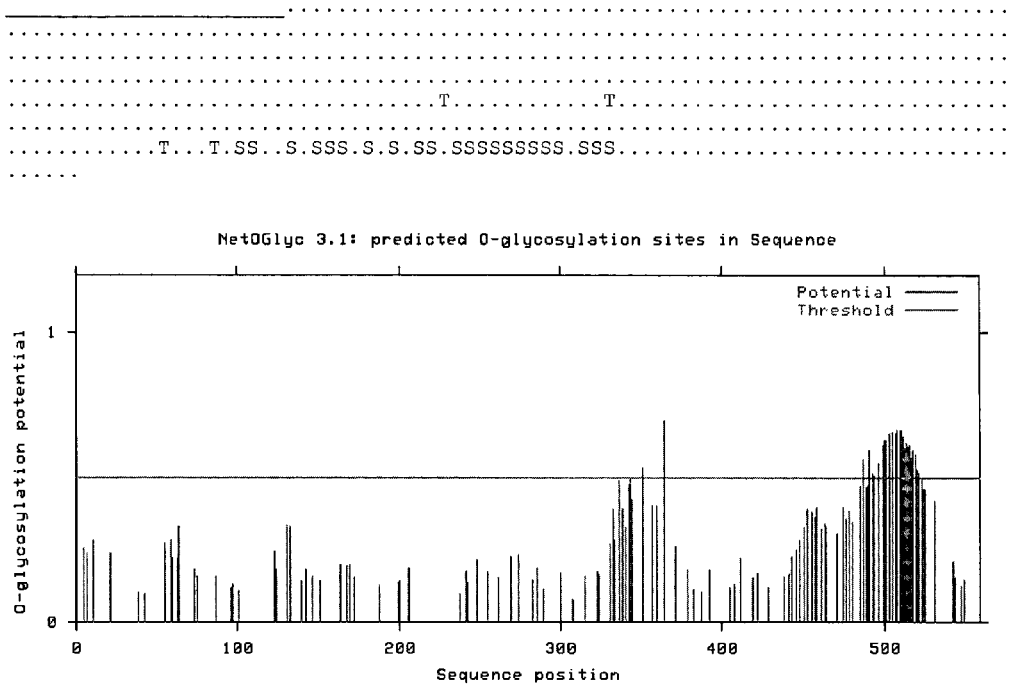

Figure 37

Gas5

A.
MLLRSLTSAFVLSAGLAQAASSSNSSTPSIEIKGNAFFNSESGERFYIRGVDYQPGGSSNLTDPLADASVCDRDVPVLK
DLGINTVRVYTVDNSQDHSHCMKLLQENGIYLILDVNTPTSAISRYDPACSYNADYLQNVFATIDTFADYDNVLGFFAG
NEVINSVNTTNTATYVKAVVRDMKKYIKARKYRQIPVGYSAADIVANRQLAAEYFNCGDEADARIDMFGVNDYSWCGES
SFVVSGYSTKMKLYQDYSVPVFLSEFGCNQVKSSRPFTEIEAIYSTQMSSVFSGGLVYEYSNETNNYGLVQIDGDKVTK
LTDFENLKNEYSKVSNPEGNGGYSTSNNYSTCPDYEKGVWEANNILPAMPSAASAYFTSGAGSPMGTGIATQQSCDAKD
DDDEEDDDTSSSSSSSSSSSSSASSSSESSSSTSKASSSSPSASETSLLKSAASATSSSQSSSKSKG**AAGIIEIPLIFR
ALAELYNLVL**

B.
```
_____ ........................................
.................................................................
.................................................................
.................................................................
.................................................................
.................................................................
........TSSSSSSSSSSSSS.SSSS.SSSSTS..SSSS.S.S.TS...S..S.T..........
..........
```

C.

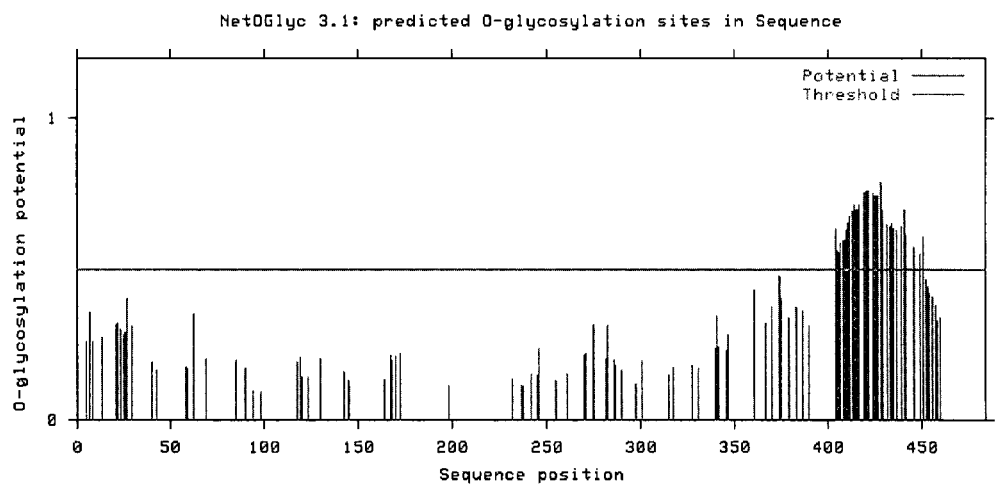

Figure 38

GLYCOSYLATED POLYPEPTIDES PRODUCED IN YEAST MUTANTS AND METHODS OF USE THEREOF

CROSS-REFERENCE TO RELATED APPLICATIONS

This application claims the priority benefit of provisional application U.S. Ser. No. 60/719,952, filed Sep. 22, 2005, the contents of which are incorporated by reference in their entirety.

STATEMENT REGARDING FEDERALLY SPONSORED RESEARCH OR DEVELOPMENT

This invention was made with U.S. Government support under National Institutes of Health grant numbers AI51903 and AI58724. The U.S. Government may have certain rights in this invention.

TECHNICAL FIELD

The present invention relates to the fields of immunology and medicine. More particularly, the invention relates to methods of producing glycosylated antigens useful in eliciting effective immune responses and vaccination strategies using such antigens.

BACKGROUND OF THE INVENTION

Complex carbohydrates expressed by some pathogens facilitate the evasion of host immune responses and contribute to the destructive sequelae following infection with organisms such as *Streptococcus pneumoniae, Neisseria meingititidis, Haemophilus influenza, Salmonella typhi*, and human immunodeficiency virus ("HIV"). In particular, carbohydrate rich regions of glycoproteins are poorly immunogenic. Factors contributing to this lack of immunogenicity include dilution of single antigenic response due to carbohydrate microheterogeneity and steric interference with highly immunogenic protein epitopes. See, e.g., Rudd, et al., *Crit. Rev. Biochem. Mol. Biol.* 32:1-100 (1997); Woods, et al., *Nature Struct. Biol.* 1:499-501 (1994). Additionally, viruses frequently fool the host immune system by using the cellular glycosylation machinery to express endogenous glycans for which the host is already tolerized.

The role of glycoproteins in HIV pathogenicity, particularly that of gp120, exemplifies the difficulty and importance of complex carbohydrates in eliciting protective host immune responses. HIV, like all viruses, requires the transcriptional and translation machinery of a cell in order to successfully propagate itself in the host. HIV accomplishes this by entering a cell through interactions with specific cellular receptors. Specifically, the HIV virion enters a cell, usually a T lymphocyte, through the interaction of its viral envelope protein ("Env") with the cellular CD4 receptor and the CCR5 cellular coreceptor during early infection, and through the CD4 receptor-CXCR4 coreceptor complex later in infection. See, e.g., Pöhlmann, et al., *J. Virol.* 75:4664-72 (2001); Teunis, et al., *Cell* 100:587-97 (2000). The Env protein is a glycoprotein known as gp120. On the surface of the HIV virion, three molecules of gp120 are noncovalently linked to another cell surface protein, gp41. See, e.g., Zolla-Pazner, *Nature Rev. Immunol.* 4:199-210 (2004). gp41 is a transmembrane glycoprotein found as a homotrimeric complex in the viral envelope. This gp120-gp41 complex forms hetero-oligomeric spikes on the HIV virion that first binds the CD4/coreceptor complex and then subsequently undergoes a conformational change resulting in the exposure of the viral fusion peptide that mediates the entry of the virus into the cell.

Recent evidence suggests that a second interaction distinct from the CD4/coreceptor interaction is also critical to HIV transmission and infection, particularly at the earliest stages. Dendritic cells (DCs), a highly specialized antigen presenting cell, is the first cell targeted by HIV upon infection. See Geijtenbeek, et al., *Cell* 100:587-97 (2000). DCs at the mucosa capture, internalize, and transport HIV from the mucosal surfaces to remote lymph nodes via an interaction between gp120 and DC-SIGN, a cell surface molecule on DCs. The delivery of intact virus by the DCs then results in the infection of $CD4^+$ T-lymphocytes. See Bashirova, et al., *J. Exp. Med.* 193:671-78 (2001). In other words, DC-SIGN acts in trans to mediate efficient infection of CD4+ cells by HIV. See Pöhlmann, et al., *J. Virol.* 75:4664-72 (2001). Later studies showed that DC-SIGN also acts in cis to promote efficient viral infection. See, e.g., Lee, et al., *J. Virol.* 75:12028-38 (2001).

Given the difficulty in eliminating infected cells, an immune response is likely to be most effective if the elicited response impedes the entry of the virus into the cell. To date, attempts to elicit such protective responses have been hampered by the poor immunogenicity of gp120. gp120 contains extensive glycosylation and highly variable loops interspersed with more conserved, functionally constrained regions acting as physical shields for critical gp120 epitopes, i.e., those epitopes that interact with the receptor/coreceptor complex, from antibodies that can block viral entry or neutralize the virus. See, e.g., Garber, et al., *Lancet Infect. Dis.* 4:397-413 (2004). However, naturally elicited neutralizing antibodies have been identified, confirming the potential for effective neutralizing responses. See, e.g., Burton, et al., *Nature Immunol.* 5:233-36 (2004).

Development of HIV/AIDS vaccine to induce neutralizing antibodies against a broad spectrum of HIV-1 primary isolates is still a highly challenging endeavor, 25 years after the discovery of AIDS. The challenge for developing effective vaccines lies in the identification of appropriate antigenic epitopes that can be presented immunogenically such that neutralizing antibodies are elicited in the host. The challenge in developing successful HIV vaccines is further complicated by an expansive diversity in primary HIV isolates. See, e.g., Gaschen, et al., *Science* 296:2354-60 (2002). To date, traditional approaches to vaccine design have not proven successful in eliciting neutralizing antibody responses. Among the approximately 30 clinical trials of HIV vaccines, none are able to induce broadly neutralizing antibodies. One of the major challenges is the lack of an appropriate design of an antigen with neutralizing epitopes that are exposed on the surface of the antigen and highly conserved in most or all subtypes of HIV-1. Pantophlet R et al., *Annu Rev Immunol.* 24:739-69, 2006. Up to date only four monoclonal antibodies (MAbs) with broad and potent neutralizing activity were isolated from HIV-1 infected humans. Douek D C et al., *Cell* 124:677-81 (2006). None of them can be duplicated in all tested species of animals. Among the four MAbs, one targets a conformational epitope on the HIV-1 env gp120, two recognize gp41, and one, 2G12, binds to the high mannose-type carbohydrates on gp120.

The earliest target cell for HIV infection is the dendritic cell (DC), and therefore the most potent vaccine is one that disrupts the ability of HIV to target DCs in a host. The high mannose oligosaccharides of gp120 provide epitopes essential for HIV-DC interaction, and thus provide suitable vaccine targets. High mannose oligosaccharides mediate the interaction between DC-SIGN and gp120. See Geijtenbeek, et al., *Cell* 100:587-97 (2000). Yet, the naturally occurring gp120 only expresses about 20% Man$_8$GlcNAc$_2$ (Man8) and 10% Man$_9$GlcNAc$_2$ (Man9). See Scalan, et al., *J. Virol.* 76:7306-21 (2002). Cyanovirin-N(CV-N), a cyanobacterial protein, binds to high mannose oligosaccharides of gp120, specifically recognizing the Manα1,2-Man structures on Man$_9$GlcNAc$_2$ (Man$_9$) and the D1 D3 isomer of Man$_8$GlcNAc$_2$ (Man$_8$), and through this interaction acts as a potent microbicide against HIV. See Bewley, et al., *J. Am. Chem. Soc.* 123:3982-902 (2001); Sandstrom, et al., *Biochem.* 43:13926-31 (2004). Furthermore, one of the naturally occurring, neutralizing antibodies specifically recognizes a cluster of Manα1,2-Man high mannose oligosaccharides of gp120. See Scanlan, et al., *J. Virol.* 76:7306-21 (2002). This antibody, known as the 2G12 antibody, potently neutralizes a broad range of HIV-1 primary isolates by inhibiting the HIV virion interaction with DCs and CD4+ T cells. See, e.g., Trkola, et al., *J. Virol.* 70:1100-08 (1996); Sanders, et al., *J. Virol.* 76:7293-305 (2002).

High Mannose Type Glycans as a Target for HIV-1 Vaccine

Development of a carbohydrate-based HIV vaccine is considered to be one of the novel approaches for a prophylactic vaccine. Wang, *Curr Opin Drug Discov Devel.* 9(2):194-206, 2006. Several lines of evidence have demonstrated that the terminal Manα1,2-Man structures (α1,2-linked mannose) found on the D1 and D3 arm of Man$_8$NAcGlc$_2$ present novel targets on the gp120 glycoprotein, with the possibility of inducing potent, neutralizing antibodies against HIV-1 from different strains and subtypes.

High-mannose glycans on gp120 are recognized by the broadly neutralizing MAb 2G12. Among the hundreds of MAbs against gp120 that have been generated in rodents and isolated from HIV-1 infected humans, 2G12 is the only one that recognizes virus carbohydrates and potently neutralizes a broad range of HIV-1 primary isolates. It does so by inhibiting the interactions of HIV-1 with DCs and CD4+ T cells. Trkola et al., *J. Virol.* 70(2):1100-8, 1996; Scanlan et al., *J. Virol.* 76(14):7306-21, 2002; Sanders et al, *J. Virol.* 76(14):7293-305, 2002; The binding site of 2G12 has been identified as high mannose-type glycans on the HIV-1 env gp120 glycoprotein. More specifically, the 2G12 MAb binds to a cluster of terminal α1,2-linked mannose residues from at least three high-mannose glycans (Scanlan et al., *J. Virol.* 76(14):7306-21, 2002); it does not recognize other carbohydrates or mannose residues with different terminal linkages, α1,3-linked or α1,6-linked mannose.

The Manα1,2-Man structures on high-mannose glycans are also the binding sites for a potent HIV-1 inhibitor. The cyanobacterial protein termed Cyanovirin-N(CV-N) can inactivate a diverse array of laboratory strains and primary isolates of HIV-1, HIV-2 and SIV. Boyd et al., *Antimicrob Agents Chemother.* 41(7):1521-30, 1997. The protein can also block HIV-1 gp120 interaction with CD4 and coreceptors, prevent virus-to-cell fusion, and stop infection of cells. Esser et al., *J. Virol.* 73(5):4360-71, 1999. Dey et al., *J. Virol.* 74(10):4562-9 2000. These potent properties of CV-N are attributed to its ability to bind with extremely high affinity to the high-mannose oligosaccharides on gp120. Specifically, the inhibitor recognizes the Manα1,2-Man structures on Man$_9$GlcNAc$_2$ (Man9) and the D1 D3 isomer of Man$_8$GlcNAc$_2$ (Man8), but not other forms of high mannoses, including Man7, Man6, and Man5. Bewley et al., *J Am Chem. Soc.* 123(17):3892-902.2001; Sandstrom et al., *Biochemistry.* 43(44):13926-13931 2004. This ability of CV-N to inhibit HIV infection presents evidence of the potency of such molecules that are able to bind to these terminal glycan structures.

Dendritic cells have been shown to enhance infection through the interaction of DC-SIGN with the high-mannose glycans on gp120. Recently, DCs were found to be the first cell type targeted by HIV in the body. DCs at the mucosa are found to capture, internalize and transport HIV to remote lymph nodes where they deliver the intact virus to CD4+ T-lymphocytes. Geijtenbeek et al., *Cell.* 100:587-97, 2000. It was found that all tested strains of HIV-1, HIV-2, SIV and SHIV bind to DCs, with DC-SIGN playing an important role in this process. Pohlmann, et al., *J. Virol.* 75(10):4664-72, 2001. The interaction between HIV and DC-SIGN is mediated by the high-mannose glycans on gp120. Geijtenbeek et al., *Cell.* 100:587-97, 2000. In fact, synthetic high mannose oligosaccharides are able to bind DC-SIGN and prevent subsequent HIV interactions. Feinberg et al., *Science.* 294(5549):2163-6, 2001.

The gp120 protein of HIV-1 is heavily glycosylated and contains an average of 25 N-linked glycosylation sites. Approximately half of them are occupied by high mannose-type or hybrid-type glycans (Leonard et al., *J Biol. Chem.* 265(18): 10373-82, 1990), with the high mannose glycans interacting with 2G12, CV-N, and DC-SIGN through different binding sites. MAb 2G12 binds a cluster of D1 arms from at least three Man9 or Man8 residues, CV-N binds with a high affinity to the D1 and D3 arms from a single Man9 and Man8 residues, and DC-SIGN binds several mannoses residues through its tetramer.

Altogether, these results indicate the strong possibility of inhibiting an early stage of HIV infection with highly specific neutralization antibodies against the Manα1,2-Man structures found on high mannose glycans. The major challenge is to develop an antigen containing strictly high mannoses with terminal α1,2-linked mannose structures, and eliciting an immunogenic response to this epitope that can cross-react to gp120.

Two approaches have taken to construct homogenous HIV-1 glycopeptides for establishing glycopeptide-based HIV vaccines. Wang, *Curr. Opin. Drug Discov. Devel.* 9(2): 194-206, 2006. These approaches are total chemical synthesis of HIV-1 gp120 glycopeptides carrying either a hybrid-type or a high-mannose-type N-glycan, and chemoenzymatic approach to construct various HIV-1 glycopeptides. See Mandal et al., *Angew. Chem. Int. Ed.* 43:2557-2561, 2004; and Geng et al., *Angew. Chem. Int. Ed.* 43:2562-2565, 2004; Singh et al., *Bioorg. Med. Chem. Lett.* 13:327-330, 2003; Wang et al., *ChemBioChem.* 6:1068-1074 (2005); Zeng et al., *J. Am. Chem. Soc.* 127:9692-9693, 2005; Li et al., *J. Org. Chem.* 70:9990-9996, 2005. However, these synthetic glycopeptides need to be further evaluated for their immunogenicity in animal models.

SUMMARY OF THE INVENTION

An effective HIV vaccine capable of eliciting neutralizing antibodies to a broad spectrum of viral isolates is the best hope for controlling the HIV pandemic. Unfortunately, major obstacles continue to hinder the development of such a vaccine, including poor immunogenicity of the Env glycoprotein, viral antigen diversity and immune escape. In response to these challenges, the compositions provided herein offer a distinct recombinant antigen equipped with multiple complex carbohydrate epitopes critical for HIV entry into host cells. The increased number of carbohydrate epitopes maximizes the immunogenicity of these epitopes and its relative potency in a vaccine composition to elicit neutralizing antibodies.

For example, the gp120 provided herein expresses essentially uniform mannose oligosaccharides with a terminal α1-2 glycan, e.g., mannose-9-N-acetylglucosamine-2 ("$Man_9GlcNAc_2$") or $Man_8GlcNAc$. The methods of making the high mannose gp120 compositions and using the resulting compositions to elicit effective anti-HIV neutralizing antibody responses are also described herein.

Therefore, provided herein is an essentially uniformly glycosylated recombinant protein, wherein the terminal glycan is a terminal α1-2 glycan structure. The recombinant protein can be obtained by the transformation of *Saccharomyces cerevisiae* variants with a nucleotide sequence that encodes the protein, fermentation of the transformed cells, and isolation of the protein from the cells or culture supernatant. In some embodiments, the protein is a virulence factor. The protein can be a viral protein. In a specific embodiment, the viral protein is a surface protein. In one embodiment, the protein is gp120 of the human immunodeficiency virus. The terminal glycan can be mannose. In some embodiments, the glycan is oligomannose. In some embodiments, the terminal α1-2 structure is on $Man_9GlcNAc_2$ or $Man_8GlcNAc_2$, or a combination.

Further provided herein is a method of preparing a uniformly glycosylated recombinant protein, wherein the terminal glycan is a terminal α1-2 glycan structure, comprising: a) providing a vector comprising a nucleotide sequence encoding the protein; b) transforming a cell with a defect in protein glycosylation; c) fermenting the transformed cells; and d) purifying the secreted recombinant protein from the cell supernatant. In some embodiments, the nucleotide sequence encodes a protein that is glycosylated in its native state. The nucleotide sequence can encode a protein that is a virulence factor. In a specific embodiment, the nucleotide sequence encodes the gp120 protein. In some embodiments, the cell expresses the gp120 protein with largely $Man_9GlcNAc_2$ or $Man_8GlcNAc_2$. The cell of the instant method can be a yeast cell such as *S. cerevisiae* mns1Δ or *S. cerevisiae* pmr1Δ. The vector can be YEpL and, in some embodiments, may comprise the GAL1 promoter. In some embodiments, the glycoprotein is purified using a His Tag®.

Also provided herein is a method of preparing an antibody which specifically binds a protein comprising a terminal α1-2 glycan structure, the method comprising immunizing an animal with an effective amount of a composition comprising a recombinant protein made by the method or the protein as disclosed herein. The composition can further comprise an adjuvant, a carrier, or both.

Provided herein is the isolated antibody generated by the method disclosed herein as well as the hybridoma that produces the isolated antibody.

Also provided herein is a composition for eliciting antibodies specific for a protein comprising an epitope recognized by antibody 2G12 in a subject, comprising an isolated glycosylated polypeptide comprising at least two N-linked high mannose oligosaccharides that are recognized by antibody 2G12, and a pharmaceutically acceptable excipient, wherein greater than 50% of the N-linked glycans on the glycosylated polypeptide are the high-mannose oligosaccharides, and wherein the high-mannose oligosaccharides are $Man_9GlcNAc_2$, $Man_8GlcNAc_2$, or a combination thereof.

Further provided herein is a composition for eliciting antibodies specific for a protein having an epitope recognized by antibody 2G12 in a subject, comprising a glycosylated polypeptide isolated from a mutant fungus having disrupted pmr1 gene of *Saccharomyces cerevisiae* or disrupted homolog gene of pmr1 gene of *Saccharomyces cerevisiae*, wherein the glycosylated polypeptide is recognized by antibody 2G12, and a pharmaceutically acceptable excipient.

Further provided herein is a composition for eliciting antibodies specific for a protein having an epitope recognized by antibody 2G12 in a subject, comprising a glycosylated polypeptide isolated from a mutant fungus having disrupted pmr1 and mnn1 genes of *Saccharomyces cerevisiae* or disrupted homolog genes of pmr1 and mnn1 genes of *Saccharomyces cerevisiae*, wherein the glycosylated polypeptide is recognized by antibody 2G12, and a pharmaceutically acceptable excipient.

Further provided herein is a composition for eliciting antibodies specific for a protein having an epitope recognized by antibody 2G12 in a subject, comprising a glycosylated polypeptide isolated from a mutant fungus having disrupted och1 and mnn1 genes, or och1, mnn1, and mnn4 genes of *Saccharomyces cerevisiae* or disrupted homolog genes of och1 and mnn1 genes, or och1, mnn1, and mnn4 genes of *Saccharomyces cerevisiae*, wherein the glycosylated polypeptide is recognized by antibody 2G12, and a pharmaceutically acceptable excipient.

Further provided herein is a method of preparing a composition for eliciting antibodies specific for a protein comprising an epitope recognized by antibody 2G12 in a subject, said method comprising: a) fermenting a mutant fungus, wherein the mutant fungus is mutated to produce a glycosylated polypeptide, wherein the glycosylated polypeptide comprises at least two N-linked high mannose oligosaccharides that are recognized by antibody 2G12, and a pharmaceutically acceptable excipient, wherein greater than 50% of the N-linked glycans on the glycosylated polypeptide are the high-mannose oligosaccharides, and wherein the high-mannose oligosaccharides are $Man_9GlcNAc_2$, $Man_8GlcNAc_2$, or a combination thereof; and b) purifying the glycosylated polypeptide from the mutant fungus cell lysate or supernatant. In some embodiments, the method further comprises a step of formulating the glycosylated polypeptide with a pharmaceutically acceptable excipient. In some embodiments, the mutant fungus is *Saccharomyces cerevisiae* having disrupted och1, mnn1, and mnn4 genes, *Saccharomyces cerevisiae* having disrupted och1 and mnn1 genes, *Saccharomyces cerevisiae* having disrupted pmr1 and mnn1 genes, or *Pichia pastoris* or *Candida albicans* having a disrupted och1 gene.

Further provided herein is a method of preparing a composition for eliciting antibodies specific for a protein comprising an epitope recognized by antibody 2G12 in a subject, said method comprising: a) fermenting a mutant fungus, wherein the mutant fungus has disrupted homolog gene of pmr1 gene of *Saccharomyces cerevisiae*; and b) isolating a glycosylated polypeptide recognized by antibody 2G12 from the mutant fungus cell. The method may further comprises a step of formulating the isolated glycosylated polypeptide with a pharmaceutically acceptably excipient. In some embodiments, the mutant fungus is *Saccharomyces cerevisiae* or *Pichia pastoris*, wherein the pmr1 gene is disrupted. In some embodiments, the mutant fungus has been transformed with a vector comprising a nucleotide sequence encoding the glycosylated polypeptide before step a). In some embodiments, the glycosylated polypeptide is HIV gp120 or a fragment thereof.

Further provided herein is a method of preparing a composition for eliciting antibodies specific for a protein comprising an epitope recognized by antibody 2G12 in a subject, said method comprising: a) fermenting a mutant fungus, wherein the mutant fungus has disrupted homolog genes of pmr1 and mnn1 genes of *Saccharomyces cerevisiae*; and b)

isolating a glycosylated polypeptide recognized by antibody 2G12 from the mutant fungus cell. The method may further comprises a step of formulating the isolated glycosylated polypeptide with a pharmaceutically acceptably excipient. In some embodiments, the mutant fungus is *Saccharomyces cerevisiae*, wherein the pmr1 and mnn1 genes are disrupted. In some embodiments, the mutant fungus has been transformed with a vector comprising a nucleotide sequence encoding the glycosylated polypeptide before step a). In some embodiments, the glycosylated polypeptide is HIV gp120 or a fragment thereof.

Further provided herein is a method of preparing a composition for eliciting antibodies specific for a protein comprising an epitope recognized by antibody 2G12 in a subject, said method comprising: a) fermenting a mutant fungus, wherein the mutant fungus has disrupted homolog genes of och1 and mnn1 genes, or och1, mnn1, and mnn4 genes of *Saccharomyces cerevisiae*; and b) isolating a glycosylated polypeptide recognized by antibody 2G12 from the mutant fungus cell. The method may further comprises a step of formulating the glycosylated polypeptide with a pharmaceutically acceptably excipient. In some embodiments, the mutant fungus is *Saccharomyces cerevisiae* having disrupted och1, mnn1, and mnn4 genes, or *Saccharomyces cerevisiae* having disrupted och1 and mnn1 genes. In some embodiments, the mutant fungus has been transformed with a vector comprising a nucleotide sequence encoding the glycosylated polypeptide before step a). In some embodiments, the glycosylated polypeptide is HIV gp120 or a fragment thereof.

Further provided herein is a mutant fungus cell comprising a polynucleotide comprising a nucleotide sequence encoding gp120 or a fragment thereof comprising at least two N-glycosylation site, wherein the mutant yeast cell is capable of producing the gp120 or the fragment comprising at least two N-linked high mannose oligosaccharides that are recognized by antibody 2G12, wherein the high-mannose oligosaccharides are $Man_9GlcNAc_2$, $Man_8GlcNAc_2$, or a combination thereof. In some embodiments, the mutant fungus is *Saccharomyces cerevisiae* having disrupted och1, mnn1, and mnn4 genes, *Saccharomyces cerevisiae* having disrupted och1 and mnn1 genes, or *Pichia pastoris* or *Candida albicans* having a disrupted och1 gene. In some embodiments, the mutant fungus is *Saccharomyces cerevisiae* having disrupted pmr1 and mnn1 genes. In some embodiments, the mutant fungus is *Saccharomyces cerevisiae* or *Pichia pastoris* having disrupted pmr1 gene.

Further provided herein is a composition comprising a whole cell of a mutant yeast and a pharmaceutically acceptable excipient, wherein the mutant yeast has disrupted pmr1 and mnn1 genes, och1 and mnn1 genes, or och1, mnn1, and mnn4 genes of *Saccharomyces cerevisiae*, or disrupted homolog genes of pmr1 and mnn1 genes, och1 and mnn1 genes, or och1, mnn1, and mnn4 genes of *Saccharomyces cerevisiae.*

Further provided herein is a method of generating antibodies specific for a protein comprising an epitope recognized by antibody 2G12 in a subject, comprising administering to the subject an effective amount of any of the compositions described herein.

Further provided herein is a method of inducing neutralizing antibodies against a pathogen (such as HIV) in a subject, comprising administering to the subject an effective amount of any of the compositions described herein.

Further provided herein is a method of inducing neutralizing antibodies against a pathogen in a subject in need thereof, comprising administering an effective amount of a pharmaceutical composition comprising the protein provided herein or a protein prepared by the method provided herein, and a suitable excipient. In some embodiments, the method further comprises administering an adjuvant. In a specific embodiment, the pathogen is HIV.

Further provided herein is a method of preventing or treating pathogen-induced disease in a subject, comprising administering to the subject an effective amount of any of the compositions described herein.

Further provided herein is a method of preventing or treating pathogen-induced disease in a subject in need thereof, comprising administering an effective amount of a pharmaceutical composition comprising the protein provided herein or a protein prepared by the method provided herein, and a suitable excipient. In some embodiments, the method further comprises administering an adjuvant. In a specific embodiment, the pathogen is HIV. In one embodiment, the protein is gp120. In some embodiments, the pharmaceutical composition further comprises multiple gp120 proteins from different HIV strains.

Further provided is a method for identifying an antibody that specifically binds to N-linked high mannose oligosaccharide, comprising detecting binding of an antibody to a glycosylated polypeptide comprising at least two N-linked high mannose oligosaccharides that are recognized by antibody 2G12, and a pharmaceutically acceptable excipient, wherein greater than 50% of the N-linked glycans on the glycosylated polypeptide are the high-mannose oligosaccharides, and wherein the high-mannose oligosaccharides are $Man_9GlcNAc_2$, $Man_8GlcNAc_2$, or a combination thereof.

Further provided is a method for identifying an antibody that specifically binds to N-linked high mannose oligosaccharide, comprising detecting binding of an antibody to a glycoprotein produced in a mutant fungus having disrupted pmr1 gene of *Saccharomyces cerevisiae* or disrupted homolog gene of pmr1 gene of *Saccharomyces cerevisiae*, wherein the glycoprotein is recognized by antibody 2G12.

Further provided is a method for identifying an antibody that specifically binds to N-linked high mannose oligosaccharide, comprising detecting binding of an antibody to a glycosylated polypeptide produced in a mutant fungus having disrupted pmr1 and mnn1 genes of *Saccharomyces cerevisiae* or disrupted homolog genes of pmr1 and mnn1 genes of *Saccharomyces cerevisiae*, wherein the glycoprotein is recognized by antibody 2G12.

Further provided is a method for identifying an antibody that specifically binds to N-linked high mannose oligosaccharide, comprising detecting binding of an antibody to a glycosylated polypeptide produced in a mutant fungus having disrupted och1 and mnn1 genes, or och1, mnn1, and mnn4 genes of *Saccharomyces cerevisiae* or disrupted homolog genes of och1 and mnn1 genes, or och1, mnn1, and mnn4 genes of *Saccharomyces cerevisiae*, wherein the glycoprotein is recognized by antibody 2G12.

In some embodiments, the antibody is in a serum of a subject infected by HIV. In some embodiments, the glycosylated polypeptide is in a mutant yeast cell lysate.

Further provided is a method of identifying a neutralizing monoclonal antibody for HIV transmission, comprising: a) contacting a first cell, wherein the first cell expresses dendritic cell-specific C-type lectin (DC-SIGN), with a second cell expressing CD4+ and CCR5+, b) coculturing the first and second cells with infectious viral particles; c) contacting coculture with a candidate antibody; and d) determining relative infectivity, whereby the neutralizing antibody is one that reduces or eliminates relative infectivity of the second cell by infectious viral particles.

BRIEF DESCRIPTION OF THE DRAWINGS

FIG. 4 shows the antibodies against mannoses. (A) Two rabbits were immunized with 200 μg of zymosan A containing CFA at week 0, and boosted with 100 μg of antigen containing incomplete Freund's adjuvant ("IFA") at weeks 2 and 4 and thereafter every 4 weeks. Immune sera were collected at week 5 and 1 week after each booster. Antibodies were tested in duplicate using ELISA in microwell plates coated with zymosan and yeast mannan. The mean antibody titers from two rabbits were presented. (B) Antibodies against mannoses are reactive to some of tested gp120 glycoproteins. Microwell plates were coated with 5 μg/ml of gp120 proteins. (C) This panel shows the comparison of the antigenicity of gp120 proteins from YU2 strain in mammalian cells and in yeast cells tested by anti-mannan antibody.

FIG. 6A shows the expression and purification of ECD recombinant protein of DC-SIGN. Expression and purification of DC-SIGN ECD recombinant protein. The ECD protein was expressed in *E. coli* at 25° C. in the absence (lane 2) and presence of IPTG (lane 3) for 4 h. Inclusion body was isolated (lane 4) and refolded proteins from insoluble fraction was purified using Ni-NTA columns (lanes 5). Proteins were separated onto 12% SDS-PAGE gel and stained with Coomassie blue. 6B shows the ELISA using DC-SIGN and anti-gp120 polyclonal antibody coated microwell plates. HIV-1 gp120 of YU2 strain was used to bind to the coating proteins.

FIG. 9A shows the processes of glycan from $Man_9GlcNAc_2$ to $Man_8GlcNAc_2$ by MNS1 in the ER. Then, proteins with mainly $Man_8GlcNAc_2$ form of high mannose core are transported to Golgi for further processing. FIG. 9B lower box shows the superglycosylation, which is the major (thick arrow) pathway. FIG. 9B right upper box shows the addition of α1,3-Man on the core, which is the minor pathway (thing arrow). When the genes of Och1, Mnn1 and Mnn4 are all deleted, no sugars can be added on the $Man_8GlcNAc_2$ core resulting in an almost homogenous $Man8GlcNAc_2$ type of glycans (FIG. 9C).

FIG. 13 shows identification of the 2G12 reactive glycoprotein. The proteins in the 100 kDa band were subjected to in-gel digestion. Digested peptides were extracted and analyzed using Nano-LC-MS/MS. Analysis was done on a Micromass Q-Tof hybrid quadrupole/time-of-flight mass spectrometer with a nanoelectrospray source. Raw files were processed with ProteinLynx™ software (Waters) and submitted to a MASCOT search. Totally 6 peptides are identified in the yeast protein PST1 (SEQ ID NO:1) in *Saccharomyces cerevisiae* with Accession NP_010340 and 45,749 Da of mass. The bold letters at the N-terminus is the identified signaling peptide. The Bold letters at the C-terminus is the identified GPI anchor signal. Single underlines indicate the identified peptides by mass spectrometry. Highlighted letters are the potential N-linked glycosylation sites.

FIG. 14 shows confirmation of the 2G12 cross-reactive protein by 2D gel. A. Partially purified Yp100 protein was separated by a 2D gel and subjected to Commassie blue staining (A), western blots with 2G12 MAb (B) and anti- PST1 polyclonal antibody raised against a synthetic peptide in rabbits. Although the partially purified Yp100 proteins have contamination by other glycoproteins from yeast but none of them has similar PI as PST1 does.

FIG. 19 shows confirmation of the 2G12 cross-reactive protein in double mutant by immunoblot. Culture supernatant from double mutant was centrifuged and the precipitate was discarded. The supernatant (lane 1) was pre-cleared with agarose (lane 2). Then the sample was incubated with MAb 2G12 for 16 h at 4° C. The immunocomplex was incubated with protein A-agarose for 1 h at room temperature. The sample was centrifuges briefly and the supernatant was used as flow through (lane 3). The protein A-agarose bound immunocomplex was washed twice (lanes 4 and 5). The bound proteins were eluted with SDS sample buffer (lane 6). Then samples were separated on 4-20% gradient gel, and probed with anti-PST1 polyclonal antibody.

FIG. 20 shows PST1 homolog gene among 18 species. The protein sequence of PST1 (NP_010340) and ECM33 (NP_009634) were used to search homolog genes from Homolo-Gene database (release 50.1) of National Center for Biotechnology Information (NCBI). HomoloGene is a system for automated detection of homologs among the annotated genes of several completely sequenced eukaryotic genomes. Currently HomoloGene database contains 165,820 HomoloGene groups from 18 species. The HomoloGene of interest is obtained by entering protein Reference Sequence (RefSeq) number at NCBI home page (see worldwide web at ncbi.nlm.nih.gov). Multiple alignment of the HomoloGene was performed by clustalw program. PST1 and 3 homolog genes (Proteins of S. pombe and E. gossypii were obtained from HomeloGene database searching. Protein from Candida glabrata was obtained using blastp searching against NCBI nr sequence database).

FIG. 22 shows whole-Cell ELISA. ELISA was used to test the specificity of 2G12 and α1,3-linked mannose antibodies against whole-cell yeast. INVSc1 (diploid) and Δmnn1Δmnn4Δoch1-DIP yeast were diluted to $5.0 \times 10^7$ cells/ml in PBS and used to coat ELISA plates. SF162 gp120 and wild-type yeast mannan were diluted to 5 μg/ml in 50 mM carbonate buffer. 2G12 and anti-α1,3-mannose were used at 10 μg/ml for capture with a three-fold serial dilution in blocking buffer. Panel A shows that the anti-α1,3 antibody has a high affinity towards the wild-type cells and mannan, with the triple mutant showing low affinity and SF162 showing no binding. By contrast, Panel B shows that the triple mutant cells and SF162 gp120 respectively have moderate and high affinities towards the 2G12 antibody, which is specific to terminal α1,2-linked mannose residues. Both the wild-type cells and mannan show no binding to 2G12. This experiment was done in duplicate, and the above $OD_{450}$ reading represent the average.

FIG. 33 shows analyses of potential asparagine-linked (N-linked) and O-linked glycosylation sites of PST1. Panel A shows the amino acid sequence of precursor (SEQ ID NO:2). Bold letters at the N-terminus is the identified signaling peptide. The Bold letters at the C-terminus is the identified GPI anchor signal. Single underlines indicate the identified peptides by mass spectrometry, while double underlines indicate the peptides were identified twice in the same or different mass spectrometry analyses. Highlighted letters are the potential N-linked glycosylation sites. Panel B shows the analysis of O-linked glycosylation sites using software NetOGlyc 3.1 developed by Center for Biological Sequence Analysis (CBS) at Technical University of Denmark in a public Website at worldwide web at cbs.dtu.dk/services/netoglyc. Julenius K., A. Mølgaard, R. Gupta and S. Brunak. Prediction, conservation analysis and structural characterization of mammalian mucin-type O-glycosylation sites. Glycobiology, 15:153-164, 2005.

FIG. 34 shows analyses of potential N-linked and O-linked glycosylation sites of ECM33. Panel A shows the amino acid sequence of precursor (SEQ ID NO:3). Bold letters at the N-terminus is the identified signaling peptide. The Bold letters at the C-terminus is the identified GPI anchor signal. Single underlines indicate the identified peptides by mass spectrometry, while double underlines indicate the peptides were identified twice in the same or different mass spectrometry analyses. Highlighted letters are the potential N-linked glycosylation sites. Panel B shows the analysis of O-linked glycosylation sites using software NetOGlyc 3.1 developed by Center for Biological Sequence Analysis (CBS) at Technical University of Denmark in a public Website at worldwide web at cbs.dtu.dk/services/netoglyc.

FIG. 35 shows analyses of potential N-linked and O-linked glycosylation sites of GP38. Panel A shows the amino acid sequence of precursor (SEQ ID NO:4). Bold letters at the N-terminus is the identified signaling peptide. Single underlines indicate the identified peptides by mass spectrometry, while double underlines indicate the peptides were identified twice in the same or different mass spectrometry analyses. Highlighted letters are the potential N-linked glycosylation sites. Panel B shows the analysis of O-linked glycosylation sites using software NetOGlyc 3.1 developed by Center for Biological Sequence Analysis (CBS) at Technical University of Denmark in a public Website at worldwide web at cbs.dtu.dk/services/netoglyc.

FIG. 36 shows analyses of potential N-linked and O-linked glycosylation sites of YJL171c. Panel A shows the amino acid sequence of precursor (SEQ ID NO:5). Bold letters at the N-terminus is the identified signaling peptide. The Bold letters at the C-terminus is the identified GPI anchor signal. Single underlines indicate the identified peptides by mass spectrometry, while double underlines indicate the peptides were identified twice in the same or different mass spectrometry analyses. Highlighted letters are the potential N-linked glycosylation sites. Panel B shows the analysis of O-linked glycosylation sites using software NetOGlyc 3.1 developed by Center for Biological Sequence Analysis (CBS) at Technical University of Denmark in a public Website at worldwide web at cbs.dtu.dk/services/netoglyc.

FIG. 37 shows analyses of potential N-linked and O-linked glycosylation sites of Gas1. Panel A shows the amino acid sequence of precursor (SEQ ID NO:6). Bold letters at the N-terminus is the identified signaling peptide. Bold letters at the C-terminus is the identified GPI anchor signal. Single underlines indicate the identified peptides by mass spectrometry, while double underlines indicate the peptides were identified twice in the same or different mass spectrometry analyses. Highlighted letters are the potential N-linked glycosylation sites. Panel B shows the analysis of O-linked glycosylation sites using software NetOGlyc 3.1 developed by Center for Biological Sequence Analysis (CBS) at Technical University of Denmark in a public Website at worldwide web at cbs.dtu.dk/services/netoglyc.

FIG. 38 shows analyses of potential N-linked and O-linked glycosylation sites of Gas5. Panel A shows the amino acid sequence of precursor (SEQ ID NO:7). Bold letters at the N-terminus is the identified signaling peptide. Bold letters at the C-terminus is the identified GPI anchor signal. Single underlines indicate the identified peptides by mass spectrometry, while double underlines indicate the peptides were identified twice in the same or different mass spectrometry analyses. Highlighted letters are the potential N-linked glycosylation sites. Panel B shows the analysis of O-linked glycosylation sites using software NetOGlyc 3.1 developed by Center for Biological Sequence Analysis (CBS) at Technical University of Denmark in a public Website at worldwide web at cbs.dtu.dk/services/netoglyc.

MODES OF CARRYING OUT THE INVENTION

Figure 1:
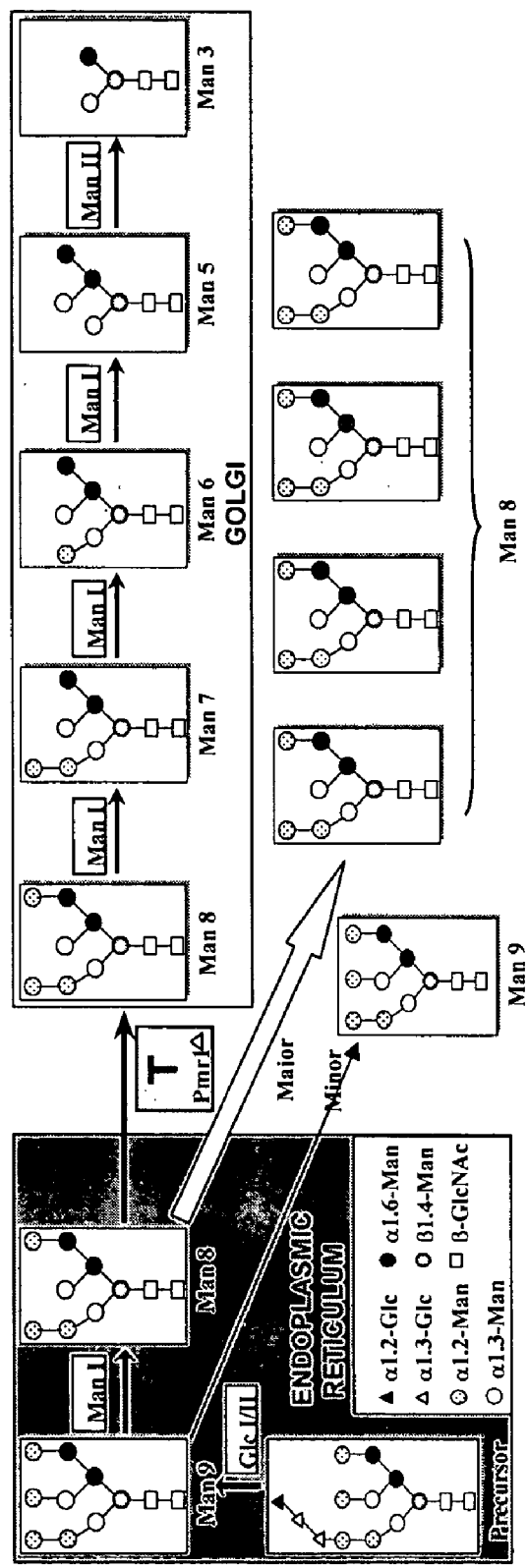
FIG. 1 illustrates the structures and processing of high mannoses in mammalian cells. The left box shows the processes of glycan from precursor to Man8 in the ER. Then, proteins with mainly Man8 are transported to Golgi for further processing (top-right box, an example in mammalian cells). When protein transport from the ER to Golgi is blocked, such as by a mutation of Pmr1 gene in yeast, these glycans will not be further processed resulting in a glycoprotein that contains only Man8 and Man9 forms of glycans (bottom-right).

The ability of CV-N and the 2G12 to inhibit HIV infection suggests that the elicitation of a neutralizing antibody response to Man9, Man8, or both would provide effective immunity against HIV transmission. However, to date there is no reproducible manner in which to provide the gp120 antigen with a specific glycosylation profile. Thus, the recombinant high mannose gp120 composition provided herein provides a potent inducer of protective immunity against HIV infection.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, published patent applications and other publications and sequences from GenBank and other databases referred to herein are incorporated by reference in their entirety. If a definition set forth in this section is contrary to or otherwise inconsistent with a definition set forth in patents, published patent applications and other publications and sequences from GenBank and other data bases that are herein incorporated by reference, the definition set forth in this section prevails over the definition that is incorporated herein by reference.

Other features and advantages of the invention will be apparent from the detailed description, and from the claims.

As used herein, "a" or "an" means "at least one" or "one or more."

As used herein, the term "adjuvant" refers to a substance which, when added to an immunogenic agent, nonspecifically enhances or potentiates an immune response to the agent in the recipient host upon exposure to the mixture. Adjuvants can include, for example, oil-in-water emulsions, water-in-oil emulsions, alum (e.g., aluminum hydroxide/phosphate), liposomes and microparticles. Exemplary adjuvants include, but are not limited to squalene mixtures (SAF-I), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, immunostimulating complexes (ISCOMs), and cytokines. See, e.g., Vogel, et al., *Immunological Adjuvants* IN VACCINES 69-79 (Plotkin, et al., eds., 4th Ed. Saunders (2004)). For veterinary use and for production of antibodies in animals, mitogenic components of Freund's adjuvant (both complete and incomplete) also can be used.

As used herein, "AIDS" refers to the symptomatic phase of HIV infection, and includes both Acquired Immune Deficiency Syndrome (commonly known as AIDS) and AIDS-Related Complex ("ARC"). See, e.g., Kilby, et al., *Natural History of HIV-1 Disease* IN TEXTBOOK OF AIDS MEDICINE 49-58 (Merrigan, et al., eds., Williams & Wilkins 2nd Ed. 1999). The immunological and clinical manifestations of AIDS are well known in the art and include, for example, opportunistic infections and cancers resulting from immune deficiency.

As used herein, the term "antibody" refers to any form of a peptide or polypeptide derived from, modeled after or substantially encoded by, an immunoglobulin gene or immunoglobulin genes, or fragments thereof, capable of specifically binding an antigen or epitope. See, e.g., FUNDAMENTAL IMMUNOLOGY (W. E. Paul, ed., 5th Ed., Lippincott, Williams & Wilkins (2003)); CURRENT PROTOCOLS IN IMMUNOLOGY (Coligan, et al., eds., John Wiley & Sons, most recent edition); ANTIBODY ENGINEERING: A PRACTICAL APPROACH (J. McCafferty, et al., eds., Oxford University Press 1996). Examples of antibody fragments are those that retain antigen-binding and include Fab, Fab', $F(ab')_2$, Fd, and Fv fragments; diabodies; linear antibodies; single-chain antibody molecules, e.g., scFv and $V_{HH}$; minibodies; nanobodies; and multispecific antibodies formed from antibody fragments. Typically, a binding fragment or derivative retains at least 50% of its binding activity. Preferably, a binding fragment or derivative retains at least 60%, 70%, 80%, 90%, 95%, 99% or 100% of its biological activity. The antibody or antigen-binding fragment thereof can include conservative amino acid substitutions that do not substantially alter its binding and/or biologic activity. Thus, the term "antibody" is used in the broadest sense and specifically covers monoclonal (including full length monoclonal antibodies), polyclonal, multispecific (e.g., bispecific), heteroconjugate, chimeric, humanized, human, murine, and synthetic antibodies as well as antibody fragments that specifically bind the desired antigen and exhibit the desired binding and/or biological activity.

The term "antigen" refers to any molecule that is specifically recognized and bound by an antibody. An antigen which elicits an immune response in an organism, as evidenced by production of specific antibodies within the organism is termed an "immunogen." The specific portion of the antigen or immunogen which is bound by the antibody is termed the "binding epitope" or "epitope." An antibody is specific for a particular antigen when it selectively binds the antigen, thereby distinguishing it from other antigens. Preferably, the antibody lacks significant binding to unrelated antigens.

The term "expression cassette" as used herein refers to a nucleotide sequence which is capable of affecting expression of a structural gene (i.e., a protein coding sequence, such as the antibody provided herein) in a host compatible with such sequences. Expression cassettes include at least a promoter operably linked with the polypeptide coding sequence; and, optionally, with other sequences, e.g., transcription termination signals. As used herein, the term "promoter" includes all sequences capable of driving transcription of a coding sequence in a cell, e.g., a mammalian or plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. Promoters can be constitutive or inducible. Additional factors necessary or helpful in effecting expression also may be used, e.g., enhancers. A promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, e.g., enhancers, need not be physically contiguous or located in close proximity to the coding sequences whose transcription they enhance. Expression cassettes also include plasmids, expression vectors, recombinant viruses, any form of recombinant "naked DNA" vector, and the like.

The term "isolated" includes a material removed from its original environment, e.g., the natural environment if it is naturally occurring. For example, an isolated polynucleotide or polypeptide is one that is separated from some or all of the coexisting materials in the natural system. Such polynucleotides could be part of a vector and/or such polynucleotides or polypeptides could be part of a composition, and still be isolated in that such vector or composition is not part of its natural environment.

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded which encodes an antibody of the present invention, or a biologically active fragment thereof. The term encompasses nucleic acids, i.e., oligonucleotides, containing known analogues of natural nucleotides. The term also encompasses nucleic-acid-like structures with synthetic backbones. See e.g., Mata, *Toxicol. Appl. Pharmacol.* 144:189-97 (1997); Strauss-Soukup, *Biochemistry* 36:8692-98 (1997); and Samstag, *Antisense Nucleic Acid Drug Dev* 6:153-56 (1996).

"Recombinant" polypeptides or proteins refer to polypeptides or proteins produced by recombinant DNA techniques; e.g., produced from cells transformed by an exogenous DNA construct encoding the desired polypeptide or protein. See, e.g., CURRENT PROTOCOLS IN MOLECULAR BIOLOGY (F. M. Ausebel, et al., eds., John Wiley & Sons, most current edition).

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

The term "homolog" is used to refer a gene or a product of a gene from one species that has a common origin and functions the same as a gene from another species. For example, a fungus homolog gene of pmr1 gene of *S. cerevisiae* refers to a fungus gene that has a common origin and encodes a protein that has the same function as the pmr1 gene of *S. cerevisiae*.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.).

As used herein, the term "synergize" refers to the ability of one agent to increase the anti-pathogenic or neutralizing effect of a second agent. Synergistic activity, thus, includes but is not limited to an increased biological effect (e.g., more potent or longer lasting) using the two agents together that is not observed when the agents are used separately, a more effective biological effect, e.g., elimination of multiple types of toxicity not achievable with the administration of a single agent, or a reduction in the amount of agents necessary for administration to achieve the biological effect observed with a single agent.

The term "pathogen" refers to any organism that induces or elicits a undesired symptom or disease state. A pathogen may be a bacteria, virus, or fungus.

As employed herein, the term "subject" embraces human as well as other animal species, such as, for example, canine, feline, bovine, porcine, rodent, and the like. It will be understood by the skilled practitioner that the subject having a pathogen or disease targeted by the antibody of the invention.

As used herein, the term "ameliorating, treating or preventing" include a postponement of one or more symptoms associated with the infection or other disorder, a reduction in the severity of such symptoms that will or are expected to develop, or a complete elimination of such symptoms. These terms further include ameliorating existing pathogen-related symptoms, reducing duration of disease, preventing additional symptoms, ameliorating or preventing serious sequelae, preventing or reversing mortality, and reducing or preventing pathogen transmission. Thus, the terms denote that a beneficial result has been conferred on a subject with a pathogen, or with the potential of exposure to such a pathogen. In particular, ameliorating, treating or preventing include, e.g., preventing initial infection of an individual exposed to HIV; reducing viral burden in an individual infected with HIV; prolonging the asymptomatic phase of HIV infection; increasing overall health or quality of life in an individual with AIDS; and prolonging life expectancy of an individual with AIDS. A clinician can compare the effect of immunization with the patient's condition prior to treatment, or with the expected condition of an untreated patient, to determine whether the treatment is effective in inhibiting AIDS.

As used herein, an "effective amount" is an amount sufficient to inhibit or prevent, partially or totally, transmission of the pathogen, tissue damage or other symptoms associated with the action of the virulence factor within or on the body of the subject or to prevent or reduce the further progression of such symptoms. When applied to an individual active ingredient administered alone, an effective dose refers to the dose required for that ingredient alone. When applied to a combination of active agents, an effective dose refers to the combined amounts of the active ingredients that result in the therapeutic effect, whether administered in combination, serially or simultaneously. The term "therapeutically effective amount" and "effective amount" are employed interchangeably.

As used herein, the term "bioactive agent" refers to any synthetic or naturally occurring compound that enhances or mediates a desired biological effect to reduce or eliminate the infectivity or pathogenicity of a particular organism. Bioactive agents include, for example, a pharmaceutical agent, such as a chemotherapeutic drug, a microbicidal drug, a antiviral drug, a toxin, a cytokine, a ligand, an antibody, or some combination thereof.

As used herein, "prevents the productive interaction" means that the amount of interaction is reduced as compared to the amount that would occur without the antibody or biologically active fragment thereof. The interactions may be reduced or prevented by any means including, but not limited to masking or altering interactive regions on the virulence factor, and altering the expression, aggregation, conformation, or association state of the virulence factor.

As used herein, the term "treat" refers to the application or administration of a therapeutic agent to a subject, or application or administration of a therapeutic agent to an isolated tissue or cell line from a subject, who has a disease or disorder, a symptom of disease or disorder or a predisposition toward a disease or disorder, with the purpose of curing, healing, alleviating, relieving, altering, remedying, ameliorating, improving or affecting the disease or disorder.

B. Compositions

Provided herein is a uniformly glycosylated recombinant protein, wherein the terminal sugar is a terminal α1-2-Mannose structure. The recombinant protein can be obtained by the transformation of *Saccharomyces cerevisiae* variant with a nucleotide sequence that encodes the protein, fermentation of the transformed cells, and isolation of the protein from the cells or culture supernatant. In some embodiments, the protein is a virulence factor. The protein can be a viral protein. In a specific embodiment, the viral protein is a surface protein. In one embodiment, the protein is gp120 of the human immunodeficiency virus. In some embodiments, the glycan is oligomannose. In one embodiment, the terminal α1-2-Mannose structures are on $Man_9GlcNAc_2$ or $Man_8GlcNAc_2$.

Any suitable virulence factor may be employed in the composition disclosed herein. A virulence factor is any glycoprotein that mediates or participates in the ability of a microorganism to cause disease in a host under suitable conditions. For example, a virulence factor can be an adherence factor, a coat protein, an invasion factor, a capsule, an exotoxin, or an endotoxin. Exemplary organisms expressing glycoprotein virulence factors include, but are not limited to lentiviruses (e.g., HIV), ebola virus, gram negative bacteria (e.g., *Campylobacter jejuni, Campylobacter coli, Neisseria nieningitidis, Helicobacter pylori, Escherichia coli, Haemophilus, influenzae, Pseudomonas aeruginosa, Mycobacteria tuberculosis, Mycobacteria bovis, Borrelia burgdorferi, Chlaniydia* spp., and *Streptococcus parasanguis*).

The glycosylation of the protein virulence factor can be N-linked or O-linked. A glycan is a polysaccharide consisting of more than about five monosaccharide residues joined to one another by glycosidic linkages. Representative glycans include mannose. Essentially uniform glycosylation of the protein virulence factor refers to greater than 70%, 80%, 90% or 100% glycosylation with a single glycoform.

In one aspect, the composition provided herein is a gp120 essentially uniformly glycosylated with $Man_9GlcNAc_2$, $Man_8GlcNAc_2$, or some combination thereof, having a terminal α1-2-Man structure. As used herein, the term "essentially uniformly" refers to greater than 70% of the glycans on gp120 are $Man_9GlcNAc_2$, $Man_8GlcNAc_2$, or some combination thereof. In a specific embodiment, the glycosylated gp120 composition provided herein has greater than 90% $Man_9GlcNAc_2$ or $Man_8GlcNAc_2$, preferably 100% $Man_9GlcNAc_2$ or $Man_8GlcNAc_2$. The term "high mannose" refers to a glycan of 5 to 9 mannose residues without other kinds of terminal sugars. See, e.g., FIG. 1. Mammalian cell surface and serum glycoproteins rarely contain terminal mannose residues. See, e.g., Weis, et al., *Immunol Rev.* 163:19-34 (1998). Mammalian glycoproteins contain mostly complex-type oligosaccharides with few Man5 or Man6, while HIV-1 gp120 proteins contain a larger number of Man7-9, indicating that the high mannoses on HIV-1 virus and human glycoproteins are significantly different in quantity and quality. See, e.g., Scanlan, et al., *J. Virol.* 76:7306-21 (2002); Cutalo, et al., *J Am Soc Mass Spectrom.* 15:1545-55 (2000).

Also provided herein is a composition comprising an isolated glycosylated polypeptide comprising at least two N-linked high mannose oligosaccharides that are recognized by antibody 2G12, and a pharmaceutically acceptable excipient, wherein greater than 50% of the N-linked glycans on the glycosylated polypeptide are the high-mannose oligosaccharides, and wherein the high-mannose oligosaccharides are $Man_9GlcNAc_2$, $Man_8GlcNAc_2$, or a combination thereof.

Further provided herein is a composition comprising a glycosylated polypeptide isolated from a mutant fungus having disrupted pmr1 gene of *Saccharomyces cerevisiae* or disrupted homolog gene of pmr1 gene of *Saccharomyces cerevisiae*, wherein the glycosylated polypeptide is recognized by antibody 2G12.

Further provided herein is a composition comprising a glycosylated polypeptide isolated from a mutant fungus having disrupted pmr1 and mnn1 genes of *Saccharomyces cerevisiae* or disrupted homolog genes of pmr1 and mnn1 genes of *Saccharomyces cerevisiae*, wherein the glycosylated polypeptide is recognized by antibody 2G12.

Further provided herein is a composition comprising a glycosylated polypeptide isolated from a mutant fungus having disrupted any combination of och1, mnn1, and/or mnn4 genes of *Saccharomyces cerevisiae* or disrupted any combination of the homolog genes of och1, mnn1, and/or mnn4 genes of *Saccharomyces cerevisiae*, wherein the glycosylated polypeptide is recognized by antibody 2G12.

The glycosylated polypeptide may comprise at least three, at least four, at least five, at least six, at least seven, at least eight, at least nine, or at least ten N-linked high-mannose oligosaccharides. The glycosylated polypeptide may be a fungus (such as a yeast) or a non-fungus glycoprotein or a fragment thereof. For example, the glycosylated polypeptide is PST1, ECM33, Gas1, Gas5, GP38, or YJL171c of *S. cerevisiae*, or a homolog of any of these proteins. The glycosylated polypeptide may be a virulence factor. In some embodiments, the glycosylated polypeptide is a viral protein or a fragment thereof. In some embodiments, the glycosylated polypeptide is HIV gp120 or a fragment thereof.

In some embodiments, at least 50%, at least 60%, at least 70%, at least 80%, at least 90 percent, or at least 95% of the N-linked glycans on the glycopeptide are $Man_9GlcNAc_2$, $Man_8GlcNAc_2$, or a combination thereof.

The compositions of the present invention exclude any of the glycosylated polypeptides described in Wang, *Curr. Opin. Drug Discov. Devel.* 9(2):194-206, 2006; Mandal et al., *Angew. Chem. Int. Ed.* 43:2557-2561, 2004; Geng et al., *Angew. Chem. Int. Ed.* 43:2562-2565, 2004; Singh et al., *Bioorg. Med. Chem. Lett.* 13:327-330, 2003; Wang et al., *ChemBioChem.* 6:1068-1074 (2005); Zeng et al., *J. Am. Chem. Soc.* 127:9692-9693, 2005; and Li et al., *J. Org. Chem.* 70:9990-9996, 2005.

Further provided herein is a composition comprising a whole cell of a mutant yeast and a pharmaceutically acceptable excipient, wherein the mutant yeast has disrupted pmr1 and mnn1 genes, och1 and mnn1 genes, or och1, mnn1, and mnn4 genes of *Saccharomyces cerevisiae*, or disrupted homolog genes of pmr1 and mnn1 genes, och1 and mnn1 genes, or och1, mnn1, and mnn4 genes of *Saccharomyces cerevisiae*. The yeast whole cell may be alive or killed. The composition may be used for therapeutic or preventive vaccine (e.g., vaccine for HIV).

The composition described here comprises a pharmaceutically acceptable excipient. Any pharmaceutically acceptable carriers, excipients, or stabilizers (*Remington: The Science and Practice of Pharmacy* 20th Ed. (2000) Lippincott Williams and Wilkins, Ed. K. E. Hoover.), in the form of lyophilized formulations or aqueous solutions may be used. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONIC® or polyethylene glycol (PEG). In some embodiments, the pharmaceutically acceptable excipient is an adjuvant. The compositions comprising adjuvant may be used vaccines.

Further provided herein is a method of preparing a uniformly glycosylated recombinant protein, wherein the terminal glycan is a terminal α1-2-Man structure, comprising: a) providing a vector comprising a nucleotide sequence encoding the protein; b) transforming a cell with a defect in protein glycosylation; c) fermenting the transformed cells; and d) purifying the secreted recombinant protein from the cell supernatant. In some embodiments, the nucleotide sequence encodes a protein that is glycosylated in its native state. The nucleotide sequence can encode a protein that is a virulence factor. In some embodiments, the mutated cell expresses glycoproteins with largely $Man_9GlcNAc_2$ or $Man_8GlcNAc_2$. In a specific embodiment, the nucleotide sequence encodes the gp120 protein. In some embodiments, the cell expresses the gp120 protein with largely $Man_9GlcNAc_2$ or $Man_8GlcNAc_2$. The cell of the instant method can be a yeast cell such as *S. cerevisiae* mns1Δ or *S. cerevisiae* pmr1Δ. The vector can be YEpL and, in some embodiments, may comprise the GAL1 promoter. In some embodiments, the glycoprotein is purified using a His Tag®.

Further provided herein is a method for preparing any of the compositions described herein by fermenting a mutant fungus, wherein the mutant fungus is mutated to produce the glycosylated polypeptide; isolating or purifying the glycosylated polypeptide; and combining the polypeptide with a pharmaceutically acceptable excipient to form the composition. The compositions comprising the whole yeast cells may be prepared by fermenting a mutant yeast; preparing whole yeast cell with a pharmaceutically acceptable excipient to form the composition.

Any suitable cell may be employed. Preferably, the cell has a defect that permits truncates or otherwise modulates the typical intracellular processing of glycans. In some embodiments, the cell is a fungus cell (e.g., a yeast or a mold cell). In a specific embodiment, the cell is a yeast cell. See, e.g., U.S. Pat. Nos. 5,919,651; 5,705,616. The outer chain glycosylation of secreted yeast proteins is a high (or long) mannose type oligosaccharide chain. Thus, yeast production provides heterologous proteins with this yeast-specific outer chain glycosylation of the high mannose type, which is sometimes denoted "hyperglycosylation." Briefly, the O-glycosidic carbohydrate structures of yeast proteins consist of an unbranched mannose chain of 1-5 mannose residues. O-glycosylation begins in the ER (transfer of the first mannose residue) and is completed in the Golgi apparatus. N-glycosylation begins with a core unit of N-acetylglucosamine, mannose and glucose being built up on a lipid carrier intermediate that is subsequently transferred to asparagine (Asn) residues of proteins in the endoplasmic reticulum. The protein-bound core unit then is cleavage at specific glucose and mannose residues followed by elongation of the polysaccharide in the Golgi apparatus to result in "outer chain" glycosylation.

A number of yeast strains can be employed to produce the composition provided herein. The cells of *Saccharomyces cerevisiae* are typically used, but those of *Pichia pastoris* and *Schizosaccharomyces pombe* are also commercially available for production of heterologous proteins. See, e.g., Tuite, et al., *Expressing Cloned Genes in the Yeasts Saccharomyces cerevisiae* and *Pichia pastoris* IN PROTEIN EXPRESSION: A PRACTICAL APPROACH 61-100 (Higgins, et al., eds., Oxford University Press 1999); Hitzeman, et al., *Methods Enzymol.* 185:421-440 (1990); Barr, et al., *Vaccine* 5:90-101 (1987); Liu, et al., *Clin. Diagn. Lab. Immunol.* 5:592-94 (1998). Yeast strains with defects in Mns1p or Pmr1p are useful. Msn1p is an α1,2 mannosidase that localizes in the ER where it trims Man9 to a single isomer of Man8 by removing the central arm of α1,2-linked mannose. Therefore, the *S. cerevisiae* mns1p mutant strain Mns1Δ produces proteins glycosylated only with Man9. The protein Pmr1p is a calcium-dependent ATPase important for the transport of $Ca^{++}$ from the ER to the Golgi. See Herscovics, *Biochim. Biophys. Acta* 1426:275-85 (1999); Camirand, et al., *J. Biol. Chem.* 266:15120-27 (1991). The *S. cerevisiae* pmr1Δ mutant strain pmr1Δ secretes glycoproteins consisting solely of Man8, trimmed from Man9 by mannosidase I in the ER. See, e.g., Harmsen, et al., *Gene* 125:115-23 (1993). However, any yeast strain with a suitable defect in N-glycosylation may be employed to produce the composition provided herein. See, e.g., U.S. Pat. Nos. 5,705, 616, 5,798,226.

Yeast strains with disrupted pmr1 gene, disrupted pmr1 and mnn1 genes, disrupted och1 genes, disrupted och1 genes in combination with one or more of mnn1, mns1, and mnn4 genes, disrupted och1 and mnn1 genes, or disrupted och1, mnn1, and mnn4 genes of *Saccharomyces cerevisiae*, *Candida albicans* and *Pichia pastoris*, or other yeast strains with disrupted homolog gene(s) may also be used to produce the glycosylated polypeptide or the whole yeast cell compositions.

Methods of generating mutant fungus cells are known in the art. The Examples of the invention provide details of generating several mutant yeast cells. See, e.g., Chiba et al., *J. Biol. Chem.* 273:26298-26304, 1998; Rudolph et al., *Cell* 58:133-145, 1989; Nakanishi-Shindo et al., *J. Biol. Chem.* 268:26338-26345, 1993.

Any suitable vector may be employed to transfect the mutant cells to produce recombinant glycosylated polypeptides. Yeast cells typically employ plasmid-based vectors. The vectors can be autonomous, multicopy plasmids (e.g., YEp or YRp), autonomous, single copy plasmids (e.g., YCp), or integrative (usually single copy) plasmids (e.g., YIp). See, e.g., Yeast Vectors (Unit 13.4) IN CURRENT PROTOCOLS IN MOLECULAR BIOLOGY (Ausebel, et al., eds. John Wiley & Sons, most recent edition). In one embodiment, the vector is YEpL or pYES2-CT. Any promoter known in the art to result in heterologous protein production in the transformed cell may be employed. For yeast cells, natural and engineered promoters are available. Such promoters include, but are not limited to PGK, GAP, TEFI, GAL1, ADH2, PHO5, CUP1, MFα1, TRP1, PAL, GAP/GAL, GAP/ADH2, CYC1/GRE, and PGK/ARE. In one embodiment, the promoter is GAL1. See, e.g., U.S. Pat. No. 5,139,936. The vector may also include additional sequences such as an origin of replication and various tag sequences useful for purification of the heterologous virulence factor, e.g., gp120.

Cells are transformed with the virulence factor-encoding vector and fermented using well known methods in the art. For yeast, cells may be transformed using lithium acetate, spheroplast transformation, or electroporation followed by standard fermentation. See, e.g., *Yeast* (Unit 13) IN CURRENT PROTOCOLS IN MOLECULAR BIOLOGY (Ausebel, et al., eds. John Wiley & Sons, most recent edition).

Exemplary virulence factors include, but are not limited to gp120, ebola virus envelope protein, or other glycosylated viral envelope proteins or viral proteins. See, e.g., U.S. Pat. Nos. 6,630,144; 6,713,069.

In one aspect, any suitable gp120 nucleotide sequence can be employed in the composition provided herein. The gp120 molecule consists of a polypeptide core of 60 kD extensively modified by N-linked glycosylation thereby increasing its apparent molecular weight to 120 kD. See, e.g., Zolla-Pazner, et al., *Nature Rev. Immunol.* 4:199-209 (2004). The amino acid sequence of gp120 contains five relatively conserved domains interspersed with five hypervariable domains. The positions of the 18 cysteine residues in the gp120 primary sequence, and the positions of 13 of the approximately 24 N-linked glycosylation sites in the gp120 sequence are common to all gp120 sequences. See Modrow, et al., *J. Virol.* 61:570-78 (1987). The hypervariable domains contain extensive amino acid substitutions, insertions and deletions. Sequence variations in these domains result in up to 30% overall sequence variability between gp120 molecules from the various viral isolates. See, e.g., Gaschen, et al., *Science* 296:2354-60 (2002). Nonetheless, gp120 sequences maintain the virus's ability to bind to the viral receptor CD4 and DC-SIGN. Exemplary sequences include, but are not limited to those disclosed in Ratner, et al., *Nature* 313:227 (1985); Muesing, et al., *Nature* 313:450-58 (1985); McCutchan, et al., *AIDS Res. Human Retroviruses* 8:1887-95 (1992); Gurgo, et al., *Virol.* 164: 531-36 (1988); and the HIV SEQUENCE COMPENDIUM 1987-PRESENT (Myers, et al., eds., Theoretical Biology and Biophysics Group, Los Alamos National Laboratory, Los Alamos, N. Mex.). Sequences from newly isolated strains also can be employed. See, e.g., Ou, et al, *Science* 256:1165-71 (1992); Zhang, et al., *AIDS* 5:675-81 (1991); and Wolinsky, *Science* 255:1134-37 (1992).

Any suitable purification and glycosylation analysis methods may be employed with the glycosylated polypeptide (such as uniformly glycosylated) provided herein. For example, NP-HPLC of fluorescence labeled N-glycans from recombinant gp120 employs exoglycosidase digestion with HPLC to identify the various forms of glycans. See, e.g., Scalan, et al., *J. Virol.* 76:7306-21 (2002). Alternatively, the expression levels may be determined using flow cytometric analysis, ELISA, or Western blot analysis using glycan specific antibodies like, e.g., the 2G12 antibody. Other exemplary methods include lectin-based assays, rocket affinoelectrophoresis, two-dimensional electrophoresis, fluorophore-assisted carbohydrate electrophoresis (FACE), capillary electrophoresis, nuclear magnetic resonance, mass spectrometry, gas-liquid chromatography with mass spectrometry (GLC/MS), fast atom bombardment (FAB), and electrospray ionization (ESI). See, e.g., Brooks, et al., FUNCTIONAL & MOLECULAR GLYCOBIOLOGY (BIOS Scientific Publishers Ltd 2002).

The glycosylated polypeptides (such as uniformly glycosylated protein) provided herein can also be used in assays for detecting the presence of neutralizing antibodies to the pathogen, e.g., HIV. In such assays, the protein will normally be labeled with one of a variety of labels which find use in assays. These labels have been extensively reported in the patent and technical literature, and include radionuclides, fluorescers, enzymes, enzyme substrates, particles, small molecules, and the like.

The wild type protein serotypes of the virulence factor need not be employed since one or more amino acids may be added, deleted or substituted so long as the relevant binding property, glycosylation sites, and other relevant immunological properties are retained. Thus, at least 90%, usually at least 95%, more usually at least 99% of the amino acids will be the correct amino acids and in the correct sequence. Usually, any changes will be at the N-terminus where from 0 to 5 amino acids may differ.

In one embodiment, the uniformly glycosylated gp120 provided herein displays conformational epitopes which elicit highly neutralizing antibodies capable of neutralizing primary HIV-1 isolates. In some embodiments, the preferred proteins are those which can elicit antibodies which neutralize primary isolates in two or more different clades (e.g., two or more of clades A, B, C, D, and E). Neutralization is determined as disclosed herein.

The invention provides kits comprising any of compositions described herein, e.g., uniformly glycosylated proteins. The kits also can contain instructional material teaching the methodologies and industrial uses of the invention, as described herein.

Specifically provided herein is a compartment kit comprising one or more containers, wherein a first container comprises one or more antibodies engineered by the present methods, and one or more other containers comprising one or more of the following: wash reagents, reagents necessary for administration of the composition or capable of detecting presence of antibody specific for the composition. The containers can be glass, plastic, or strips of plastic or paper. Types of detection agents include labeled secondary antibodies, other labeled secondary binding agents, or in the alternative, if the primary antibody is labeled, the enzymatic, or antibody binding reagents that are capable of reacting with the labeled antibody. Ancillary materials to assist in or to enable performing such a method may be included within a kit provided herein.

C. Vaccines Using Glycosylated Polypeptides or Whole Mutant Yeast Cells

Provided herein is a method of inducing neutralizing antibodies against a pathogen (such as HIV) in a subject, comprising administering to the subject an effective amount of any of the compositions described herein.

Provided herein is a method of inducing neutralizing antibodies against a pathogen in a subject in need thereof, comprising administering an effective amount of a pharmaceutical composition comprising a uniformly glycosylated recombinant protein, wherein the terminal glycan is a terminal $\alpha$1-2 glycan structure or a protein prepared by the method of preparing a uniformly glycosylated recombinant protein, wherein the glycan is oligomannose with a terminal $\alpha$1-2 glycan structure, comprising: a) providing a vector comprising a nucleotide sequence encoding the protein; b) transforming a cell with a defect in protein glycosylation; c) fermenting the transformed cells; and d) purifying the secreted recombinant protein from the cell supernatant as disclosed herein, and a suitable excipient. The method can further comprise administering an adjuvant. In one embodiment, the pathogen is HIV. In a specific embodiment, the uniformly glycosylated recombinant protein is $Man_9GlcNAc_2$ gp120 or $Man_8GlcNAc_2$ gp120.

Also provided herein is a method of preventing or treating pathogen-induced (such as HIV-induced) disease in a subject, comprising administering to the subject an effective amount of any of the compositions described herein.

Also provided herein is a method of preventing or treating pathogen-induced disease in a subject in need thereof, comprising administering an effective amount of a pharmaceutical composition comprising a uniformly glycosylated recombinant protein, wherein the terminal glycan is a terminal $\alpha$1-2 glycan structure or protein prepared by the method of preparing a uniformly glycosylated recombinant protein, wherein the glycan is oligomannose with a terminal α1-2 glycan structure, comprising: a) providing a vector comprising a nucleotide sequence encoding the protein; b) transforming a cell with a defect in protein glycosylation; c) fermenting the transformed cells; and d) purifying the secreted recombinant protein from the cell supernatant as disclosed herein, and a suitable excipient. The method can further comprise administering an adjuvant. In one embodiment, the pathogen is HIV. In a specific embodiment, the uniformly glycosylated recombinant protein is $Man_9GlcNAc_2$ gp120 or $Man_8GlcNAc_2$ gp120.

In some embodiments, the pharmaceutical compositions provided herein further comprises multiple gp120 proteins from different HIV strains.

The vaccine compositions of the invention may be administered by any route clinically indicated, such as by application to the surface of mucosal membranes including, but not limited to intranasal, oral, ocular, gastrointestinal, rectal, vaginal, or genito-urinary routes. Alternatively, parenteral modes of administration such as intravenous, subcutaneous, intraperitoneal, or intramuscular may also be used. In some embodiments, the protein is administered transdermally or transmucosally.

Typically, vaccine protection against HIV infection induces a mucosal immune response, a systemic immune responses, or both. Useful routes for administration can include parenterally or non-parenterally routes, including but not limited to subcutaneous, intracutaneous, intravenously, intramuscular, peroral, mucosal or intranasal administration.

Vaccines according to the present invention may be formulated according to any suitable method known in the art, and may contain any suitable and compatible diluent, carrier, preservative, pharmaceutical excipient or other ingredient. See, e.g., REMINGTON: THE SCIENCE AND PRACTICE OF PHARMACY 20th Ed. (Gennaro et al. (eds.), University of Sciences 2000). Suitable pharmaceutical carriers for administration intravenously, intraperitoneally, intramuscularly, transmucosally (for example intranasally, rectally, vaginally, buccally), transdermally, subcutaneously or any other route of administration are well known in the art and are contemplated for use with the invention. See, e.g., Robinson, et al. (eds.), VACCINE PROTOCOLS 2nd. Ed. (Humana Press 2003); Powell, et al. (eds.), VACCINE DESIGN: THE SUBUNIT AND ADJUVANT APPROACH (Plenum Press 1995); Plotkin, et al. (eds.) VACCINES 4th Ed. (Saunders 2004); U.S. Pat. Nos. 4,235,877; 4,372,945; and 4,474,757. Suitable formulations, which may include an adjuvant, can be determined empirically.

The amounts of vaccine administered depend on the particular vaccine antigen and any adjuvant employed, the mode and frequency of administration, the age and weight of the recipient, and the desired effect (e.g., prophylaxis and/or treatment), as determined by one skilled in the art. The amount of protein in a vaccine dose is selected as an amount which induces an immunoprotective response without significant, adverse side effects in typical vaccines. Such amount will vary depending upon which specific immunogen is employed. Generally, it is expected that each dose will comprise between 1 μg and 100 mg of protein, sometimes between 2-200 μg, and other times 4-40 μg. An optimal amount for a particular vaccine can be ascertained by standard studies involving observation of antibody titers and other responses in subjects.

Administration can repeated as is determined to be necessary by one skilled in the art. In many instances it will be desirable to have multiple administrations of the vaccine, usually not exceeding six vaccinations, more usually not exceeding four vaccinations, and preferably one or more, usually about three vaccinations. The vaccinations will normally be at from 2 to 12 week intervals, more usually from 3 to 5 week intervals, with optional periodic boosters at intervals of 1 to 5 years. The course of the immunization may be followed by assays for antibodies for pathogen, e.g., HIV gp120 antibodies.

The active vaccines of the invention can be used alone or in combination with bioactive agents including but not limited to other relevant virulence factors, attenuated or killed forms of the virus, or adjuvants. Such additional agents can be administered simultaneously or sequentially through the same or a direct route of administration. In some embodiments, the administered proteins originate from different serotypes of the same or related pathogens. In one embodiment, the bioactive agent synergizes with the glycosylated protein provided herein to stimulate an effective immune response against the pathogen.

In some embodiments, glycosylated protein (such as uniformly glycosylated recombinant protein) provided herein is administered with an adjuvant. In the formulation of vaccines for use in the invention it is preferred that the adjuvant composition induces a humoral or Th2 response. Such adjuvants can include those that induce IL-4, IL-6, and/or IL-10 production as well as other means of enhancing the immunogenicity of T-independent antigens. See, e.g., Mond et al., *Annual Reviews* 13:655-92 (1995); Lesinski et al., J. Microbiol. Methods 47:135-49 (2001). However it will be understood that other responses, including cellular responses, are not excluded, particularly if other virulence factors are co-administered in the vaccine regimen. Therefore, well known adjuvants such as CpG oligodeoxynucleotides, tetanus toxoid, saponin, lipopeptide, and IL-12 are also contemplated. In a specific embodiment, the glycosylated protein provided herein is conjugated to stimulatory epitopes of tetanus toxin. See, e.g., Kumat et al., *J. Immunol.* 148:1499-505 (1992).

The proteins provided herein may be delivered in a formulation with an adjuvant or separately from the adjuvant, either simultaneously or sequentially. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatized polysaccharides, or polyphosphazenes. See, e.g., Robinson, et al. (eds.), VACCINE PROTOCOLS 2nd. Ed. (Humana Press 2003); Powell, et al. (eds.), VACCINE DESIGN: THE SUBUNIT AND ADJUVANT APPROACH (Plenum Press 1995); Plotkin, et al. (eds.) VACCINES 4th Ed. (Saunders 2004); U.S. Pat. Nos. 6,797,276; 6,596,278; 6,491,919; 4,894,229; 5,814,321; 5,679,355; and 4,803,070. In some embodiments, the adjuvant. is incomplete Freund's adjuvant (IFA) or alum. The amount of the adjuvant employed can vary widely depending upon the nature of the adjuvant, generally ranging from 0.1 to 100 times the weight of the immunogen, more usually from about 1 to 10 times.

In some embodiments, the whole mutant yeast cells described herein (e.g., alive or killed) may be used in preventive or therapeutic vaccine. For example, the whole mutant yeast cells are formulated in a capsule, a pill, a gel, or a cream for oral, vaginal, or rectal administration.

The neutralizing capacity of the induced antibodies can be assessed using routine methods. Thus, it is contemplated that antibodies that neutralize HIV may inhibit one or more of the following: viral attachment, coreceptor engagement, membrane fusion, or some productive interaction. See, e.g., U.S. Pat. No. 6,391,567; Lin, et al., *Virology* 77:1337 (2003); Lee, et al., *J. Virol.* 75:12028 (2001); Geijtenbeek, et al., *Cell* 100:587 (2000); Brewley, et al., *J. Am. Chem. Soc.* 123:3892-

3902 (2001); US Patent Application Nos. 20030096221; 20050064390; 20040259785; 20040228869; and 20040096823. Cell fusion encompasses the joining or union of the lipid bilayer membranes found on mammalian cells or viruses such as HIV-1. This process is distinguishable from the attachment of HIV-1 to a target cell. In one embodiment, attachment is mediated by the binding of the HIV-1 exterior glycoprotein to the human CD4 receptor. The interaction can also include coreceptors including but not limited to CCR5, CXCR4, CCR2, CCR3, CCR8, STRL33, GPR-15, CX3CR1 and APJ. See, e.g., Opperman et al., Cell Signal. 16:1201-10 (2004); Philpott et al., Curr. HIV Res. 1:217-27 (2003). In a particular embodiment, a neutralizing antibody is one that prevents or inhibits the binding of the glycosylated gp120 to DC-SIGN. See, e.g., U.S. Pat. No. 6,391,567; Lin et al., J. Virol. 77:1337-46 (2003); Mitchell et al., J. Biol. Chem. 276: 31:28939-45 (2001).

The neutralizing antibody can be any isotype. In some embodiments, the antibody is an IgG antibody. More particularly, the antibody can be an $IgG_1$, $IgG_2$, $IgG_3$, or $IgG_4$ antibody.

D. Methods of Making and Identifying Antibodies Specific for Essentially Uniformly Glycosylated Compositions Also provided herein is a method of preparing an antibody which specifically binds a protein comprising a terminal α1-2 glycan structure, the method comprising immunizing an animal with an effective amount of a composition described herein (e.g., a composition comprising a recombinant protein made by the method or the protein as disclosed herein). The composition can further comprise an adjuvant, a carrier, or both. Provided herein is the isolated antibody generated by the method disclosed herein as well as the hybridoma that produces the isolated antibody. In one embodiment, the antibody is specific for $Man_9GlcNAc_2$ gp120 or $Man_8GlcNAc_2$ gp120 and preferably has no substantial cross-reactivity with human glycoproteins.

Any suitable method of generating an antibody specific for the glycosylated proteins provided herein can be employed. Methods of immunization, producing and isolating antibodies (polyclonal and monoclonal) are known to those of skill in the art and described in the scientific and patent literature. See, e.g., Coligan, CURRENT PROTOCOLS IN IMMUNOLOGY (John Wiley 2005); Stites (eds.), BASIC AND CLINICAL IMMUNOLOGY (9th ed.) (Lange Medical Publications 1998); Goding, MONOCLONAL ANTIBODIES: PRINCIPLE AND PRACTICE (3RD ED. (Academic Press 1996); Harlow, ANTIBODIES: A LABORATORY MANUAL, (Cold Spring Harbor 1998).

Antibodies provided herein can be isolated from natural sources, be synthetic, or be recombinantly generated polypeptides using methods known in the art. The antibodies can be recombinantly expressed in vitro or in vivo. See e.g., Caruthers (1980) Nucleic Acids Res. Symp. Ser. 215-223; Horn (1980) Nucleic Acids Res. Symp. Ser. 225-232; Banga, A. K., THERAPEUTIC PEPTIDES AND PROTEINS, FORMULATION, PROCESSING AND DELIVERY SYSTEMS (1995) Technomic Publishing Co., Lancaster, Pa. For example, antibody synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); CURRENT PROTOCOLS IN IMMUNOLOGY (John Wiley & Sons, most recent edition). Antibodies also can be generated in vitro, e.g., using recombinant antibody binding site expressing phage display libraries, in addition to the traditional in vivo methods using animals including but not limited to genetically engineered animals. See, e.g., Hoogenboom Trends Biotechnol. 15:62-70 (1997); Katz (1997) Annu. Rev. Biophys. Biomol. Struct. 26:27-45 (1997); Fishwild, et al., Nat. Biotech. 14:845 (1996); Mendez, et al., Nat. Genet. 15:146 (1997); U.S. Pat. No. 6,632,976.

Once produced, polyclonal or monoclonal antibodies are tested for specific recognition of the glycosylated protein by Western blot or immunoprecipitation analysis by standard methods, e.g., as described in Ausubel, et al., supra. In some embodiments, the antibodies can be humanized. U.S. Pat. Nos. 5,585,089; 5,693,761; and WO 90/07861.

The antigen with essentially uniform glycosylation is produced using the methods provided herein. The eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein).

The antibody of the claimed invention can be an IgG, IgM, IgD, IgE, or IgA antibody. In some embodiments, the antibody is an IgG antibody. More particularly, the antibody can be an $IgG_1$, $IgG_2$, $IgG_3$, or $IgG_4$ antibody. Any suitable source can be used for the antibody. For example, the antibody can be a human, murine, rat, rabbit, bovine, camel, llama, dromedary, or simian antibody. Once a suitable antigen binding region is identified, e.g., the CDRs from an antibody which is neutralizing in vitro, in vivo or both, the antibody can be modified in any suitable manner to enhance its therapeutic efficacy. The modifications in the antibody of the claimed invention comprise at least one mutation in the amino acid sequence of the antibody. For example, one or more mutations can be introduced by modifications, additions or deletions to a nucleic acid encoding the antibody to alter one or more properties of the antibody. The antibody of the present invention can be modified in any suitable manner to confer or enhance a desirable effector function or physical characteristic. See, e.g., U.S. Pat. No. 6,737,056; and US 2004/0132101. Thus, a nucleic acid encoding the antibody modified by the method of the invention can be altered by any suitable means.

Therefore, the antibody can be a humanized antibody, a chimeric antibody, a bispecific antibody, a fusion protein, or a biologically active fragment thereof. In some embodiments, the antibody (or biologically active fragment thereof) is a fusion protein. The fusion protein can encompass additional peptide sequence that simplifies purification or production. Fusion proteins also may include domains and/or whole polypeptides that are biologically active in a manner that complements the activity of the antibody. For example, the antibody can be fused to a cytokine, ligand, adhesion molecule, peptide, receptors, enzymes, therapeutic proteins, dyes, small organic molecules, or any biologically active portion thereof.

Any suitable means can be used to determine the binding affinity of the antibody of the present invention. In one example, the affinity is determined by surface plasmon resonance (Biacore). The antibody of the present invention can also be modified further to increase binding affinity using methods known in the art. See, e.g., U.S. Pat. No. 6,350,861.

The antibody provided herein can be one that is suitable for immunoassays. Particular assays include ELISA assays, sandwich assays, radioimmunoassays, and Western Blots.

See e.g., ANTIBODY ENGINEERING: A PRACTICAL APPROACH (Oxford University Press, 1996). These monoclonal antibodies will usually bind with at least a $K_d$ of about 1 µM, more usually at least about 300 nM, typically at least about 30 nM, preferably at least about 10 nM, more preferably at least about 3 nM or better, usually determined by ELISA Any suitable method may be employed to determine the biological activity of the antibody in the presence of the virulence factor. In one embodiment, an antibody has anti-virulence factor activity if the antibody reduces the pathogenicity of the organism and/or the toxicity of the virulence factor by at least 20%, at least 50%, 60%, 70%, 80%, 90%, or 100%. In another embodiment, the antibody of the present methods has anti-virulence activity if the antibody reduces the pathogenicity of the organism and/or the toxicity of the virulence factor by at least 20%, at least 50%, 60%, 70%, 80%, 90%, or 100% in presence of one or more other anti-virulence factors.

The antibody of the present invention can specifically bind any suitable glycosylated virulence factor. The virulence factor can be an adherence factor, a coat protein, an invasion factor, a capsule, an exotoxin, or an endotoxin. The anti-pathogenic effect of the antibody can result from the antibody binding a virulence factor, clearance of the factor, inactivation of the factor, and the like.

In another aspect, the present invention provides an isolated or recombinant nucleic acid comprising a sequence encoding the antibody disclosed herewith, a vector comprising the encoding nucleic acid, and a cell comprising the encoding nucleic acid or the vector comprising the encoding nucleic acid. Typically, the vector comprises the antibody-encoding nucleic acid operably linked to a promoter suitable for expression in the designated host cell. Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris*, and *Bacillus subtilis*. Exemplary host cells also include eukaryotic organisms, e.g., various yeast, such as *Saccharomyces* spp., including *Saccharomyces cerevisiae, Schizosaccharomyces pombe, Pichia pastoris*, and *Kluyveromyces lactis, Hansenula polymorpha, Aspergillus niger*, and mammalian cells and cell lines, and insect cells and cell lines. Thus, the invention also includes antibodies and their encoding nucleic acids optimized for expression in these organisms and species. See, e.g., U.S. Pat. No. 5,795,737; Baca (2000) *Int. J. Parasitol.* 30:113-118; Hale (1998) *Protein Expr. Purif.* 12:185-188; Narum (2001) *Infect. Immun.* 69:7250-7253; Outchkourov (2002) *Protein Expr. Purif.* 24:18-24; Feng (2000) Biochemistry 39:15399-15409; and Humphreys (2000) *Protein Expr. Purif* 20:252-264.

In one aspect, the present invention provides a pharmaceutical composition comprising the antibody of the present invention, and a suitable excipient which is administered as a therapeutic agent. In one aspect, the present invention provides a pharmaceutical composition comprising the engineered antibody of the present invention, and a suitable excipient. The present invention provides a pharmaceutical composition comprising at least one monoclonal antibody set forth above, and a suitable excipient. Formulations and excipients useful in the pharmaceutical compositions are those well known in the art. An antibody useful in the present methods (from whatever source derived, including without limitation from recombinant sources) may be administered to a subject in need, by itself, or in pharmaceutical compositions where it is mixed with suitable carriers or excipient(s) at doses to treat or ameliorate a variety of disorders. See e.g., REMINGTON: THE SCIENCE AND PRACTICE OF PHARMACY (latest edition). Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain other anti-pathogen such cytokines or antimicrobial agents as is desirable.

When the antibody of the present invention is co-administered with one or more biologically active agents, the antibody provided herein may be administered either simultaneously with the biologically active agent(s), or sequentially. If administered sequentially, the attending physician will decide on the appropriate sequence of administering protein of the present invention in combination with the biologically active agent(s).

Toxicity and therapeutic efficacy of such antibodies can be determined using routine methods. The exact formulation, route of administration and dosage can be chosen by the individual physician in view of the patient's condition. See, e.g., Fingl., et al., THE PHARMACOLOGICAL BASIS OF THERAPEUTICS 1 (latest edition).

Further provided herein is a method of inducing neutralizing antibodies against a pathogen in a subject in need thereof, comprising administering an effective amount of a pharmaceutical composition comprising the protein provided herein or a protein prepared by the method provided herein, and a suitable excipient. In some embodiments, the method further comprises administering an adjuvant. In a specific embodiment, the pathogen is HIV.

Yet further provided herein is a method of preventing or treating pathogen-induced disease in a subject in need thereof, comprising administering an effective amount of a pharmaceutical composition comprising the protein provided herein or a protein prepared by the method provided herein, and a suitable excipient. In some embodiments, the method further comprises administering an adjuvant. In a specific embodiment, the pathogen is HIV. In one embodiment, the protein is gp120. In some embodiments, the pharmaceutical composition further comprises multiple gp120 proteins from different HIV strains.

Further provided is a method of identifying a neutralizing monoclonal antibody for HIV transmission, comprising: a) contacting a first cell, wherein the first cell expresses dendritic cell-specific C-type lectin (DC-SIGN), with a second cell expressing CD4+ and CCR5+, b) coculturing the first and second cells with infectious viral particles; c) contacting coculture with a candidate antibody; and d) determining relative infectivity, whereby the neutralizing antibody is one that reduces or eliminates relative infectivity of the second cell by infectious viral particles. See, e.g., U.S. Pat. No. 6,391,567; Bashirova, et al., *J. Exp. Med.* 193:671 (2001); Lee, et al., *J. Virol.* 75:12028 (2001).

Having now generally described the invention, the same will be more readily understood through reference to the following examples which are provided by way of illustration, and are not intended to be limiting of the present invention, unless specified.

EXAMPLES

Example 1

Selection of an expression system. A strain of *S. cerevisiae* deficient for Pmr1p protein, a calcium-dependent ATPase important for the transport of $Ca^{++}$ from the ER to the Golgi was selected. (55,56). The pmr1Δ strain is a so-called super-secretor of heterologous proteins, secreting nearly 100% of heterologous proteins. (57-58). This strain secretes glycoproteins with only $Man_8GlcNAc_2$ trimmed from $Man_9GlcNAc_2$ by mannosidase I in the ER as reported for several proteins (58-60).

Cloning of HIV-1 gp120 genes to express secreted glycoproteins. The signal sequence of the *S. cerevisiae* α mating factor (MFα) was cloned into an expression vector pYES2/CT (Invitrogen). The coding sequence for the MFα was amplified from total yeast DNA by PCR. The PCR primers contained KpnI and BamHI sites. A 250 bp fragment was amplified, purified and ligated into the pGEM®-T (Promega). After transformation and miniprep identification, a positive clone was identified. The pGEM®-T-MFα and pYES2/CT plasmids were then digested with BamHI and Kpn1, simultaneously. After purification of the MFα band and pYES2 band, the plasmids were ligated, transformed into NovaBlue competent cells and seeded onto LB-ampicillin plates. A positive clone containing MFα was identified and used to clone gp120.

The sequences encoding HIV-1 gp120 proteins from strains of JR-FL, JR-CSF and YU2 were amplified by PCR using their corresponding plasmids (AIDS Research and Reference Reagent Program, ARRRP) as the templates. The PCR amplified gp120 DNA fragments were cloned into pYES2/CT-MFα plasmid containing EcoRI and XbaI sites. Then the three pYES2/CT-MFα-gp120 plasmids were transformed into NovaBlue competent cells, and positive clones were identified by digestion analysis of minipreps. These plasmids were used for transformation into a diploid yeast strain pmr1Δ (Invitrogen) using a quick Lithium acetate transformation protocol. The pYES2/CT vectors contained the inducible GAL1 promoter, permitting high expression levels of the recombinant protein following induction with galactose. To produce and secrete gp120 into culture media, transformed yeast cells were grown overnight at 30° C. in —Ura/raffinose media. After centrifugation, the cells were resuspended with —Ura/galactose media for induction of gp120 expression.

Figure 2:
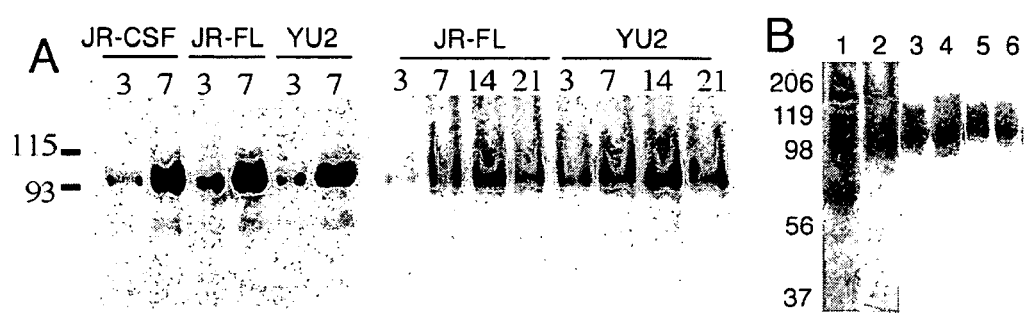
FIG. 2 shows the expression of HIV-1 gp120 glycoproteins in yeast. A. Expression of gp120 proteins from 3 HIV-1 strains in Δpmr1 was induced by galactose for the indicated days. The proteins in the culture supernatants were detected with 2G12. B. Purification of $HIV_{YU2}$ gp120. Lane 1 shows the concentrated yeast culture media, lane 2 after dialysis and centrifugation, lanes 3 and 4 after GNL and gel filtration at 200 and 400 ng respectively, and lanes 5 and 6 $HIV_{YU2}$ gp120 produced in 293T cells at 200 and 400 ng.

Expression, purification, and analysis of uniformly glycosylated HIV-1 Env proteins. The pmr1Δ strain is temperature sensitive and grows slowly at permissive temperatures. Therefore, gp120 expression was examined at different temperatures and time points in order to determine the conditions under which these yeast cells can express the highest level of proteins and secrete them most efficiently into culture media. The pmr1Δ yeast cells secreted the greatest amount of gp120 proteins at 25° C. for 7 to 14 days (FIG. 2A). gp120 proteins were detected after 1-day of culture and continued to accumulate in the culture media for at least 14 days, indicating that the yeast cells continued production and secretion of the heterologous proteins. It also indicated that the glycosylated gp120 proteins were stable at room temperature. If the gp120 glycoproteins produced in the pmr1Δ strain contained only $Man_8GlcNAc_2$ oligosaccharides, the proteins should have predicted molecular masses of 99603 Da, 96385 Da, and 99621 Da for JR-CSF, JR-FL, and YU2, respectively. Western blots showed that the proteins migrated at these predicted sizes in SDS-PAGE. The blot was probed with MAb 2G12 which readily detected the gp120 proteins produced in the pmr1Δ strain (FIG. 2A).

Purification procedures were simple because yeast culture media was protein poor. A combination of mannose binding lectin affinity chromatography and gel filtration was sufficient to obtain purities greater than 95%. In brief, the culture supernatants at 14 days were concentrated and dialyzed against dialysis buffer (1 mM $CaCl_2$ and 1 mM $MnCl_2$) for 16 h at 4° C. After centrifugation at 40,000 g for 30 min at 4° C., the precipitate containing proteins of non-interest was removed. Agarose-Con-A column (Vector Laboratories, CA) was then used to purify these gp120 proteins. Supernatant containing gp120 proteins was loaded onto pre-equilibrated Con-A-agarose columns and incubated at 4° C. for 16 h. The column was then washed with dialysis buffer and the bound proteins were eluted with elution buffer (500 mM α-methyl mannoside, 250 mM NaCl, 20 mM TrisCl, 1 mM $CaCl_2$ and 1 mM $MnCl_2$, pH6). The purified materials contained mainly a 100 kDa and a 160 kDa protein. Gel filtration was then used to remove the 160 kDa protein. The prepacked column of Sephacryl® S-100 HR (Amersham Pharmacia Biotech) was washed with washing buffer (50 mM imidazole, 100 mM NaCl, 10 mM sodium phosphate, pH 8.0). The bound proteins were eluted with elution buffer (500 mM imidazole, 100 mM NaCl, 10 mM sodium phosphate, pH 8.0) and 1 ml fractions were collected. The fractions were analyzed by SDS-PAGE followed by Coomassie blue staining (FIG. 2B).

Following purification, the carbohydrate types will be analyzed using PGNase F digestion and mass spectrometry. Typically, greater than 90% of the Man will be Man8 or Man9.

Figure 3:
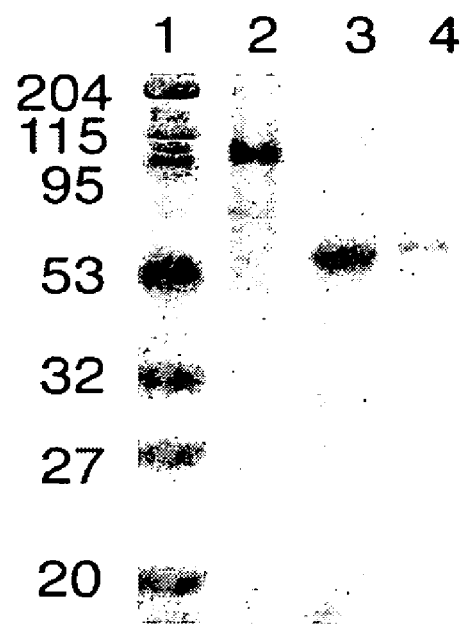
FIG. 3 shows EndoH digestion assay of gp120 protein produced in yeast. The same lot of purified gp120 proteins used for MS/MS analysis was digested with EndoH. Then the non-digested and digested proteins were separated by SDS-PAGE followed by Coomassie blue staining. Lane 2 is the non-digested at 200 ng, lane 3 digested at 400 ng, and lane 4 is a non-glycosylated gp120 from $HIV_{SF2}$ expressed in yeast.
Figure 15:
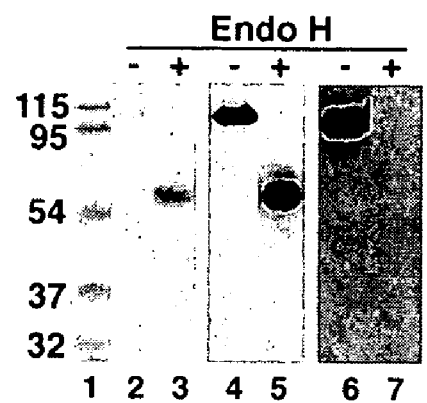
FIG. 15 shows glycan analysis of 2G12 cross-reactive protein PST1. A. Partially purified Yp100 protein was digested with Endo H and the non-digested (lanes 2, 4 and 6) and digested (lanes 3, 5 and 7) proteins were separated by SDS-PAGE gel and subjected to Commassie blue staining (lanes 1-3), Western blots with anti-PST1 polyclonal antibody (lanes 4 and 5), and with MAb 2G12 (lanes 6 and 7). This is followed by incubation with HPR labeled secondary antibody, ECL, and exposed to X-ray films.
Figure 16:
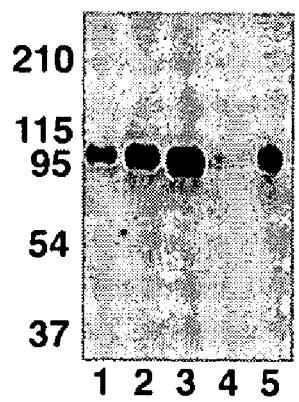
FIG. 16 shows cross-reactivity of PST1 to 2G12 in pmr1 and mnn1 double mutant. Cell lysates from 5 different double mutant stains were prepared and separated on 4-20% gradient SDS-PAGE. The blot was probed with MAb 2G12 followed by incubation with HPR labeled secondary antibody, ECL, and exposed to X-ray films.
Figure 17:
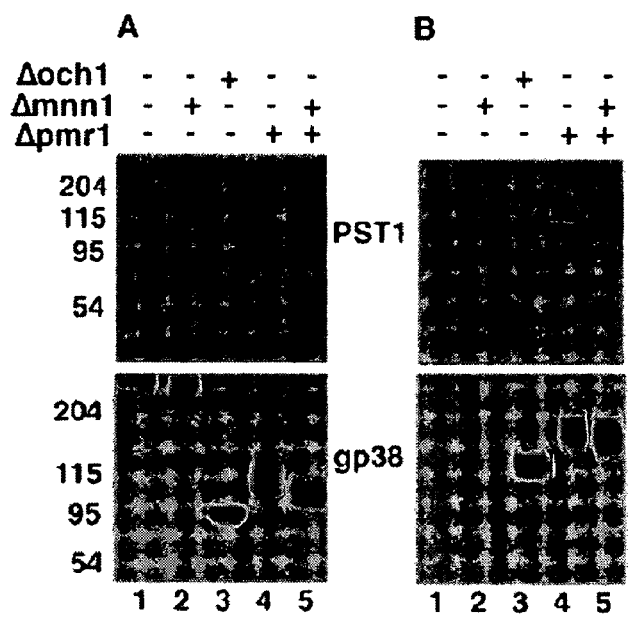
FIG. 17 shows up-regulation and migration shits of PST1 in double mutant. A. PST1 in yeast cell lysates. Cell lysates from different stains were separated on 4-20% gradient SDS-PAGE. The levels of PST1 expression in wild type and mutants were analyzed using Western blot with anti-PST1 polyclonal antibody. Lane 1, wild type; lane 2, Δmnn1; lane 3, Δoch1; lane 4, Δpmr1; lane 5, Δpmr1 and Δmnn1 double mutant. Upper panel shows PST1 was only detected in the lysates of pmr1 and mnn1 double mutant. Lower panel shows another glycosylated protein GP38 that is detectable in all 5 strains. B. PST1 in yeast cell culture media. Yeast cells from different strains were cultured in rich media for 24 h and the proteins in media were precipitated with acetone. The levels of protein secretion were detected using Western blot with anti-PST1 antibody (upper panel) and anti-GP38 (lower panel).

To estimate the quantity of gp120 and contaminants, the purified proteins were digested with an enzyme endoglycosidase H (Endo H) that is known to cleave high mannose and hybrid types of carbohydrates. The results from FIG. 3 show that the predominant band was a 55-60 kDa protein, correlating to the size of gp120 polypeptide. Based on the data from FIG. 3, the estimated gp120 purity was greater than 90%. In later experiments, this band was further identified to be mostly PST1, a yeast protein. See FIG. 15.

Antibodies specific for glycosylated gp120 proteins. In order to test whether mannose-specific antibodies can be induced and react with HIV-1 Env proteins, rabbits were immunized with a yeast cell wall extract, zymosan A, which contains β-glucan and α-mannan. These mannose-rich structures contained mostly terminal α1,3 and α1,6 linkages, with a few α1,2 structures such as those commonly found in gp120. Two rabbits were immunized with 200 μg of zymosan A containing CFA at week 0, and boosted with 100 μg of antigen containing IFA at weeks 2 and 4 and thereafter every 4 weeks. Immune sera were collected at week 5 and 1 week after each booster. The antigen elicited a good antibody response as determined by ELISA analysis, using either zymosan A or mannan captured to the plates (FIG. 4A). Notably, the immune sera also recognized some of the tested gp120 glycoproteins (FIG. 4B). The anti-mannan sera showed a broad, though relatively low level of reactivity to clades E (ChenMai and 93TH975), C(CN54 and 96ZM651) and one of clade B (LAV). In contrast, 2G12 MAb mainly reacted with clade B (ADA, JR-FL, BAL, LAV) strains, but had no response to the clade C (CN54 and 96ZM651) or little response to the clade E strains tested (93TH975 and Chen-Mai). The high titer of antibody to the clade E Chen strain was further confirmed by Western blot and repeated ELISA. These results suggest that antibodies against mannose can be induced in animals, and that reactivity to HIV gp120 can be obtained. These findings provide a strong rationale for moving forward with our novel, mannose-rich gp120 immunogens.

The gp120 proteins from strains YU2, JR-FL and JR-CSF expressed in pmr1Δ yeast cells contained 22-24 Man8 structures while those expressed in mammalian cells from the same HIV strains contained about half Man5-9 and half complex carbohydrate structures. To determine if gp120 proteins expressed in yeast were recognized more efficiently by antibodies against mannan and as well as 2G12, we used the purified gp120 protein from YU2 stain from yeast to compare with YU2 expressed in mammalian cells. The results from this ELISA analysis (FIG. 4C) show that gp120 protein from yeast has much higher antigenicity to anti-mannan antibody than that from mammalian cells. This figure also showed that the anti-mannan antibody recognized the Man9-BSA conjugate but not BSA alone.

Isolation of Man9 and conjugation of Man9 to BSA. In order to use $Man_9GlcNAc_2$ as a screening tool for anti-α1,2-Man structure antibodies, Man9 was isolated from a plant protein and conjugated to BSA. Specifically, the Man9 glycan was isolated from soybean agglutinin (SBA, EY labs) by the Glycobiology Core Facility at the University of California San Diego (UCSD). Briefly, the N-glycans on purified SBA were released using PNGase F and purified using TCA precipitation to remove the proteins. The supernatant was passed over a SepPak® C18 cartridge to remove residual detergent, and the glycans were purified on a porous graphitized carbon cartridge. Monosaccharide analysis indicated that the yield was 0.2 mg from 25 mg of protein. The glycan was analyzed by HPAEC-PAD and compared with reduced $Man_9GlcNAc_2$ standard and reduced RNAse B glycans. An estimated 90% of the glycan was in fact $Man_9GlcNAc_2$ and the ratio of $Man_9GlcNAc_2$ to $Man_8GlcNAc_2$ was 9:1. An aliquot was subjected to MALDI-TOF mass spectrometric analysis. The major species was $Hex_9HexNAc_2$ although smaller glycans were also observed in lower amounts.

Figure 5:
FIG. 5 shows the analysis of BSA-Man9 conjugate. The BSA-Man9 conjugate was analyzed with 10% SDS-PAGE gel followed by Coomassie blue staining. Lane 1 is non-conjugated BSA, lane 2 BSA-SMCC, and lane 3 BSA-SMCC-Man9.

$Man_9GlcNAc_2$ was then conjugated to BSA using sulfo-SMCC (Pierce Biochemicals) method. Briefly, $Man_9GlcNAc_2$ was reacted with 2-aminoethanethiol-HCl at 85° C. for 30 min. The reaction mixture was dialyzed against water to remove the reaction reagent and salt, and then vacuum dried. The Man9 derivative was then dissolved in 100 μl SMCC reaction buffer (0.1 M sodium phosphate, 50 mM EDTA, pH 7.4). BSA was activated with sulfo-SMCC in the reaction buffer for 2 h. The excessive SMCC was removed by passing the reaction mixture though Sepharose® G25 column. Fractions containing BSA-SMCC were combined and concentrated. 100 μg BSA-SMCC was reacted with 50 μg of derived Man9 for 30 min. The reaction was stopped by addition of 0.5 M cysteine, and dialyzed against phosphate buffer saline. The solution was vacuum dried and the BSA-Man9 conjugate was dissolved with 0.1 ml of water to have the concentration of BSA at 1 mg/ml. FIG. 5 shows the migration shift of the conjugate of BSA-Man9 compared to BSA-SMCC and non-conjugated BSA.

Preparation of DC-SIGN antibodies and recombinant proteins. Antibodies against DC-SIGN were used to monitor expression of the recombinant DC-SIGN protein. Two antibodies were produced in rabbits using synthetic peptides. The immune sera were purified by immunoaffinity chromatography. Both peptide antibodies recognized a 44 kDa band in the lysates from human mucosal tissues. This band was blocked by the antigenic peptides indicating that these two antibodies are specific.

Cloning and expression of DC-SIGN. In order to perform gp120-DC-SIGN binding assays and test the neutralizing activity of elicited antibodies, the extracellular domain of DC-SIGN was cloned and expressed. The cDNA fragment of DC-SIGN was prepared by PCR amplification and ligated into the pET100 vector (Invitrogen). BL21(DE3) bacteria were used to express the recombinant protein in the presence of 0.5 M IPTG. Bacterial cells were harvested after 4 h of IPTG induction. The bacterial lysates were separated into soluble and insoluble fractions and analyzed by SDS-PAGE. The recombinant ECD protein was found in the insoluble fraction and purified using Ni-NTA columns (FIG. 6A).

Refolding and purification of DC-SIGN from bacteria inclusion bodies. Because the insoluble proteins in inclusion bodies were incorrectly folded. The denatured proteins were refolded to obtain biologically functional proteins, and the refolded proteins were purified with Ni-NTA and D-mannose affinity chromatography. In brief, bacterial cells were lysed with lysis buffer (50 mM Tris-Cl, 150 mM NaCl, 5 mM 2ME, pH 7.45) containing 1 mg/ml lysozyme and 5 μg/ml DNAse I to release inclusion bodies and soluble proteins. The inclusion bodies were precipitated by centrifugation and thoroughly washed to remove soluble proteins. The inclusion body was lysed in refolding buffer (20 mM Tris, 10 mM 2ME, 10 mM DTT, 1 mM glycine, 1 mM GSH, 0.1 mM GSSG, 1 mM EDTA, pH 10.5) containing 8 M urea. The urea concentration was diluted with refolding buffer and the solution was adjusted with 1 N HCl sequentially to pH 9.0, 8.8, 8.5 and 8.0. The refolding solution was centrifuged at 40,000 g 30 min to remove the insoluble materials. The refolded proteins were then purified with Ni-NTA agarose column and eluted with lysis buffer containing 500 mM imidazole. The quantity and purity of purified ECD protein was analyzed with SDS-PAGE followed by Coomassie blue staining. FIG. 6A shows that the refolded protein had purity greater than 90% after Ni-NTA purification. The elute from Ni-NTA column containing ECD protein was further purified using a D-Mannose-agarose column pre-equilibrated with loading buffer in order to select proteins competent to bind ligand. The column was washed with loading buffer and the bound proteins were eluted with 50 mM α-D-mannose. Fractions were analyzed by SDS-PAGE followed by Coomassie blue staining. The binding assay in FIG. 6B shows this recombinant protein is functional since it binds to gp120 with a similar affinity to a polyclonal antibody.

Binding assay of DC-SIGN-gp120 interaction. To test the DC-SIGN activity, a binding assay of DC-SIGN-gp120 is performed. Different dilutions of immune sera with different concentrations of 2G12 MAb as a control are incubated with 200 ng of gp120 proteins to determine $IC_{50}$ values. gp120 proteins from YU2 and JR-FL strains produced in mammalian cells and yeast cells are used in parallel to compare. Then the wells are incubated with anti-gp120 polyclonal antibody (US Biological) followed by goat anti-rabbit IgG-HRP conjugates. Each condition is in duplicate. The quantity of gp120 bound to DC-SIGN is determined using a standard curve created based upon the gp120 concentration and OD value. The percent inhibition at a given antibody concentration is expressed as [(gp120 quantity in the absence of antibody—gp120 quantity in the presence of a given antibody concentration)/gp120 quantity in the absence of antibody]×100. The inhibition potency, i.e., 50% ($IC_{50}$) and 90% ($IC_{90}$) inhibitory doses, are determined. To test the broadly neutralizing reactivity of each antibody, recombinant gp120 glycoproteins from clades A, B, and C will be used.

The purified ECD protein at 500 ng/well is used to coat microwell plates for 16 h. The wells are blocked with TBS-Tween® containing 0.1% BSA. The gp120 protein from YU2 strain produced in mammalian cells is used to bind to the immobilized proteins. Then the wells are incubated with anti-gp120-MN polyclonal antibody followed by goat anti-rabbit IgG-HRP conjugates. After color development with substrate, optical density ($OD_{450}$) is read with a microwell reader. Each condition is set in duplicate.

Figure 7:
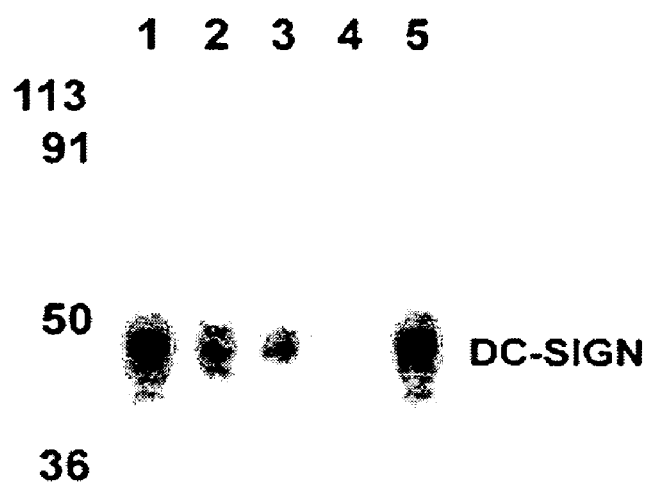
FIG. 7 shows the development of DC-SIGN MAbs. The purified DC-SIGN ECD protein was used to immunize Balb/c mice. The splenocytes from a mouse with good antibody response were used for cell fusion. After ELISA screening of the culture supernatants, the cells from positive wells were expanded and subcloned. The supernatants from wells with single clones were screened using Western blots. Each separate lane represents an individual clone.

Besides the two polyclonal antibodies, MAbs against the purified ECD protein have also been developed. After first screening of culture supernatants using ELISA and expansion of the positive clones, hybridomas were further screened using Western blot (FIG. 7). These MAbs showed high specificity since a longer exposure of film (30 min) did not show other detectable bands.

Figure 8:
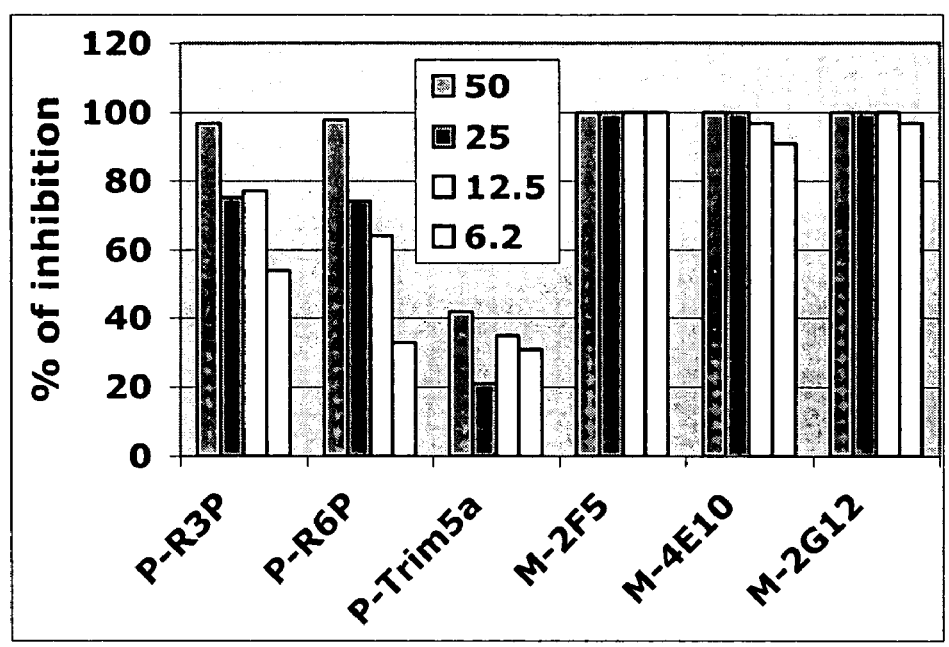
FIG. 8 shows a neutralization assay. Neutralizing activities of two polyclonal (P) antibodies were tested using a LuSIV cell line infected by pseudovirus bearing pHXB2 gp160. Three well-known neutralizing MAbs (M) were used as positive controls. Four doses (50, 25, 12.5 and 6.25 μg/ml) of each antibody were examined.
Figure 9:
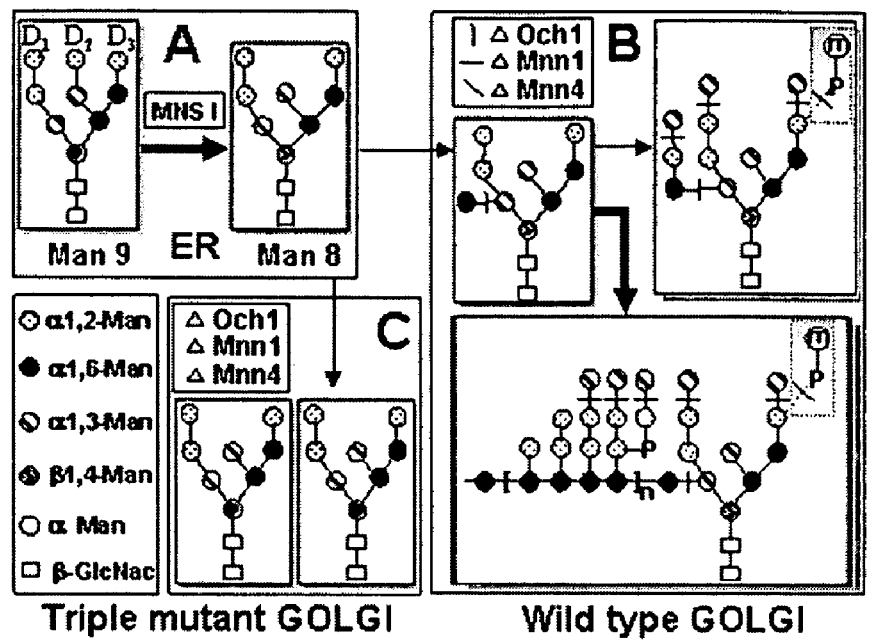
FIG. 9 shows structure and processing of N-linked oligosaccharides.

Recombinant gp120 proteins and neutralization assay. gp120 proteins from different clades will be used to perform the primary screening of the immune sera and the hybridoma supernatants. These proteins are ideally expressed in mammalian cells to be fully glycosylated. Many of these proteins are available from commercial sources. Less than 1 mg of each protein will be needed for screening. The HIV neutralization assay are typically performed as described in Binley et al., *J. Virol.* 78:13232-52 (2004), Li et al., *J. Virol.* 79:10108-25 (2005); Mascola et al., *J. Virol.* 79:10103-7 (2005). Briefly, the retrovirus plasmid pHIV-gpt and gp160 env pHXB2 to produce a high titer pseudovirus after co-transfection of Cos-7 cell. This pseudovirus infects luciferase indicator cell lines LuSIV very well as measured by luciferase activity using Bright-Glo™ Luciferase assay kits (Promega) and a recently purchased Veritas Luminometer (Tuner Biosystem). This system was used to test anti-HIV-1 polyclonal antibodies recently produced in our lab (FIG. 8). The two polyclonal antibodies showed dose dependent neutralizing activity. Trim5α polyclonal antibody was used as a negative control and human MAbs (2F5, 4E10, and 2G12) as positive controls.

Preparation of gp120 conjugated to immunostimulant. To enhance the immunogenicity of the uniformly glycosylated gp120, multiple antigenic peptide (MAP) containing universal T cell epitopes from tetanus toxin will be synthesized, conjugates of gp120-tetanus toxoid and gp120-MAP will be prepared using different coupling procedures, and will be analyzed for the coupling efficiency and the antigenicity. Briefly, a multiple antigenic peptide (MAP) with 4 branches of the p2 sequence (p24) will be synthesized by a well-established peptide company (AnaSpec, Inc.). The MAP peptide will be purified greater than 90% purity by HPLC and analyzed by mass spectroscopy. The MAP peptide will be covalently coupled to the gp120 protein by using the cysteine residue that has been added to the core matrix. The cysteine sulfhydryl group will be cross-linked to free amino groups on the gp120 proteins using the SMCC method, and thus should not modify the carbohydrate structures that we hope to develop antibodies against. In brief, the gp120 proteins at 10 mg/ml will be reacted with Sulfo-SMCC (Pierce) solution at 10 mg/ml in coupling buffer (1× PBS, 0.1 M EDTA, pH7.2) for 2 h. The reaction solution will be passed through a Sephadex® G-25 column to remove excess SMCC. Fractions containing protein will be collected. The synthetic MAP peptide will be dissolved in coupling buffer at 10 mg/ml and mixed with activated antigen at a 30:1 molar ratio, which allows most of the free amine groups on the gp120 proteins to be coupled. The cross-linking reaction proceeds for 2 h. All reactions will be performed at room temperature.

A gp120-tetanus toxoid conjugate will be prepared using a similar approach. The tetanus toxoid protein (TT, Statens Serum Institute, Denmark) will be coupled to gp120 by crosslinking through their free amino groups. Briefly, fresh glutaraldehyde in 100-fold molar excess, to prevent self-conjugates, is reacted to TT in 50 mM borate buffer, pH 8.0. Free glutaraldehyde is removed by passing through a Sephadex® G-25 column. TT-glutaraldehyde is then coupled to gp120. Free aldehyde groups are blocked by the addition of 1 M glycine. The reaction mixture is re-passed through the Sephadex® G-25 column. The fractions containing TT-gp120 conjugate are collected and dialyzed against PBS.

The coupling efficiency is analyzed using gel shift assays. Briefly, the conjugates are analyzed with 4-20% gradient SDS-PAGE followed by Coomassie blue staining, and Western blot using antibodies against gp120. The conjugates migrate slower than the non conjugated protein. The size changes of the conjugates depend on the numbers of MAP peptide and protein molecules that have been coupled to the gp120 protein. The antigenicity of the conjugates will be tested by comparison to non-conjugated gp120 protein using ELISA with the polyclonal antibody against mannan and 2G12 MAb.

Screening the immunogenicity of the gp120 proteins and their conjugates in vivo. Six groups of 6 BALB/c mice at 5 to 6 weeks old will be immunized (Table 1). Antigens are injected subcutaneously at the doses indicated. The mice are boosted with the same dose of antigen 14 days after the primary immunization and every three weeks thereafter. They are bled 1 week after each booster injection. Thus, the mice are immunized at week 0, 2, 5, 8 and 11 and immune sera are collected at week 0, 3, 6, 9, and 12. Both YU2 and JR-FL can be employed in order to have more Manα1,2-Man epitopes and develop more numbers of broadly neutralizing MAbs.

TABLE 1

Groups of immunization

| Group | gp120/ conjugate | Adjuvant | Significance |
|---|---|---|---|
| 1. | 10 μg | None | No adjuvant control |
| 2. | 10 μg | CFA/IFA | Co-administration of gp120 with CFA/IFA adjuvant as control |
| 3. | 20 μg | gp120-TT | Compare the effect of TT with CFA/IFA |
| 4. | 50 μg | gp120-TT | Compare the dose effect of the conjugate |
| 5. | 20 μg | gp120-MAP | Compare the effect of TT-MAP with CFA/IFA |
| 6. | 50 μg | gp120-MAP | Compare the dose effect of the conjugate |

Antibody titers will be tested using ELISA with gp120 antigens coated microwell plates. The ELISA procedures are briefly described. Costar microwell plates are coated with 300 ng of antigen/well in 100 μl of 50 mM carbonate (pH9.5) for 24 h. The wells are blocked with 200 μl of blocking buffer (1% BSA, 0.02% thimerosal in PBS) for 2 h. After washing, 100 μl of serially diluted immune sera is incubated with antigen-coated wells for 2 h. After 5 washes with PBS-Tween®, the wells are incubated with 100 μl of goat anti-mouse IgG-HRP conjugates (Sigma) at 1:5000 in blocking buffer for 2 h. After washing, the wells are incubated with 100 μl of HRP substrate TMB solution (BD Bioscience) for 10 min and the reaction is stopped by addition of 100 μl of 1 N HCl. The optical density is read at $A_{450}$ by microwell reader. All reactions are performed at room temperature.

Screen immune sera for cross-reactive antibodies to gp120 proteins from different clades. Up to 12 clades of HIV-1 isolates globally have been reported and clades A (27%), B (12%) and C (42%) comprise more than 80% of all HIV-1 infections. The Man9 and Man8 forms of high mannose oligosaccharides are highly conserved in all HIV-1 strains and isolates. Thus, antibodies against the Manα1,2-Man structures could recognize an epitope from a single Man8 or Man9, or a conformational epitope formed by 2 or 3 of these glycans. Therefore, the antibodies against Manα1,2-Man epitopes could recognize most HIV-1 strains and isolates.

To develop MAbs with broadly neutralizing activity, we will screen the immunized mice and hybridoma supernatant with gp120 glycoproteins from strains of clade A (e.g., Q2317, B2539, and Q1769), B (e.g., ADA, YU2, JR-FL, 89.6, BaL, SF162) and C (e.g., DU123, DU422, DU179, and 981N012). In addition, antibodies against high mannose Man8 structures can be tested. Man8 will be isolated from gp120 protein produced in yeast, and conjugated to BSA using sulfo-SMCC method disclosed herein. BSA-Man8 will be used to coat the microwell plate and to screen immune sera for antibodies against Manα1,2-Man epitopes.

Mice with a serum titer≧1:10,000 to the immunogen, and ≧1,000 to gp120 proteins from different clades and BSA-Man8 will be selected for creation of hybridomas. Briefly, the mice are boosted with same dose of antigen three days before fusion, after which they are sacrificed and the spleens are aseptically harvested. Cell suspensions are prepared by injection of 20 ml of sterile complete serum-free DMEM (CSFD) into a spleen. Concurrently, cultures of myeloma cells SP2/0-Ag14 (ATCC) are harvested. The splenocytes and myeloma cells are washed three times with DMEM and resuspended separately in 10 ml of CSFD. After assessing the cell viability, they are mixed at 1:1 ratio, supplemented with 30 ml DMEM, and pelleted by centrifugation. The cell pellet is resuspended by slowly adding 1 ml of 50% polyethylene glycol (PEG 400, Roche) with stirring after each drop. Sterile CSFD is added to the mixture drop-by drop with stirring to bring the final volume to 10 ml. The fused cells are centrifuged and resuspended with complete DMEM-20/HEPES/pyruvate/HAT. The cell suspension is adjusted to $2.5\times10^6$ total cells/ml. The fused cells are seeded in 96-well plate and incubated in a humidified 37° C., 5% $CO_2$ incubator for 7 days. Then, the media is replaced with complete DMEM-20/HEPES/pyruvate/HT. On day 12 to 15 the hybridomas are ready for screening as witnessed by visible hybridoma colonies. Typically, around $1\times10^8$ cells per spleen are seeded into ten 96-well plates, and obtain ≧80% efficiency in fusion.

The supernatants in the wells with visible colonies are screened using ELISA with immunogen. The procedure is the same as screening immune sera except the antigen-coated wells are probed with 100 μl of non-diluted hybridoma supernatant. The candidate hybridoma cells in positive wells are transferred to 24 wells with DMEM-20/HEPES/pyruvate and cloning/expansion medium, and expanded 3 to 5 days. The supernatants are screened again with gp120s from different clades and BSA-Man8, as above. Cells in the wells that show positive to all or most tested gp120 proteins, and BSA-Man8, are subjected to cloning by plating 1 and 3 cells per well. Cells are cultured for 7 to 10 days and candidate clones are screened again using the same panel of antigens as above. Subcloning and screening are repeated until stable hybridoma cell lines of interest are established.

To test the neutralizing activity of these MAbs against a large number of HIV-1 strains and primary isolates, MAbs will be produced in mice and purified with Protein A affinity chromatography.

Identify MAbs that can potently neutralize a broad range of HIV-1 stains and primary isolates. Culture supernatant and MAbs the HIV neutralization assay will be tested for the ability to neutralize homologous HIV strains. Thus, the hybridoma culture supernatant from animals immunized with YU2 or JR-FL gp120 produced in yeast will be tested for the ability to neutralize HIV pseudotypes bearing the YU2 or JR-FL Env protein as well as a luciferase reporter gene. Supernatants and MAbs will be tested for the ability to neutralize infection of p24-normalized virus stocks on U87 cells bearing CD4 and CCR5 (or CXCR4 when X4 virus strains are used). The virus pseudotypes are first incubated with non-diluted supernatant or serial dilutions of MAbs for one hour prior to infection. The amount of luciferase produced in infected cells is measured 48 to 72 hours later. Neutralizing activity is displayed as the percent inhibition of viral replication (luciferase activity) at each antibody dilution compared with an antibody-negative control: % inhibition {1[luciferase Ab luciferase Ab]}100. Titers are calculated as the reciprocal of the MAb dilution conferring 50% inhibition ($IC_{50}$). Supernatants and MAbs that neutralize homologous virus will then be tested for the ability to neutralize a variety of primary HIV-1 strains.

Materials and Methods Used in Examples 2-4

Generation of Double and Triple Yeast Mutants:

Yeast strains and media. Four yeast deletion strains used in this study were acquired from Open BioSystems: MATα, his3Δ1, leu2Δ0, lys2Δ0, ura3Δ0, mnn1:kanMX4 (10322); MATa, his3Δ1, leu2Δ0, met15Δ0, ura3Δ0, mnn4:kanMX4 (7034); MATa, his3Δ1, leu2Δ0, met15Δ0, ura3Δ0, och1:kanMX4 (4406); and MATa his3Δ1 leu2Δ0 met15Δ0 ura3Δ0 pmr1:kanMX4 (14534). Two parental yeast strains were acquired from ATCC for verification and screening of mating type: MATa, trp1Δ63 (Designation: BY4710) and MATα, trp1Δ63 (Designation: BY4711). The wild-type, diploid yeast strain, INVSc1, was obtained from Invitrogen. Knockout of the indicated genes was verified by PCR using synthesized primers specific to the MNN1, OCH1, MNN4 and PMR1 genes (see sequences in the Yeast Deletion Project at worldwide web at sequence.stanford.edu/group/yeast_deletion_project), and to the KanMX4 cassette (KanB, 5'-CTG-CAGCGAGGAGCCGTAAT-3' (SEQ ID NO:8) and KanC, 5'-TGATTTTGATGACGAGCGTAAT-3' (SEQ ID NO:9)). Colony PCR was conducted as described (Giaever, 2002) using JumpStart™ Taq DNA Polymerase (Sigma). All yeast cultures were grown in YPD (1% Bacto®-yeast extract, 2% Bacto®-peptone, 2% glucose) or YPD+0.3M KCl, supplemented with 200 μg/ml G418 (Invitrogen) as indicated. Selection of diploids and haploids was conducted using CSM-met-lys plates (0.67% yeast nitrogen base without amino acids, 0.07% CSM-met-lys dropout mix, 2% glucose, 2% Bacto®-agar), supplemented with 20 μg/ml L-methionine (CSM-lys) or 50 μg/ml L-lysine-HCl (CSM-met). CSM-met-lys Dropout Mix was obtained from QBioGene. For yeast mating type tests, strains were selected on SD plates (0.67% yeast nitrogen base without amino acids, 2% glucose, 2% Bacto®-agar).

Yeast mating. Yeast strain 10322 (Δmnn1) was mated with strains 7034 (Δmnn4), 4406 (Δoch1), and 14534 (Δpmr1) to form the diploid strains DIP-mnn1mnn4 (MATa/α; his3Δ1/his3Δ1; leu2Δ0/leu2Δ0; LYS2/lys2Δ0; met15Δ0/MET15; ura3Δ0/ura3Δ0; mnn4:kanMX4/MNN4; MNN1/mnn1:kanMX4), DIP-mnn1och1 (MATa/α; his3Δ1/his3Δ1; leu2Δ0/leu2Δ0; met15Δ0/MET15; LYS2/lys2Δ0; ura3Δ0/ura3Δ0; och1:kanMX4/OCH1; MNN1/mnn1:kanMX4), and DIP-mnn1 pmr1 (MATa/α; his3Δ1/his3Δ1; leu2Δ0/leu2Δ0; LYS2/lys2Δ0; met15Δ0/MET15; ura3Δ0/ura3Δ0; pmr1:kanMX4/PMR1; MNN1/mnn1:kanMX4). The diploids were selected on CSM-met-lys and sporulated as described (Giaever, 2002). The ascus of the sporulated diploids were digested with Zymolyase 100T (US Biological) and random spore analysis was conducted as described in Current Protocols in Molecular Biology. Spores from DIP-mnn1mnn4 and DIP-mnn1pmr1 were plated on YPD, while spores from DIP-mnn1och1 were plated on YPD+0.3M KCl. The resulting haploid spores were selected for mating-type by crossing with parental strains (BY4710 and BY4711) on SD, and auxotrophic requirements by replica plating onto CSM-met and CSM-lys. The Δoch1 mutation was screened by slow growth on YPD at 37° C., while all ORF knockouts were screened and verified using colony PCR. The final double mutants were Δmnn1Δmnn4-9 (MATa, his3Δ1, leu2Δ0, met15Δ0, ura3Δ0, mnn1:kanMX4, mnn4:kanMX4), Δmnn1Δoch1-3 (MATα, his3Δ, leu2Δ0, lys2Δ0, ura3Δ0, mnn1:kanMX4, och1:kanMX4), and Δmnn1Δpmr1-5 (MATα, his3Δ1, leu2Δ0, lys2Δ0, ura3Δ0, mnn1:kanMX4, pmr1:kanMX4).

The haploid double mutants, Δmnn1Δmnn4-9 and Δmnn1Δoch1-3, were mated to form the diploid strain DIP-mnn1mnn4och1 (MATa/α; his3Δ1/his3Δ1; leu2Δ0/leu2Δ0; met15Δ0/MET15; LYS2/lys2Δ0; ura3Δ0/ura3Δ0; mnn1:kanMX4/mnn1:kanMX4; mnn4:kanMX4/MNN4; OCH1/och1:kanMX4), followed by sporulation, digestion, random spore analysis, and selection as before. The final, triple mutant haploids were: Δmnn1Δmnn4Δoch1-1-2, Δmnn1Δmnn4Δoch1-1-3, and Δmnn1Δmnn4Δoch1-2-5 (MATa, his 3Δ1, leu2Δ0, met15Δ0, ura3Δ0, mnn1:kanMX4, mnn4:kanMX4, och1:kanMX4); Δmnn1Δmnn4Δoch1-2-4 and Δmnn1Δmnn4Δoch1-2-6 (MATα, his3Δ1, leu2Δ0, lys2Δ0, ura3Δ0, mnn1:kanMX4, mnn4:kanMX4, och1:kanMX4); and Δmnn1Δmnn4Δoch1-2-2 (MATa, his3Δ1, leu2Δ0, lys2Δ0, ura3Δ0, mnn1:kanMX4, mnn4:kanMX4, och1:kanMX4). All clones were verified for KanMX knock-out of each ORF by PCR at the 3' and 5' ends (Giaevet, 2002).

The two haploid triple mutants, Δmnn1Δmnn4Δoch1-2-4 and Δmnn1Δmnn4Δoch1-2-5 were mated to form the diploid triple mutant, Δmnn1Δmnn4Δoch1-DIP (MATa/α; his3Δ1/his3Δ1; leu2Δ0/leu2Δ0; met15Δ0/MET15; LYS2/lys2 Δ0; ura3Δ0/ura3Δ0; mnn1:kanMX4/mnn1:kanMX4; mnn4:kanMX4/mnn4:kanMX4; och1:kanMX4/och1:kanMX4).

Preparation of Immune Sera:

Antibody against yeast zymosan. Rabbits were immunized using a yeast cell wall extract, zymosan A, which is composed of β-glucan and α-mannan of wild-type yeast. Two rabbits were immunized with 200 μg of zymosan A containing CFA at week 0, and boosted with 100 μg of antigen containing IFA at weeks 2 and 4, and thereafter every 4 weeks. Immune sera were collected at week 5, and 1 week after each booster. The resulting sera were pooled and purified with Protein A-agarose.

Antibodies against yeast glycoproteins. Synthetic peptides were used to generate immune sera in rabbits against the yeast proteins of interest. An accelerated immunization schedule was used, with an initial immunization of 200 μg at the outset and 100 μg immunizations at week 2, 4, 6 and 10, and test bleeds taken at week 5, 7, 8, and 11. The sequences of the peptides used are listed: CDSLESITDSLNLQSLT (SEQ ID NO:10) for PST1, CDSIKKITGDLNMQE (SEQ ID NO:11) for ECM33, CAVNGVTSKSALESIFP (SEQ ID NO:12) for Gp38, CTPKEQLSFVMNLYYEKSGGSKSD (SEQ ID NO:13) and CPATGKYWSAATELPPTPNG (SEQ ID NO:14) for Gas1, CPAMPSAASAYFTSGAGSPMGT-GIATQQS (SEQ ID NO:15) and CEIKGNAFFNSESGER-FYIRGVDYQPGGS (SEQ ID NO:16) for Gas5, and CSG-PQSYQKLDFTNVGFTGS (SEQ ID NO:17) and CEVGDRVWFSGKNAPLADY (SEQ ID NO:18) for YJL171c. Antigen specific antibodies were purified by immunoaffinity chromatography using the antigenic peptide coupled SulfoLink® Gel (Pierce).

Antibody specific to α1,3-linked mannose. Immune sera specific to α1,3-linked mannose residues was prepared as previously described, with slight variations (Raschke et al., J. Biol. Chem. 248(13):4660-6, 1973 and Ballou, J Biol. Chem. 245:1197-1203, 1970). Briefly, log phase INVSc1 cells suspended in 0.9% NaCl at $3.0 \times 10^7$ cells/ml were heat-killed at 70° C. for 90 min. Rabbits were injected with this suspension in the marginal ear vein three times a week at 0.25 ml, 0.5 ml, 0.75 ml and 11.0 ml for week 1, week 2, week 3, and week 4, respectively. Three days after the last injection, the rabbits were bled. The resulting sera were then adsorbed to Δmnn1 yeast cells. Each 5 ml of sera was incubated with 5 g (wet weight) of heat-killed Δmnn1 yeast in 50 ml of 0.9% NaCl. Sodium azide was added to 0.2% and the suspension was incubated overnight at room temperature with end-over-end mixing. The cells were removed by centrifuging at 6,000 g for 20 min and the adsorption was repeated. The final sera were dialyzed against 0.9% NaCl and sterilized with a 0.2 micron filter.

Determination of Carbohydrate Types on Yeast Whole Cells.

Materials. 2G12 monoclonal antibody was purchased from Polymum Scientific Inc. (Forschung GmbH). Protein A-Sepharose® 4B conjugate was purchased from Invitrogen (Carlsbad, Calif.). Goat anti-Rabbit IgG HRP was purchased from Jackson ImmunoResearch (West Grove, Pa).

Immunofluorescence. Log-phase Δmnn1Δmnn4Δoch1-DIP and INVScI cells grown at 30° C. in YPD+0.3 M KCl were fixed with 1 ml fresh 4% paraformaldehyde for 1 h and pelleted by centrifugation. The cells were washed once with PBS and transferred to polylysine-coated slides. After air-drying, the cells were incubated with 0.5% SDS at room temperature (RT) for 15 min. For single staining, rabbit anti-Zymosan antibody was diluted to 10 μg/ml and α1,3 -linked mannose anti-serum was used at a 1:500 dilution. These antibodies were incubated with the cells for 1 h at RT. The slides were washed and incubated for 1 h at RT with the secondary antibodies, Alexa Fluor® 568-conjugated goat anti-rabbit IgG (Molecular Probe, USA). Cells were washed with PBS and mounted onto slides. For co-localized staining, the anti-Zymosan and 2G12 antibodies were diluted to 10 μg/ml and 20 μg/ml, respectively, and incubated with the cells for 1 h. The slides were washed, probed, and mounted onto slides as above, using Alexa Fluor® 568-conjugated goat anti-human IgG and Alexa Fluor®-conjugated goat anti-rabbit IgG as secondary antibodies. Images were obtained using a Zeiss Axioskope fluorescence microscope (McBain, USA).

Whole-cell ELISA. Enzyme-linked immunosorbent assays (ELISA) were performed on heat-killed, whole yeast cells. Log-phase Δmnn1Δmnn4Δoch1-DIP and INVScI cells were heat-killed at 70° C. for 1 h in 0.9% NaCl and diluted to $5.0 \times 10^7$ cells/ml in PBS for coating ELISA plates. HIV-1 gp120 from SF162 strain (ARRRP) and wild-type yeast mannan (Sigma) were diluted to 5 μg/ml in 50 mM carbonate buffer, pH 9.5. One-hundred microliters of the antigens were incubated in each well overnight at RT. Wells were blocked with ELISA blocking buffer (PBS, 0.1% BSA, 0.02% thimerosal) and incubated for 2 hrs at RT in a humid chamber. After two dH$_2$O rinses, 2G12 and anti-α1,3-mannose antibody were added at 10 μg/ml with a three-fold serial dilution in blocking buffer and incubated overnight at room temperature. Wells were washed with ELISA wash buffer (PBS, 0.05% Tween® 20, 0.02% thimerosal) and incubated at 37° C. for 1 h with a 1:10,000 dilution of goat anti-human IgG-HRP or goat anti-rabbit IgG-HRP (Jackson ImmunoResearch) for 2G12 or anti-α1,3-mannose, respectively. Wells were washed as before, incubated with TMB for color development, and stopped with HCl. HRP activity was read by absorbance at 450 nm using an EMax® Microplate Reader (Molecular Devices).

Glycan profiling. Log-phase Δmnn1Δmnn4Δoch1-DIP cells grown at 30° C. were diluted to ~3.0×10$^7$ cells/ml in 0.9% NaCl. Cells were heat-killed at 70° C. for 1 h. N-linked glycans from cell were released by PNGase F digestion. Released N-linked glycans were permethylated and analyzed by Maldi-TOF Mass Spectrometry (MS) by Glycotechnology Core Resource at UCSD.

Identification and Confirmation of 2G12 Cross-Reactive Glycoproteins

Western blot. Yeast cells from strains of INVSc1, Δmnn1, Δmnn4, Δoch1, Δmnn1Δmnn4, Δmnn1 Δoch1 and Δmnn1Δmnn4Δoch1 were grown at 30° C. in YPD+0.3 M KCl to an OD$_{600}$ of 3.0. Yeast cells were centrifuged at 14,000 g for 2 min. The culture supernatant was subjected to acetone precipitation, by incubating with two-volumes of ice-cold acetone for 30 min at −80° C. The samples were centrifuged at 14,000 g for 15 min and the supernatant was removed. After air-drying for 15 min, the pellet was boiled for 5 min with 2× Laemmli SDS-sample buffer at 1/10 the original sample volume.

The yeast cell lysate was prepared by lysing in RIPA buffer. Briefly, each 1 ml of cell pellet is resuspended in 100 μl ice-cold RIPA buffer (150 mM NaCl, 10 mM Tris pH7.4, 1 mM EDTA pH 8.0, 1% Triton X-100, 1% DOC, 0.1% SDS, 1 mM PMSF, 1 μg/ml Aprotinin, and 1 μg/ml Leupeptin), and cell walls were broken by vortexing with acid-washed glass beads (Sigma) for 10 min. The resulting lysate was centrifuged at 13,000 g for 30 min to remove any debris and the protein concentration of each was diluted to 0.3 mg/ml in dilution buffer (50 mM Tris pH7.4, 1 mM EDTA pH8.0, 1 μg/ml Aprotinin, 1 μg/ml Leupeptin, and 0.1% SDS). Laemmli SDS-buffer is added to 1× and the samples containing 0.24 mg/ml protein were boiled for 5 min.

The supernatant and cell lysate fraction were subjected to SDS-PAGE separation on 4-20% gradient gels and transferred to nitrocellulose membranes at 250 mA for 2 hrs. Western blotting was conducted using the primary antibodies including MAb 2G12 and polyclonal antibodies raised in rabbits as described above followed by the secondary antibodies, goat anti-human IgG-HRP and goat anti-rabbit IgG-HRP (Jackson ImmunoResearch), at the indicated dilutions. Chemilluminescent detection was employed using ECL (GE Biosciences).

Partial purification of 2G12 cross-reactive proteins. The subcellular localization of endogenous yeast proteins was estimated using differential centrifugation as described in Current Protocols in Cell Biology. Log-phase cells from INVSc1 and Δmnn1Δmnn4Δoch1-DIP strains were grown as described above to an OD$_{600}$ of 3.0. Each 1 ml of cell pellet was resuspended in 100 μl sucrose lysis buffer (0.4 M sucrose, 2 mM EDTA, 25 mM imidazole, pH7.0, 1 mM PMSF, 1 μg/ml Aprotinin, and 1 μg/ml Leupeptin). An equal volume of acid-washed glass beads (Sigma) were added and cell walls were broken with 15 min of high-speed vortexing alternated with ice-bath incubation. The lysates were centrifuged at 500 g for 5 min to pellet the unlysed cells and large aggregates, and the supernatant was centrifuged at 22,000 g for 30 min. The resulting supernatant that contains cytoplasmic, Golgi complex and endosomal proteins was saved for analysis. The pellet, containing mostly vacuolar, nuclear, ER and plasma membrane proteins, was resuspended in a similar volume of PBS+1.0% Triton to solubilize the membrane proteins. The fraction was centrifuged as above to segregate the soluble and insoluble membrane fractions.

Lectin affinity chromatography. For Concanavalin A (ConA) lectin affinity chromatography, 9.5 ml of Triton-soluble membrane fraction was incubated overnight at 4° C. with 1 ml of ConA-agarose (Vector Labs) in 5 ml of Triton wash buffer (20 mM Tris, pH7.0, 50 mM NaCl, 10 mM CaCl$_2$, and 1% Triton X-100). The column was washed extensively with Triton wash buffer. To elute ConA-bound proteins, 5 ml of Triton wash buffer including 0.5 M methyl manno-pyranoside was added to the column followed by 5 ml of Triton wash buffer including 0.2 mM EDTA and 1.0% SDS.

For purification from the culture supernatant, 300 ml of Δmnn1Δmnn4Δoch1-2-5 yeast supernatant with 10 mM CaCl$_2$ was loaded on a 5 ml ConA-agarose column (Vector Labs) and washed extensively with ConA wash buffer (20 mM Tris, pH7.0, 50 mM NaCl, 10 mM CaCl$_2$), followed by ConA wash buffer including 0.5M methyl manno-pyranoside. To elute ConA-bound proteins, 5 ml of 2× SDS loading buffer was added to the column and boiled for 5 min.

Two-dimensional gel electrophoresis and mass spectrometry. ConA-agarose purified protein fractions were precipitated with TCA and resolubilized in 200 μl Urea/Thiourea Rehydration Solution (7 M urea, 2 M thiourea, 2% CHAPS, 60 mM DTT; 1% Ampholytes pH 3-10; 0.01% Bromophenol blue). IPG ZOOM® 4-7 IPG strips (Invitrogen) were rehydrated overnight with 120 μl of sample and 20 μl of rehydration buffer (7 M urea, 2 M thiourea, 2% CHAPS, 60 mM DTT, 1% Ampholytes pH 3-10, 0.01% Bromophenol blue) for the sypro® ruby gel, and 80 μl of sample and 60 μl of rehydration buffer for the Western blot. The strips were loaded on the ZOOM® IPG Runner (Invitrogen) and focused as follows: 200V for 30 min, 450V for 25 min, 750V for 25 min, and 2000V for 60 min.

For the second dimension, the IPG strips were reduced twice in LDS-equilibration buffer containing DTT for 15 min on an orbital shaker. Then, the strips were alkylated in LDS-equilibration buffer containing iodoacetamide for 15 min and electrophoresed on the IPG ZOOM® system using 4-12% gradient acrylamide gels with an MES running buffer. The gels were electrophoresed until the dye front migrated to approximately 0.3 cm from the bottom of the gel.

For Sypro® Ruby staining, the gel was fixed in 40% methanol, 10% acetic acid for one hour and stained overnight with Sypro® Ruby fluorescent stain. The gel was destained for 120 min in 10% methanol, 6% acetic acid with one change of destaining solution and imaged on the Molecular Imager PharoxFX laser imager with the following parameters: and excitation wavelength of 532 nm, an emission wavelength of 605 nm, and a resolution of 100 μm.

For the Western blot, the gel was soaked in transfer buffer (Invitrogen) immediately following the second dimension run. Proteins were transferred to nitrocellulose and probed with 2G12 at 1 μg/ml.

The proteins on 2D blot detected by 2G12 were matched to the spots stained with Sypro® Ruby. The matching spots were sliced and subjected to in gel digestion with trypson. The digested peptides were analyzed by Nano-LC MS/MS. The above experiments were performed by Proteomic Research Services Incorporated.

Immunoprecipitation. Culture supernatant and cell lysate were prepared from log-phase Δmnn1Δmnn4Δoch1-2-5 as described above. These samples were pre-cleared by incubation with protein A-Sepharose® 4B conjugate at RT for 2 hrs. For antigen-antibody complex formation, 10 μg of 2G12 was added to either cell lysate or media sample, and incubated on a shaker at RT for 1 h. After incubation, 20 μl of protein A-Sepharose® 4B conjugate was added to antigen-antibody complex, and incubated again at RT for 1 h on a shaker. The samples were spun 10,000 g for 5 min and the supernatant was aspirated. The beads were washed twice with 800 µl of PBS and the bound proteins were eluted by boiling with 40 µl of 1× SDS sample buffer. All samples were loaded onto 4-20% gradient SDS-PAGE gels and blotted for Western analysis using antibodies against the identified yeast glycoproteins including ECM33, PST1, GP38, YJL171C, Gas1, and Gas5.

Bioinformatic Analyses of N-Linked and O-Linked Glycosylation Sites

Analysis of N-linked glycosylation sites. N-linked glycosylation sites in the yeast S. cerevisiae genome and on the glycoproteins identified in the study were analyzed using software that we developed recently.

Analysis of O-linked glycosylation sites. O-linked glycosylation sites on some proteins in the S. cerevisiae genome and on the glycoproteins identified in the study were analyzed using software NetOGlyc 3.1 that was developed by Center for Biological Sequence Analysis (CBS) at Technical University of Denmark, which is available at worldwide web at cbs.dtu.dk/services/netoglyc.

Cloning, Expression, Characterization of gp120 Produced in Yeast Triple Mutant.

Reagents. The pYES2/CT vector was obtained from Invitrogen and the pJR-FLsyngp120 and pYU-2 plasmids were obtained from the AIDS Research and Reference Program (ARRRP). Yeast Nitrogen Base Without Amino Acids and -Ura Dropout Mix were obtained from U.S. Biological. A rabbit polyclonal antibody against gp120 from HIV-1$_{IIIB}$ (anti-gp120-IIIB) was obtained from Virostat Inc. Another rabbit polyclonal antibody against HIV-1$_{YU-2}$ (anti-gp120-YU2) was produced in house using a synthesized peptide, CEQMHEDIISLWDQSLK (SEQ ID NO:19), and affinity purified using the peptide coupled to SulfoLink® Gel (Pierce).

PCR cloning of the α-mating factor and gp120. The signal sequence of the S. cerevisiae alpha-mating factor (MFα) was added upstream of the multiple cloning site (MCS) of the pYES2/CT vector. The MFα was cloned from total yeast DNA (extracted from INVSc1) by PCR using the primers MFα1-Kpn-5 (5'-ATGGTACCAAAGAATGAGATTTCCT-TCAATT-3' (SEQ ID NO:20)) and MFα 1-Bam-3 (5'-ATG-GATCCAGCTTCAGCCTCTCTTTTATC-3' (SEQ ID NO:21)), with KpnI and BamHI sites added, respectively. This fragment contains the Kex2 cleavage site to remove the signal sequence from gp120. PCR was conducted using T4 DNA Polymerase (Sigma) according the manufacturer's protocol. PCR products were purified, digested with BamHI and KpnI, and ligated into a similarly digested pYES2/CT plasmid using standard molecular biology techniques. The resulting plasmid was pYES2/CT-α.

The coding sequence for JR-FL was amplified from pJR-FLsyngp120 by PCR using the primers JRFL-Eco-5 (5'-TG-GAATTCTGTGGGTGACTGTATACTAT (SEQ ID NO:22)) and JRFL-Xba-3 (5'-TATCTAGACCCCACAGCGCGCT-TCTCCCT-3' (SEQ ID NO:23)), with EcoRI and XbaI sites added, respectively. The coding sequence for YU-2 was amplified from pYU-2 using the primers YU2-Eco-5 (5'-TGGAATTCTGTTGTGGGTCACAGTCTATTAT-3' (SEQ ID NO:24)) and YU2-Xba-3 (5'-ATTCTAGATTCTCTTTG-CACCACTCTTCT-3' (SEQ ID NO:25)), with EcoRI and XbaI sites added, respectively. The gp120 PCR products were cloned into the pYES2/CT-α using digestion with EcoRI and XbaI, as above. The final plasmids were pYES2/CT-α-JRFL (pJRFL-gp120) and pYES2/CT-α-YU2 (pYU2-gp120).

Lithium acetate transformation of Δmnn1Δmnn4Δoch1-2-5 yeast. The plasmids pJRFL-gp120 and pYU2-gp120 were used to transform Δmnn1Δmnn4Δoch1-2-5 yeast cells. Briefly, 1.5 ml of an overnight culture of yeast grown in YPD+0.3 M KCl was pelleted. All but ~50 µl of the supernatant was removed, and the cells were resuspended. Then, 2 µl of 10 mg/ml single stranded salmon sperm DNA (Sigma) was added, followed by 1 µg of pJRFL-gp120 or pYU2-gp120. After vortexing, 500 µl of PLATE mixture (40% PEG 4000, 100 mM LiAc, 10 mM Tris, pH 7.5, 1 mM EDTA) and 20 µl of 1M DTT were added, and the mixtures were incubated for 4 hrs at RT. The cells were heat shocked for 10 min at 42° C., pelleted, and resuspended in 100 µl of sterile dH$_2$O. Cells were plated onto -ura/glucose (2% glucose, 0.67% yeast nitrogen base without amino acids, 0.2% -Ura Dropout Mix, 2% Bacto®-agar). Plates were incubated at 30° C. until colonies appeared. PCR was used directly on the colonies to verify the presence of each plasmid using the primers MFα1-Kpn-5 and JRFL-Xba-3 for pJRFL-gp120 transformant, and MFα1-Kpn-5 and YU2-Xba-3 for pYU2-gp120.

Expression of gp120 proteins in Δmnn1Δmnn4Δoch1 yeast. Triple mutant yeast cells transformed with pJRFL-gp120 and pYU2-gp120 were grown to log phase in −ura/glucose media (2% glucose, 0.67% Yeast Nitrogen Base without amino acids, 0.2%-Ura Dropout Mix). The cells were centrifuged and washed twice with −ura/galactose media (2% galactose, 0.67% Yeast Nitrogen Base without amino acids, 0.2%-Ura Dropout Mix), and resuspended in −ura/galactose at an OD$_{600}$=0.4. The cells were grown at 30° C. and samples of the media were taken at different time points to test for protein induction.

Purification of Yeast Expressed Glycoproteins

Ammonium Sulfate Precipitation. PST1 protein in the yeast culture supernatant from Δmnn1Δpmr1 and gp120 expressed in transformed Δmnn1Δmnn4Δoch1, were collected and centrifuged (Beckman Coulter, Allegra™ 64R, rotor F0650) at 3000g, 4° C. for 10 min to remove any insoluble particles. The supernatant was transferred to a clean beaker, 10 mM EDTA was added and the pH was adjusted to pH 7.4 using 1 M Tris Base. Ammonium sulfate was slowly added while stirring until a final concentration of 55% saturation at 4° C. was reached. The solution was stirred for additional 30 min and centrifuged at 15,000×g at 4° C. for 30 min. The pellet was resuspended in 2 ml PBS and the insoluble material was removed by centrifugation at 15,000×g at 4° C. for 1 h. This material was designated AS55 precipitate. Ammonium sulfate was slowly added to the 55% AS supernatant while stirring until a final concentration of 90% saturation at 4° C. was reached. The pellet was resuspended in 2 ml PBS and the insoluble material was removed by centrifugation at 15,000×g at 4° C. for 1 h. This material was designated AS90 precipitate. The AS55 and AS90 precipitates were desalted into 5 mM Sodium Phosphate, pH 7.5 using 5 ml HiTrap® desalting column (GE Life Sciences) and protein concentration was adjusted to 1 mg/ml.

Immunoaffinity purification of yeast expressed gp120. Anti-gp120-IIIB was conjugated to cyanogen bromide-activated Sepharose® 4B (Sigma) according to the manufacturer's protocol at 5 mg antibody per 1 ml gel. After extensive washing of the columns with PBS, the AS55 sample from Δmnn1Δmnn4Δoch1 cells was incubated with the immunoaffinity column for 2 hours at room temperature. The flowthrough was collected and the columns were washed again with PBS. Bound proteins were eluted with 100 mM glycine, pH2.5 in 1 ml fractions containing 50 µl of 1M Tris, pH9.5. These fractions were tested for gp120 by Western blot using 2G12 and anti-gp120-YU2. The gp120 containing fractions were pooled and designated AS55-AP.

Cation-Exchange Chromatography. Separate chromatography was performed for different samples, with AS55-AP used for gp120 purification and AS90 used for PST1 purification. A 5 ml HiTrap® SP FF column (GE Life Sciences) was equilibrated with 5 mM Sodium Phosphate, pH 7.5. The samples were loaded at 1 ml/min onto the column and washed with 15 ml of 5 mM sodium phosphate, pH 7.5. Proteins were eluted with an 80-ml gradient of 0-500 mM NaCl in 5 mM sodium phosphate pH 7.5 at a flow rate of 1 ml/min. Fractions of 2 ml were collected throughout, and 3 μl samples were tested for the presence of desired glycoprotein employing a dot blot assay. Fractions exhibiting a significant amount protein were pooled and designated GP-IEC-55 and GP-IEC-90. These fractions were further purified using ConA purification of glycoproteins as described earlier. The proteins were eluted into 1M methyl mannopyranoside with a 60 min. incubation.

Gel Filtration Chromatography of Glycoproteins. As a final step, the two GP-IEC-55 and GP-IEC-90 fractions were desalted into the loading buffer (50 mM Tris, 150 mM NaCl, 5 mM 2-bME, pH 7.5) and concentrated by Amicon® Centricon® 30 (Millipore) to a final concentration of ~1 mg/ml. A 150 ml Sephacryl® S-HR-200 (GE Life Sciences) was equilibrated with the same buffer and the GP-IEC pools were loaded onto the column. Proteins were eluted with the loading buffer at a flow rate of 0.3 ml/min, 2 ml fractions were collected and 3 μl samples of each fraction were tested for the presence of a glycoprotein employing the dot blot assay. Fractions exhibiting significant amount of the glycoprotein were pooled and collectively designated GP-SHR200-55 and GP-SHR200-90. The following standards were used and co-eluted from the filtration column: IgG (MW150kD), AP (MW 140kD), Egg white avidin (MW68) and Streptavidin (MW 53).

Glycan profiling. The GP-SHR200-55 and GP-SHR200-90 fractions, containing purified gp120 PST1, respectively, were digested with PNGase F to release all N-linked glycans. These glycans were permethylated and analyzed by Maldi-TOF Mass Spectrometry (MS) by Glycotechnology Core Research Facility at UCSD.

Immunization and Preparation of Antibodies Specific to α1,2-Linked Terminal Mannose Raising antibody against α1,2-linked mannose using yeast whole cell. Immune sera specific to α1,2-linked mannose residues was prepared using the triple mutant (Raschke et al., *J. Biol. Chem.* 248(13):4660-6, 1973; and Ballou, *J Biol Chem.* 245:1197-1203, 1970). Briefly, log phase Δmnn1Δmnn4Δoch1-DIP suspended in 0.9% NaCl at 3.0×$10^7$ cells/ml were heat-killed at 70° C. for 90 min. Rabbits were injected with this suspension in the marginal ear vein three times a week at 0.25 ml, 0.5 ml, 0.75 ml and 1.0 ml for week 1, week 2, week 3, and week 4, respectively. Three days after the last injection from week 2, 3, and 4, the rabbits were bled. After four weeks of rest, the rabbits were injected with the same suspension in the marginal ear vein three times a week at 0.5 ml, 0.75 ml and 1.0 ml for week 9, week 10, and week 11. A fourth, final bleed was collected 3 days after the final injection. The resulting sera were tested for gp120 binding by ELISA and Western blot.

Raising antibody against α1,2-linked mannose using yeast cell extract. Immune sera specific to a 1,2-linked mannose residues was prepared using the membrane fractions of the triple mutant. Log-phase cells from Δmnn1Δmnn4Δoch1-DIP strains were lysed in sucrose lysis buffer (0.4 M sucrose, 2 mM EDTA, 25 mM imidazole, pH7.0, 1 mM PMSF, 1 μg/ml Aprotinin, and 1 μg/ml Leupeptin) using acid-washed glass beads (Sigma). Lysates were centrifuged at 500 g for 5 min to pellet the unlysed cells and large aggregates, and the supernatant was centrifuged at 22,000 g for 30 min. The resulting pellet, containing mostly vacuolar, nuclear, ER and plasma membrane proteins, was resuspended in a similar volume of PBS+1.0% Triton to solubilize the membrane proteins. The fraction was centrifuged as above to segregate the Triton-soluble and -insoluble membrane fractions. Four groups of two rabbits were immunized with these fractions, one group with the Triton-soluble fraction of wild-type (INVSc1), two groups with the Triton-soluble fraction of the triple mutant, and one group with the Triton-insoluble fraction of the triple mutant. An accelerated immunization schedule was used, with an initial immunization of 200 μg at the outset and 100 μg immunizations at week 2, 4, 6 and 10, and test bleeds taken at week 5, 7, 8, and 11. The resulting sera were tested for gp120 binding by ELISA and Western blot.

Adsorption of antisera to heat-killed, whole cell yeast. In order to enrich for antibodies specific to α1,2 linked mannose residues, any sera that showed gp120 binding were then adsorbed to Δoch1 and INVSc1 (WT) yeast cells. Each 1 ml of sera was incubated with 1.0-2.0 g (wet weight) of heat-killed Δoch1 and/or WT yeast in 5 ml of 0.9% NaCl. Sodium azide was added to 0.2% and the suspension was incubated overnight at room temperature with end-over-end mixing. The cells were removed by centrifuging at 6,000 g for 20 min and the adsorption was repeated. The final sera were dialyzed against 0.9% NaCl and sterilized with a 0.2 micron filter. Then, the antibodies were purified on Protein A-agarose (Invitrogen) and tested again for gp120 binding by ELISA and Western blot.

Affinity purification of antibodies against α1,2-linked mannose residues. In order to further purify antibodies specific to α1,2 linked mannose residues, the sera from any adsorbed antibodies that showed gp120 binding by ELISA were purified using ConA-eluted glycoproteins from the triple mutant. Briefly, the culture supernatant and cell lysate from Δmnn1Δmnn4Δoch1-2-5 cells were purified using ConA lectin affinity chromatography as described earlier. The proteins from each fraction (supernatant and lysate) were separately conjugated to cyanogen bromide-activated Sepharose® 4B (Sigma) according to the manufacturer's protocol at 10mg total protein per 1ml gel. After extensive washing of the columns with PBS, 10-20 ml of selected sera were filter sterilized and incubated with the media for 2 hours per 5 ml at room temperature. The flowthrough was collected and the columns were washed again with PBS. Bound antibodies were eluted with 100 mM glycine, pH2.5 in 1 ml fractions containing 50 μl of 1 M Tris, pH9.5. After dialysis against PBS, these antibodies were tested for gp120 binding by ELISA and Western blot.

Analysis of Immune Sera for gp120 Reactivity and Pseudovirus Neutralization

ELISA against gp120. Enzyme-linked immunosorbent assay (ELISA) was performed to test for gp120 specificity of anti-α1,2-linked mannose sera. Different HIV-1gp120 proteins (from various sources, including Dr. Doms' laboratory, ARRRP and commercial companies) were diluted to 3-5 μg/ml in 50 mM carbonate buffer, pH 9.5. One-hundred microliters of the antigens were incubated in each well overnight at RT. Wells were blocked with ELISA blocking buffer (PBS, 0.1% BSA, 0.02% thimerosal) and incubated for 2 hrs at RT in a humid chamber. After two $dH_2O$ rinses, 2G12 and anti-sera against Δmnn1Δmnn4Δoch1-DIP were added at varying dilutions in blocking buffer and incubated overnight at room temperature. Wells were washed with ELISA wash buffer (PBS, 0.05% Tween® 20, 0.02% thimerosal) and incubated at 37° C. for 1 h with a 1:10,000 dilution of goat anti-human IgG-HRP or goat anti-rabbit IgG-HRP (Jackson ImmunoResearch). Wells were washed as before, incubated with TMB for color development, and stopped with HCl. HRP activity was read by absorbance at 450 nm using an EMax® Microplate Reader (Molecular Devices). SF162 gp120 expressed in CHO cells was obtained through the NIH AIDS Research and Reference Reagent Program (ARRRP). ADA, JR-FL, and YU2 gp120 expressed in 293T cells were obtained from Dr. Doms at University of Philadelphia.

In a similar method used above, the binding affinity of gp120 proteins expressed in mammalian cells will be compared to the triple mutant yeast expressed by quantitative ELISA. An equal quantity of gp120-yeast (expressed in Δmnn1Δmnn4Δoch1) and gp120-293 (expressed in 293T cells), from different strains, will be used to coat microwell plates. Then, 2G12, anti-gp120-IIIB, and anti-gp120-YU2 will be used to probe. By capturing equivalent amounts of protein and serially diluting the binding antibodies, the binding affinities 2G12 toward each gp120 will be calculated and compared.

Neutralization assay. The 293T/17 cells were purchased from the American Type Culture Collection (Manassas, Va.) and maintained in Dulbecco's modified Eagle's medium (DMEM) with 10% fetal bovine serum. The plasmid pNL4-3.luc.R-E- was purchased from Dr. Landau's laboratory. The various HIV-1 env gp160 plasmid used to produce pseudoviruses were obtained from NIH AIDS Research Reference Reagent Program (NIH, ARRRP). The U87.CD4.CCR5 and U87.CD4.CXCR4 cells line expressing CCR5 and CD4 used for pseudovirus infectivity were a gift of Dr. Doms at University of Philadelphia.

For pseudoviruses, a 10 cm dish of 70-80% confluent 293T/17 cells were cotransfected with gp160 env-expressing plasmids and with the complementing viral genome-reporter gene vector, pNL4-3.Luc.E⁻R⁻ using calcium phosphate method according to manufacturer's instruction (Invitrogen). The culture supernatant containing recombinant viruses pseudotyped with Env proteins were harvested 48 h post-transfection, centrifuged, filtrated through 0.45 μm filters, and frozen at −80° C. To measure the pseudovirus infectivity, aliquots of harvested supernatant were used to infect 10,000 cells per 96 well plates of CCR5 (U87.CD4.CCR5) or CXCR4 (U87.CD4.CXCR4) expresssing cell lines. The luciferase activity from a single round infected cells was measured after 72 h of cell culture using the Bright-Glo™ Luciferase Assay System reagent (Promega, Madison, Wis.) and Veritas microplate luminometer (Turner Biosystems) equipment according to manufacturer. Mean relative light units (RLU) for triplicate wells were determined and pseudovirus stock ≧2×10⁵ rlu/ml was used for subsequent neutralization assay.

For the neutralization assay, animal serum or purified antibodies were assayed for neutralizing antibody (NAb) activity against HIV-1 virus using a single-round pseudotype reporter assay. Briefly, CCR5 (U87.CD4.CCR5) or CXCR4 (U87.CD4.CXCR4) express cell lines cells were plated at 10,000 cell/well on 96 flat bottom plate and cultured overnight. For testing with sera, samples were heat-inactivated for 45 minutes at 56° C. before use. The next day and on a separated 96 well flat bottom plate, 25 μl of appropriately diluted pseudovirus suspensions were mixed in triplicate with 25 μl of serially diluted antibody sample (this brings the final antibody concentration to 200 ug/ml or 50 ug/ml for purified antibody or to 1:5 dilution for plasma sample) and incubated for 1 h at 37° C. After incubation of antibody/virus mixture, the media was removed from pre-incubated plate cells; the antibody mixture was added to cells and incubated for four hours at 37° C. in $CO_2$ incubator. After incubation, the mixture was then removed from the cells, and replaced by fresh medium. The cells were harvested 72h postinfection by adding equal volume (usually 50-100 ul) of Bright-Glo™ Luciferase Assay System reagent (Promega, Madison, Wis.) to culture cells and luciferase activity (in RLU) was measured by using a Veritas microplate luminometer (Turner Biosystems) as prescribed by manufacturer. The percentage of inhibition was determined for each sample by averaging the luciferase activity measurement on tested sample wells (cell/antibody/virus), virus control (cell/virus), and cell control (cell only) wells using the following formula: [(virus control wells−test sample well)/(virus control well−cell control)× 100].

Example 2

Figure 10:
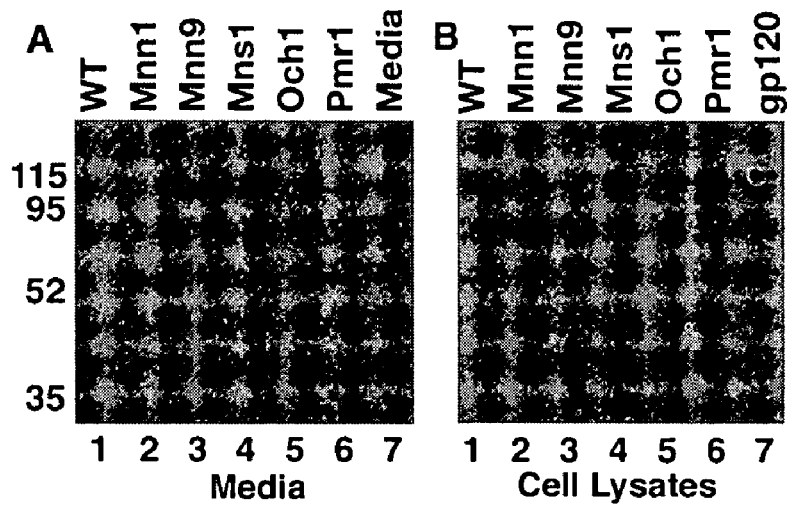
FIG. 10 shows screening 2G12 cross-reactive protein in yeast mutant strains using Western Blot. A. Yeast culture media from various mutant strains were screened with HIV-1 MAb 2G12 (Polymun Scientific Inc. Forschung GmbH). Secreted proteins in the culture media were precipitated with ethetone and loaded onto a 4-20% gradient SDS-PAGE gel. The blot was probed with 2G12 followed by incubation with horseradish peroxidase (HRP) labeled anti-human IgG. Signals were developed with ECL and exposed to X-ray film. B. Cell lysates were screened from the same set of yeast mutant strains with control of HIV-1 gp120 glycoprotein.
Figure 11:
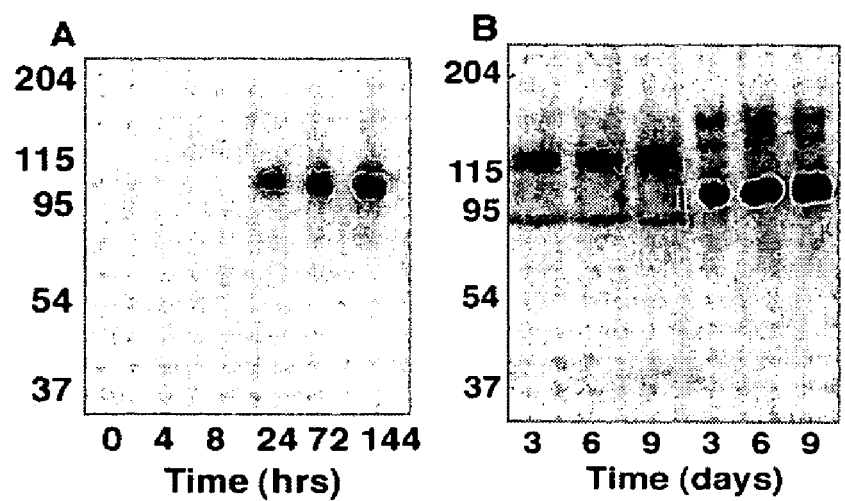
FIG. 11 shows induction of 2G12 cross-reactive protein in Δpmr1 yeast cells. A. gp120 transformed Δpmr1 yeast cells were cultured at the indicated time points. Secreted proteins in the culture media were precipitated with ethetone and loaded onto a 4-20% gradient SDS-PAGE gel. The blot was probed with 2G12 followed by incubation with HRP-anti-human IgG. Signals were developed with ECL and exposed to X-ray film. B. Proteins in the culture media from non-transformed (lanes 1-3) and gp120 transformed (lanes 4-6) Δpmr1 cells were detected with 2G12 as described in A.
Figure 12:
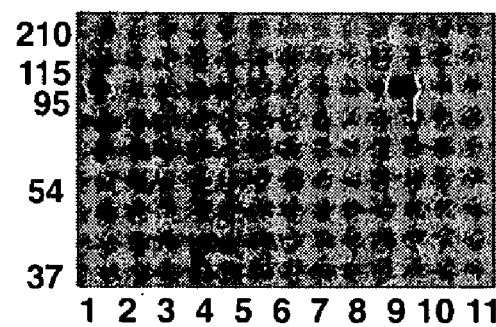
FIG. 12 shows purification and identification of the 2G12 reactive glycoprotein. The approximately 100 kDa protein (designated Yp100) was partially purified using GNL lectin affinity chromatography. The culture media were incubated with agarose bound GNL for 16 hrs. The samples of starting material (lane 1), flow through (lane 2), washes (lanes 3-6) and elutes (lanes 7-11) were loaded onto 4-20% SDS-PAGE gel. The proteins on transferred membrane were probed with MAb 2G12.

A Yeast Glycoprotein PST1 Cross-Reacts with 2G12 in a *S. Cerevisiae* Mutant Strain with PMR1 Gene Disrupted or Both pmr1 and mnn1 Genes Disrupted Screening 2G12 cross-reactive protein in yeast mutant strains. The glycosylation pathway of *S. cerevisiae* has been extensively studied. The deletion of nearly all ORFs in the *S. cerevisiae* genome (Winzeler et al., *Science* 285:901-906, 1999 and Giaever et al., *Nature,* 418:387-391, 2002), and the availability of each mutant strain, have provided an excellent opportunity to examine the changes in glycan profile in the yeast. Different mutants were first screened using 2G12 for possible cross-reactive glycoproteins in any of the mutants. As shown in FIG. 10, cell lysates and culture media from five single mutants with deletion of enzymes that are involved in the process of carbohydrate in ER and Golgi including Mns1, Och1, Mnn9, Mnn1, and Pmr1 were tested. The results show that two faint bands at approximately 100 and 120 kDa were detected in the cell lysate of the Δpmr1 mutant, although the signals are weaker than that from the HIV-1 gp120 glycoprotein (293T-expressed) used as a positive control.

The PMR1 gene encodes a high affinity $Ca^{2+}/Mn^{2+}$ P-type ATPase that is required for $Ca^{2+}$ and $Mn^{2+}$ transport into Golgi and involved in $Ca^{2+}$ dependent protein sorting and processing (Rudolph et al., *Cell.* 58:133-145, 1989). Deletion of PMR1 gene is thought to cause the secretion of some glycoproteins directly from the ER, thereby bypassing the Golgi apparatus and all glycan processing therein (Rudolph et al., *Cell.* 58:133-145, 1989). This would result in the lack of a polymannose outer chain and terminal α-1,3-linked caps on N-linked glycans (Verostek et al., *Glycobiology* 5(7):671-81, 1995). HIV-1 gp120 gene, from the YU-2 strain, containing the *S. cerevisiae* alpha-mating factor signal sequence was used to transform the Δpmr1 yeast. As shown in the FIG. 11A, an approximately 100 kDa protein in the media after 24 h culture was recognized by 2G12 in Western blots (herein dubbed YP100). In a parallel growth condition, the 2G12 reactive YP100 was shown in the media from transformed cells, but was not detectable in the media from non-transformed pmr1 mutant cells after 3 to 9 days culture (FIG. 11B). Several bands in the range of 90 to 160 kDa were shown in the non-transformed and transformed cells in this experiment but not shown in others. These results suggest that the gp120 plasmid transformation cause either an increase in expression or secretion of this protein.

The 2G12 reactive protein (YP100) in the gp120 transformed pmr1 mutant was initially thought to be the gp120 glycoprotein due to the following evidence: a 2G12 detectable band was induced by the transformation of gp120 plasmid (FIG. 2A, 11A), the band was detected in the gp120 transformed yeast cells but not in non-transformed cells (FIG. 11B), it showed an expected size at 96 to 100 kDa of glycoprotein (FIGS. 2A and 11), it showed an expected Endo H digested protein size at ~60 kDa, a similar molecular weight to the gp120 without glycosylation (FIG. 3). Further studies presented doubt that the induced YP100 protein was indeed gp120 since inconsistent results were observed using antibodies against gp120 (data not shown). As shown in FIG. 10, two faint bands at ~100 kDa and 120 kDa in the Δpmr1 yeast cell lysate were recognized by 2G12. These results indicate that the 2G12 reactive 100 kDa band has the possibility to be either expressed exogenous HIV-1 gp120 or an unknown endogenous yeast protein.

Identification of a 2G12 cross-reactive protein in Pmr1 mutant. To determine the protein recognized by 2G12 was gp120 or a yeast glycoprotein, Yp100 was partially purified using lectin affinity chromatography (FIGS. 2B and 12) and gel filtration. Proteins in the purified material were identified using Nano-LC-MS/MS. Six peptides were identified to belong to an unknown yeast protein, PST1 (FIG. 13), although some other peptides matched gp120 and yeast proteins. The PST1 protein contains a signaling peptide and a GPI anchor at its carboxy terminus indicating that it is a cell wall or membrane protein and can be secreted. There are 15 potential N-linked glycosylation sites in the 400 amino acids of mature protein, which accounts for a 3.8% density, indicating that PST1 is heavily glycosylated.

To confirm that Yp100 is indeed PST1, a polyclonal antibody was raised in rabbits against a synthetic peptide and purified using antigen immunoaffinity chromatography. The partially purified Yp100 protein was separated by 2D followed by Coomassie blue staining and Western blot analyses. FIG. 14A shows a predominant spot at molecular mass of 100 kDa and isoelectric point (PI) of 9-10. The same spot was identically recognized by 2G12 (FIG. 14B) and anti-PST1 polyclonal antibody (FIG. 14C). PST1 protein has a calculated PI of 9.25. All these results are consistent and suggest that the 2G12 cross-reactive glycoprotein is very likely the yeast glycoprotein PST1. These results present the first evidence of an endogenous yeast protein showing a binding affinity to the HIV-specific neutralizing antibody, 2G12.

To further confirm the 2G12 specificity of PST1, YP100 was digested with an enzyme, endo-L-N-acetylglucosaminidase H (Endo H), which specifically cleaves the high mannose type of glycans. As shown in FIG. 15 by Commassie blue and anti-PST1 antibody staining, after digestion, the migration of PST1 protein changed from ~100 kDa to ~60 kDa (compared lanes 2 and 4 with lanes 3 and 5). While the PST1 protein was still recognizable by anti-PST1 after Endo H digestion, it was no longer recognized by 2G12 (lane 7), which suggest that the N-glycans on the PST1 protein are the epitopes being recognized by HIV-1 neutralizing MAb 2G12. The molecular weight (~60 kDa) of PST1 after Endo H digestion in SDS-PAGE is higher than the calculated molecular mass (41 kDa) of amino acids from mature protein. This could be due to the O-linked glycosylation since PST contains potential O-linked glycosylation sites (FIG. 33). These results further confirmed that the 2G12-reactive protein shown in FIGS. 2 and 11 is actually a yeast glycoprotein PST1 with unknown function. This protein is induced by the transformation, of exogenous genes, at least, HIV-1 gp120 Env.

Generation of a double mutant and characterization of PST1 in the double mutant. The binding site of 2G12 on gp120 was identified as a conformation of terminal α1,2-linked mannose residues found on a cluster of at least three N-linked glycans. The Δpmr1 mutation in yeast is thought to bypass the Golgi, thus leaving only Man8 glycans on yeast proteins. However other evidence suggests that this mutation may only bypass the early Golgi compartment, or that the resulting change in $Ca^{++}$ affects the efficiency of the enzymes found in the Golgi. With this in mind, one of the most debilitating glycoslyation enzymes for 2G12 binding in the Golgi would be Mnn1p, which is responsible for all terminal α1,3-linked mannose capping of α1,2 residues (Nakajima at el, Proc Nat Acad Sci USA 72:3912-3916, 1975). In order to prevent this capping of PST1, a yeast double mutant strain, Δmnn1Δpmr1, was created. Yeast deletion strains with ORF knockouts in the MNN1 and PMR1 genes were mated and sporulated to produce a Δmnn1Δpmr1 haploid. Colony PCR was conducted for selection and verification of the Δmnn1 and Δpmr1 phenotypes (data not shown). Four unique primers per gene deletion confirmed that each ORF was completely deleted and replaced with the KanMX4 module.

Five double mutant strains (Δmnn1Δpmr1) were screened using Western blot with 2G12. As expected, the ~100 kDa band seen in the previous experiments (see FIG. 10) was detected by 2G12 in all five mutant strains (FIG. 16). In fact, there appears to be an enhancement of signal, which is likely due to the loss of terminal α1,3-Man caps and the exposure of more α1,2-Man on that protein. This hypothesis was confirmed by the following experimental study shown in FIGS. 17 and 18.

To analyze the effect of deletions of the genes involved in glycosylation pathway, size changes in PST1 protein in this double mutant, along with other yeast single mutants, were examined. Cell lysates (FIG. 17A, upper) and culture media (FIG. 17B, upper) from different strains were analyzed using Western blots with anti-PST1 polyclonal antibody. PST1 was only detected in the cell lysate of the Δmnn1Δpmr1 double mutant. The culture media shows the presence of a hyperglycosylated PST1 at >200 kDa in the wild type strain. PST1 in the Och1 mutant shows a significant migration shift to approximately 105 kDa, which migrated at similar size to that in pmr1 single mutant. These results suggest that the outer chain of high mannose on PST1 in the pmr1 mutant was not added, like in the och1 mutant. PST1 in the double mutant migrated even faster than it did in the pmr1 or och1, indicating a loss of terminal α1,3-Man on the $Man_8GlcNAc_2$ core in double mutant.

In contrast to PST1, another glycoprotein, GP38, was present in the cell lysate from all tested strains (FIG. 17A, lower). The size of this protein varied dramatically as the strains were mutated. Wild type and Δmnn1 showed a large, hyperglycosylated size of greater than 200 kDa. A band at ~90 kDa was shown in Δoch1 while a band at ~110 kDa shown in Δpmr1 suggesting a complete loss and truncation of hyperglycosylation in these two mutants, respectively. GP38 in pmr1 mnn1 double mutant showed a slightly smaller size than that in pmr1 single mutant, indicating the loss of the α1,3-linked mannose caps, which is consistent with PST1 seen in these two mutants. In addition, GP38 was detectable in media neither from wild type nor from mnn1 mutant (FIG. 17B, lower). Interestingly, it was strongly induced by mutation of pmr1 or och1. This further indicates that Pmr1p, similar to Och1p, plays a critical role in glycosylation, at least in some proteins. However, while the Δoch1 mutation almost guarantees the loss of hyperglycosylation, due to the deletion of the gene responsible for outer chain initiation, Δpmr1 appears to affect the efficiency of such chain elongation. This results in some proteins, like PST1, having a complete loss of hyperglycosylation, and other proteins, like Gp38, having reduced hyperglycosylation. The size changes of GP38 in pmr1 single mutant and pmr1 mnn1 double mutant showed the same pattern as PST1 in these two mutants indicating that the deletion of α1,3-Man that is added in the Golgi.

Figure 18:
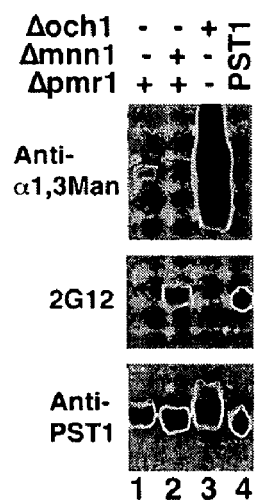
FIG. 18 shows analysis of α1,3-Man and α1,2-Man on PST1 in double mutant. Yeast cell culture media from pmr1 single mutant (lane 1) and pmr1+mnn1 double mutant (lane 2) were detected for terminal α1,3-Man and α1,2-Man by Western blot using anti-α1,3-linked mannose polyclonal antibody and 2G12. Och1 single mutant and purified PST1 were used as controls. Proteins in media were precipitated with acetone and loaded onto a 4-20% SDS-PAGE gradient gel. After blotting to nitrocellulose, the membranes were probed with 2G12 MAb, and rabbit anti-α1,3Man antibody or anti-PST1 antibody as indicated, followed by goat anti-human IgG-HRP and goat anti-rabbit IgG-HRP, respectively.

To confirm the loss of mnn1p function, the presence of terminal α1,3-Man and α1,2-Man were analyzed by Western blot with antibodies specific to each structure. FIG. 18 lower panel shows that the levels of PST1 expression in pmr1 single mutant and pmr1 mnn1 double mutant are similar. However, a band was detected by the anti-α1,3-Man specific polyclonal antibody in pmr1 single mutant while this activity was completely lost in the double mutant (FIG. 18, upper panel). In contrast, anti-α1,2-Man MAb 2G12 showed the opposite results. The 2G12 signal in the double mutant was much stronger than that in single mutant (FIG. 18, middle panel). In the och1 mutant, anti-α1,3-Man antibody, but not anti-α1,2-Man (2G12), detected a strong smear ranging from 70 to over 150 kDa indicating multiple glycoproteins with α1,3-Man structure are detected by anti-α1,3-Man antibody. The partially purified Yp100 showed reactivity to PST1 antibody and 2G12, but not to anti-α1,3-Man antibody.

2G12 MAb cross-reacts with both native and denatured PST1 glycoprotein. To test whether 2G12 recognizes the glycans on the native form of PST1, immunoblot was performed. Proteins in culture media from double mutant were precipitated with 2G12 followed by incubation with anti-human IgG-agarose. The immune complex was eluted using SDS-sample buffer and separated on 4-20% SDS-PAGE. Then the blot was probed with anti-PST1 polyclonal antibody. As shown in FIG. 19, strong signals were detected by anti-PST1 in the starting material (lane 1), flow through of preclear beats (lane 2), and elute (lane 6), but not detected, or weakly detected, in the supernatant and washes (lanes 3-5). These results indicate that 2G12 recognizes the native PST1 protein and has high affinity to the carbohydrate epitopes since most MAbs do not precipitate proteins.

Background Information of PST1 Gene and Protein:

Pst1p (protoplast secreted protein 1), belongs to the SPS2 family. It is a protein attached to the membrane by glycosylphosphatidyl inositol (GPI) anchor, and secreted by regenerating protoplasts. Pst1p is thought to be important for cell wall integrity due to it's upregulation upon activation of the cell integrity pathway, mediated by R1m1p, and it's upregulation by cell wall damage as mediated by Fks1p.

Gene and Family: Its precursor has 444 amino acids, with a predicted signaling peptide of 19 amino acids and a C-terminal domain of 25 amino acids for GPI anchor attachment. The molecular mass and isoelectric point of precursor are 45,776 Da and 9.91, respectively. It has a large number of N-linked glycosylation sites and rich in serine and threonine, which are likely to be heavily O-glycosylated. Its mature protein has 400 amino acids with predicted molecular mass of 41,260 Da and isoelectric point of 9.25. PST1 contains 15 potential N-linked glycosylation sites, which count 3.8% of the 400 amino acids. There are a total of 118 of serine and threonine residues, which count 29.5% of the 400 residues. Some of these serine and threonine are O-linked glycosylation sites (FIG. 33).

PST1 is most similar to Ecm33, showing a 58% identity and 79% similarity over the whole protein. The homologs of PST1 and Ecm33 were found in different species of yeasts and fungi but not in any other species including mammals, plants, insects, worms, and birds (FIG. 20). They have similar or overlapping activities, but they are not functionally redundant (Pardo M, *Microbiology,* 150:4157-4170, 2004).

Function: Molecular function of PST1 is unknown. It is involved in the cell wall organization and biogenesis. Both PST1 and Ecm33 are GPI-anchored cell wall proteins and localize to the cell surface.

Expression, induction, and secretion: PST1 (YDR055W) was initially found in the culture media of *S. cerevisiae* that was incubated in regenerating conditions with glusulase treatment to obtain protoplasts (Padro et al., Yeast, 15:459-472, 1999). Disruption of FKS1, one of subunits of glucan synthases, up-regulated the expression levels of YDR055W RNA and protein (Terashima et al., *Mol Gen Genet,* 264:64-74, 2000). The expression levels of its mRNA were found to be up-regulated by activation of MAP kinase, Mpk1/Slt2, or elevated temperature which cause environmental stresses that challenge the integrity of yeast cell wall (Jung et al., *Mol. Microbiol.* 34(5): 1049-57, 1999).

Taken together, a yeast glycoprotein was found to cross-react with HIV-1 broadly neutralizing MAb 2G12, which binds an epitope composed of Manα1,2-Man on high mannose type of glycan. This heavily glycosylated protein was identified to be PST1, a cell wall or membrane protein attached through GPI anchor. It is a secreted protein and up-regulated after transformation or deletion of the genes that are involved in the glycosylation pathway.

Example 3

Construction of Triple Mutants and Identification 2G12 Cross-Reactive Glycoproteins in Och1/Mnn1/Mnn4 Triple Mutant I. Construction and Characterization of Yeast Triple Mutant:

Yeast mating and verification of the Δmnn1Δmnn4Δoch1 triple mutant.

In order to explore the possibility of using yeast to produce glycoproteins similar to those found on gp120, the glycosylation pathway had to be mutated. Three proteins are vital for creating N-linked glycans that are specific to *S. cerevisiae*: OCH1p initiates the first α1,6 mannose residue necessary for hypermannosylation (Lehle, et al., *FEBS Lett.,* 370(1-2):41-5, 1995), MNN1p is responsible for all terminal α1,3-linked mannose capping of α1,2 residues (Nakajima et al, *Proc Nat Acad Sci* USA, 72:3912-3916, 1975), and MNN4p is a positive regulator of mannosylphosphorylation (Jigami, et al., *Biochim Biophys Acta,* 1426(2):335-45, 1999). Yeast deletion strains with ORF knockouts of these genes were mated and sporulated to produce Δmnn1Δmnn4 and Δmnn1Δoch1 haploids. Due to the temperature sensitivity exhibited by the Δoch1 phenotype (Lee, et al., *Proc Natl Acad Sci,* 97(22): 12679-84, 1999), selection of these clones was determined by slow growth on YPD at 37° C. Colony PCR was conducted for selection and verification of the Δmnn1 and Δmnn4 phenotypes (Data not shown).

The resulting double mutant haploids were mated and sporulated to produce the haploid, triple mutants, Δmnn1Δmnn4Δoch1. Screening of Δmnn4 and Δoch1 phenotype was conducted as before, using slow growth on YPD at 37° C. for Δoch1, and PCR for Δmnn4 and Δoch1. FIG. 23A shows a sample of the colony PCR screening for four clones, with three clones showing the presence of both the Δmnn4 and Δoch1 phenotype.

Six putative triple mutants were tested by PCR to verify the Δmnn1Δmnn4Δoch1 genotype. FIG. 21B shows the results for two of these clones, Δmnn1Δmnn4Δoch1-2-5 and Δmnn1Δmnn4Δoch1-2-6. Four unique ORF-specific primers per gene deletion confirmed that each gene was completely deleted. The combination of an internal ORF-specific primer (MNN1B, MNN4B, OCH1B, MNN1C, MNN4C and OCH1C) and an upstream or down stream primer (MNN1A, MNN4A, OCH1A, MNN1D, MNN4D and OCH1D) results in a PCR product if the ORF is present (i.e. MNN1A+ MNN1B, MNN1C+MNN1D, etc.). As seen in the figure, both clones showed no PCR product for both primer pairs against MNN1, MNN4 and OCH1, verifying the deletion genotype. Each ORF specific primer pair was also tested against WT as a positive control (results not shown).

By contrast, the combination of an upstream or downstream primer and an internal KanMX specific primer (KanB and KanC) results in a PCR product if the ORF has been replaced with the KanMX module. As seen in FIG. 23B, both of these clones show a PRC product at the expected size when tested with both primer pairs per gene deletion.

Two of the haploid triple mutants, Δmnn1Δmnn4Δoch1-2-6 and Δmnn1Δmnn4Δoch1-2-5, were mated to form the diploid triple mutant, Δmnn1Δmnn4Δoch1-DIP. This strain would be used for any future comparison studies to the wild-type diploid strain, INVSc1, including ELISA, immunofluorescence, and immunization.

Loss of α1,3-Mannose and Increase of 2G12 Cross-Reactivity in the Triple Mutant by ELISA.

The Δmnn1Δmnn4Δoch1 mutant yeast strain is expected to produce glycoproteins with a majority of Man$_8$GlcNAc$_2$ glycans. In order to indirectly verify the presence of these oligosaccharides, the triple mutant was tested for cross-reactivity to two mannose-specific antibodies, 2G12 and anti-α1,3-linked mannose (anti-α1,3). Immune sera specific to α1,3-linked mannose residues was prepared by immunizing rabbits with INVSc1 whole-cells and adsorbing the sera to Δmnn1 cells. Raschke et al., *J Biol Chem.* 248(13):4660-6, 1973; and Ballou, J Biol Chem, 245:1197-1203, 1970). The resulting sera are expected to be enriched for antibodies specific to the terminal α1,3-linked mannose residues used to cap α1,2-linked residues by Mnn1p. By contrast, 2G12 is known to be specific to the terminal α1,2-linked mannose residues found on the core N-linked glycan, albeit a cluster of such residues (Scanlan et al., *J Virol*, 76:7306-21, 2002).

Intact, whole yeast cells for WT (INVSc1) and Δmnn1Δmnn4Δoch1-DIP cells were used to coat ELISA plates, and 2G12 and α1,3 specific Ab were used to probe. As seen in FIG. 22A, the anti-α1,3 antibody showed a high affinity towards the wild-type cells, with the triple mutant showing low affinity. SF162 and wild-type yeast mannan were included as negative and positive controls, respectively. These results show the loss of terminal α1,3-linked mannose residues in the triple mutant. Any residual affinity of the anti-α1,3 towards the triple mutant can be attributed to the fact that the adsorption process is not completely efficient; other yeast-specific antibodies that are still present can bind to the epitopes exposed on the triple mutant (i.e. cell wall proteins and β-glucan).

FIG. 22B shows that 2G12 was able to bind to the triple mutant whole cells with no cross-reaction in binding to the wild-type. This affinity was seen between 10 μg/ml to ~1 μg/ml. SF162 and wild-type yeast mannan were included as positive and negative controls, respectively. These results not only confirm the loss of terminal α1,3-linked mannose residues in the triple mutant, but also show the resulting exposure of the α1,2-linked mannoses found on the core Man$_8$ glycan. More importantly, the ability of the Δmnn1Δmnn4Δoch1 yeast to bind to 2G12 implies the presence of 2G12-like epitopes on one or more proteins found on the yeast cell wall.

Loss of α1,3-Mannose and Increase of 2G12 Cross-Reactivity in the Triple Mutant by Immunofluorescence.

Figure 23:
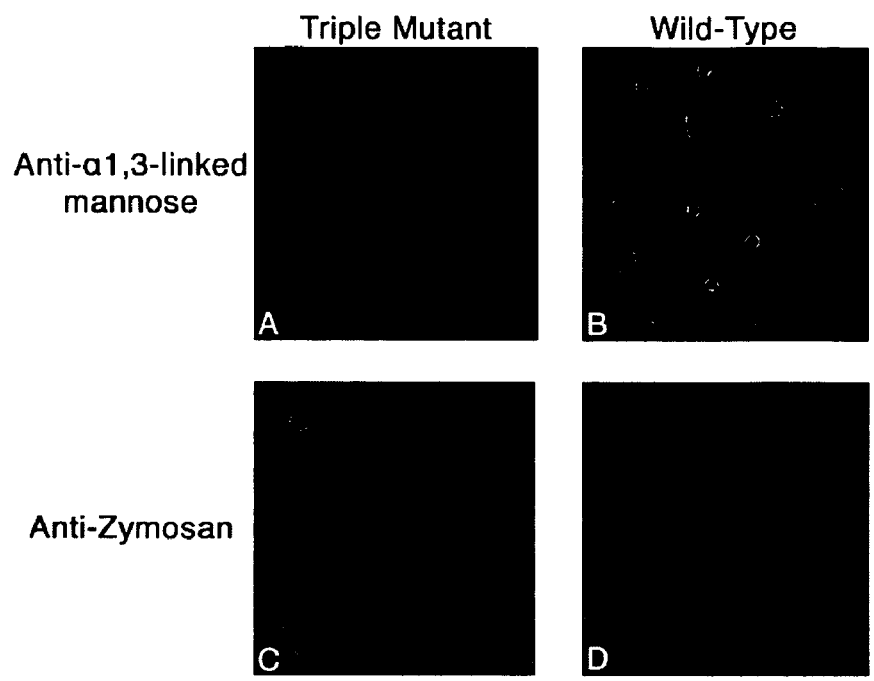
FIG. 23 shows loss of α1,3-Man reactivity in triple mutant cells. Immunofluorescence of triple mutant and wild-type yeast using anti-α1,3-linked mannose immune sera and anti-Zymosan antibody. Log-phase Δmnn1Δmnn4Δoch1-DIP cells (Panel A, C) and INVScI cells (Panel B, D) were fixed with 4% paraformaldehyde and transferred to polylysine-coated slides. The cells were incubated with 0.5% SDS and stained with α1,3-linked mannose antisera at a 1:500 dilution (Panel A, B) and purified anti-Zymosan at 10 μg/ml (Panel C, D), followed by Alexa Fluor® 568-conjugated goat anti-rabbit IgG.

Terminal α1,3 mannose residues in yeast not only cap α1,2-linked mannose residues, but are also highly immunogenic, making them divergent from the glycans found on HIV gp120. In order to further verify the loss of α1,3-linked mannose residues in the Δmnn1Δmnn4Δoch1 strain, we conducted immunofluorescence using anti-α1,3-Man on intact, whole cells. As shown in FIG. 23 (Panel A and C), the wild-type cell wall shows a strong reaction to the antisera specific to α1,3-linked mannose residues, while the diploid triple mutant shows no signal at the same dilution. As a control, antibodies specific to yeast Zymosan, which contains common components of the yeast cell wall, α-mannan and β-glucan, were found to give a similar signal to both the INVSc1 and Δmnn1Δmnn4Δoch1 whole-cells by immunofluorescence (FIG. 23, Panel B and D). These results indicate the loss of the α1,3-mannosyltransferase activity specific to the MNN1 protein. Such a loss would almost strictly leave α1,2-linked terminal mannose residues on all glycoproteins found in the cell wall of the triple mutant.

Figure 24:
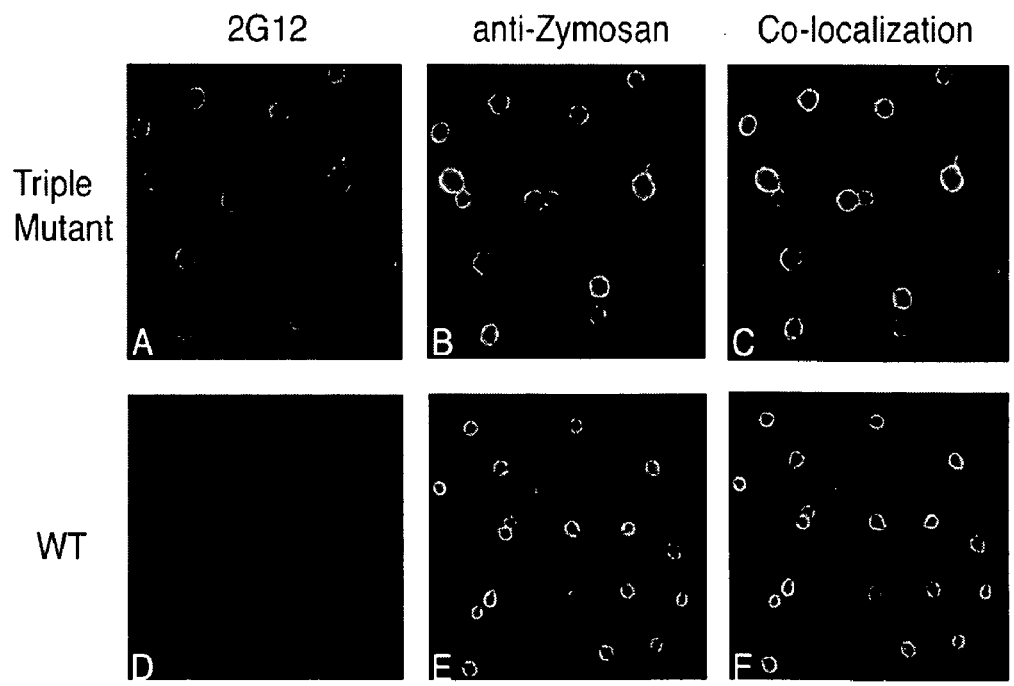
FIG. 24 shows exposure of terminal α1,2-Man in triple mutant cells. Immunofluorescence of Triple Mutant and wild-type yeast using 2G12 and anti-Zymosan. Log-phase Δmnn1Δmnn4Δoch1-DIP cells (Panel A, B and C) and INVScI cells (Panel D, E and F) were fixed with 4% paraformaldehyde and transferred to polylysine-coated slides. The cells were incubated with 0.5% SDS and stained with 2G12 at 100 μg/ml (Panel A, D) and rabbit anti-Zymosan at 10 μg/ml (Panel B, E), followed Alexa Fluor® 568-conjugated goat anti-human IgG and Alexa Fluor® 488-conjugated goat anti-rabbit IgG, respectively. Panel C and F show the co-localization of the antibodies.

To confirm this exposure of the α1,2-mannose residues on the triple mutant, 2G12 was then tested for co-localization with anti-Zymosan by immunofluorescence. FIG. 24 (Panel A, B, C) shows that 2G12 binds strongly to Δmnn1Δmnn4Δoch1-DIP cells and is co-localized with anti-Zymosan on the cell wall. The wild-type yeast only shows binding to anti-Zymosan, with no signal seen for 2G12 (Panel D, E, F). These data, similar to the whole-cell ELISA results, show that the glycoproteins found on the triple mutant contain exposed α1,2-linked mannose structures with the ability to bind 2G12 under native conditions. It is interesting to note that the sizes of the triple mutant yeast cells are noticeably larger than that of wild-type cells.

Loss of α1,3-Mannose and Exposure of α1,2-Mannose on Glycoproteins in the Triple Mutant by Western Blot.

Figure 25:
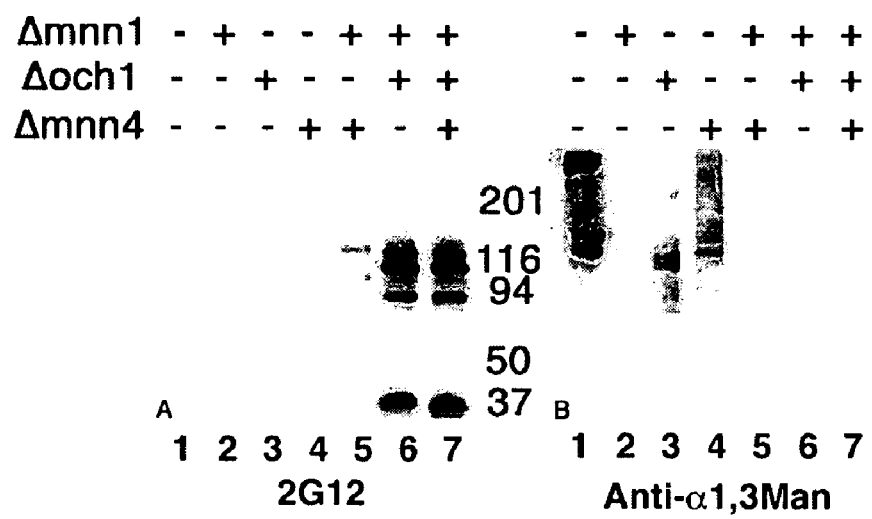
FIG. 25 shows analyses of α1,2-Man and α1,3-Man on the glycoproteins of yeast mutants. Western blot using 2G12 and α1,3-linked mannose antisera on all yeast glycosylation mutants. Log phase yeast cells were lysed in RIPA buffer and loaded onto a 4-20% SDS-PAGE gradient gel at 2.4 μg/lane. After blotting to nitrocellulose, the membranes are probed with 2G12 MAb or α1,3Man antisera, followed by goat anti-human IgG-HRP and goat anti-rabbit IgG-HRP, respectively. Lane 1 contains INVSc1 wild-type lysate. Lane 2 contains Δmnn1 lysate. Lane 3 is Δoch1 lysate. Lane 4 contains Δmnn4 lysate. Lane 5 contains Δmnn1Δmnn4 lysate. Lane 6 contains Δmnn1Δoch1 lysate. Lane 7 contains Δmnn1Δmnn4Δoch1 lysate. There are at least four proteins that bind strongly to 2G12 found in the cell lysate of Δmnn1Δoch1 and Δmnn1Δoch1Δmnn4 (Left Panel). By contrast, only WT yeast and mutant without the Δmnn1 genotype show binding to antisera specific to α1,3-linked mannose (Right Panel).

These 2G12-reactive proteins appear in the cell wall of Δmnn1Δmnn4Δoch1 yeast, but are absent in the wild-type. However, this does not directly implicate the exposed α1,2-linked mannose residues as the primary reason for affinity towards 2G12. Using Western blots, the presence of 2G12-reactive proteins among a panel of yeast glycosylyation mutants was tested. As seen in FIG. 25 left panel, only the lysate from the double mutant Δmnn1Δoch1 and the triple mutant Δmnn1Δmnn4Δoch1 showed specific protein bands that are detected by 2G12. In fact, both of these glycosylation mutants appear to have the same number of proteins (~4-5) that are reactive to 2G12. This, along with the lack of signal among the other yeast mutants, implies that the presence of core Man8 in Δmnn1Δmnn4Δoch1, and Δmnn1Δoch1 mutants plays an important role in the specificity of 2G12 toward these proteins. In addition, the lack of signal seen on the Δmnn1 and Δmnn1Δmnn4 mutant, which should have hyperglycosylated N-linked glycans with numerous exposed α1,2-linked mannose residues, further implicates the sole role of Man8 glycans in 2G12 binding.

This panel of yeast glycosylation mutants was also probed with anti-α1,3 to verify the presence or loss of α1,3-linked mannose caps. FIG. 25 right panel shows that the anti-α1,3-Man serum does not detect proteins on any mutant with the Δmnn1 phenotype, including Δmnn1Δoch1 and the triple mutant. This further implies the exposure of α1,2 epitopes on the triple mutant and the Δmnn1Δoch1 strain, along with the Δmnn1 and Δmnn1Δmnn4 strains, which 2G12 does not recognize. A second, identical Western blot was mock incubated (without a primary antibody) and showed no significant signal in any of the strains, thereby ruling out interaction with the goat anti-human secondary antibody (results not shown).

Figure 21:
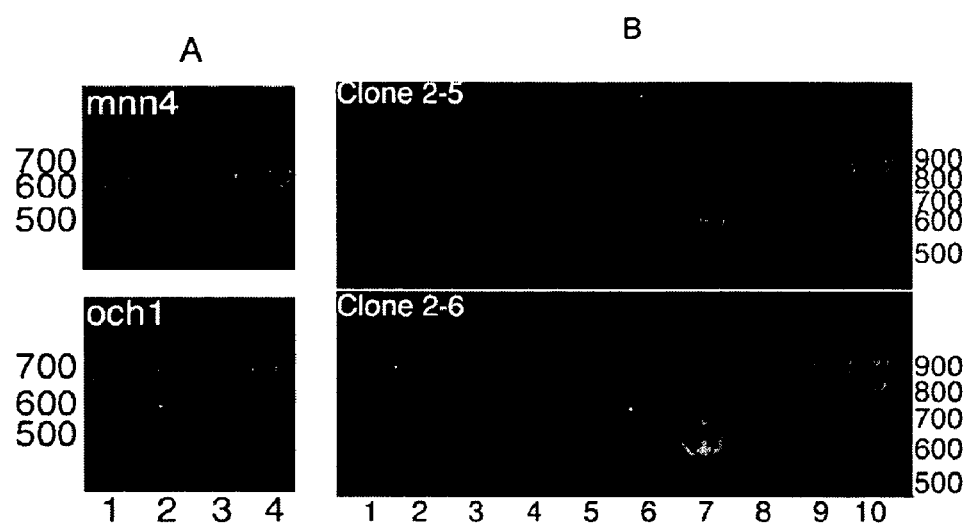
FIG. 21 shows analysis of double and triple mutants using PCR. Screening and verification of the genotype for triple mutant haploids. Panel A shows a 1.5% agarose gel with the PCR screening of putative triple mutants for the Δmnn4 genotype (top panel) using the MNN4A and KanB primers (expected size was 609 bp), and the Δoch1 genotype (bottom panel) using the OCH1A and KanB primers (697 bp). Lane 1 contains haploid clone 2-2. Lane 2 contains haploid clone 2-3. Lane 3 contains haploid clone 2-4. Lane 4 contains haploid clone 2-5. Panel B shows a 1.5% agarose gel with PCR verification of the Δmnn1, Δmnn4 and Δoch1 genotype for the triple mutant haploid clones 2-5 and 2-6 (top and bottom panels, respectively). Each lane contains a different pair of PCR primers, as indicated. The combination of an internal ORF-specific primer (MNN1B, MNN4B, OCH1B, MNN1C, MNN4C and OCH1C) and an upstream or down stream primer (MNN1A, MNN4A, OCH1A, MNN1D, MNN4D and OCH1D) result in no PCR product if the ORF is deleted. Lane 1 is MNN1A+MNN1B. Lane 2 is MNN4A+MNN4B. Lane 3 is OCH1A+OCH1B. Lane 4 is MNN1C+MNN1D. Lane 5 is MNN4C+MNN4D. Lane 6 is OCH1C+OCH1D. By contrast, the combination of an upstream or downstream primer and an internal KanMX specific primer (KanB and KanC) result in a PCR product if a deletion is present. Lane 7 is MNN1A+KanB (expected size of 591 bp). Lane 8 is MNN1D+KanC (944 bp). Lane 9 is MNN4D+KanC (931 bp). Lane 10 is OCH1D+KanC (854 bp).
Figure 26:
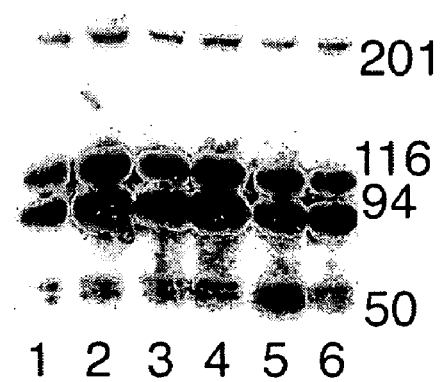
FIG. 26 shows 2G12 reactivity in all isolated triple mutants. Western blot using 2G12 on six yeast triple mutant clones. Log phase yeast triple mutant clones were crudely lysed in SDS loading buffer and loaded onto a 4-20% SDS-PAGE gradient gel. After blotting to nitrocellulose, the membrane was probed with 2G12 at 1 μg/ml followed by goat anti-human IgG-HRP. Lane 1 contains the haploid clone 1-2. Lane 2 contains the haploid clone 1-3. Lane 3 contains the haploid clone 2-2. Lane 4 contains the haploid clone 2-4. Lane 5 contains the haploid clone 2-5. Lane 6 contains the haploid clone 2-6. There are at least four proteins that bind strongly to 2G12 found in the crude cell lysate of each triple mutant haploid clone.
Figure 27:
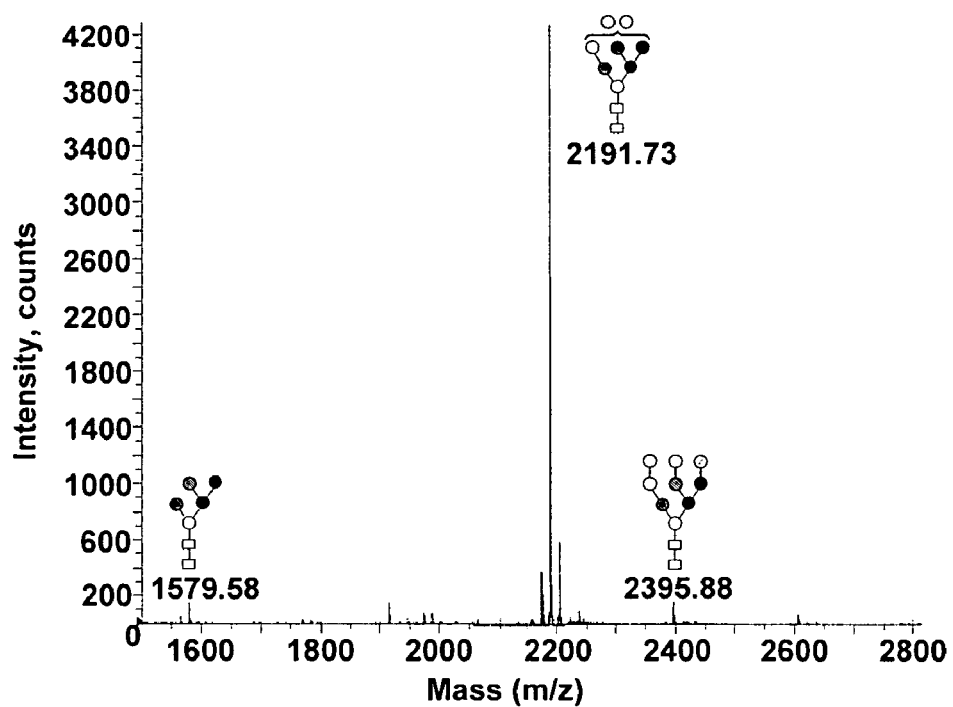
FIG. 27 shows homogenous of Man8 form of high mannose in yeast triple mutant cells. MALDI-TOF Mass Spectrometry of Triple Mutant Yeast Lysate. Log-phase Δmnn1Δmnn4Δoch1-DIP cells were homogenized, with lipid extraction, and the resulting lysate was digested with PNGase F. N-glycan profiling was conducted by Maldi-TOF Mass Spectrometry after permethylation. The major peak, which represents over 90% of the total glycans is $Man_8GlcNAc_2$, while there are two minor peak representative of $Man_5GlcNAc_2$ and $Man_9GlcNAc_2$.
Figure 28:
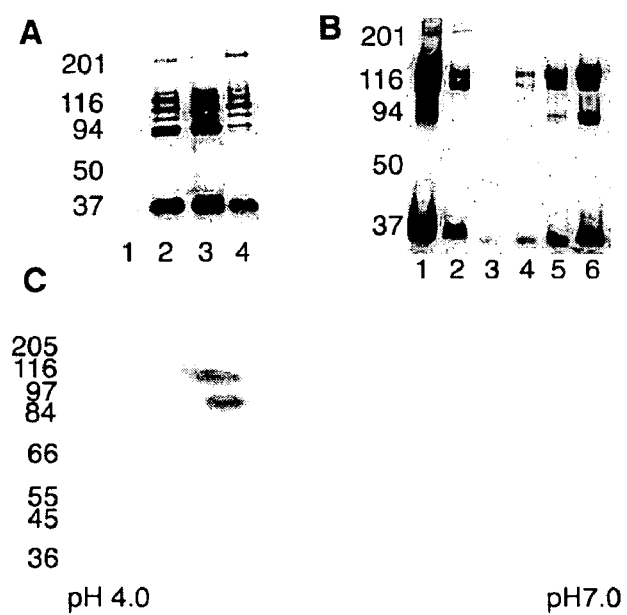
FIG. 28 shows partial purification and separation of 2G12-reactive proteins from the cell lysate of triple mutant yeast. In Panel A, the subcellular localization of 2G12-reactive proteins was estimated using differential centrifugation. Log-phase Δmnn1Δmnn4Δoch1 cells were lysed in sucrose lysis using glass beads. After removal of unlysed cells and large aggregates, the proteins were separated into two fractions, the 22,000 g supernatant (Lane 1) and the 22,000 g pellet (Lane 2). From this fraction, the pellet was resolubilized in 1.0% Triton X-100 and separated into two additional fractions, the Triton-soluble pellet (Lane 3) and the Triton-insoluble pellet (Lane 4). All lanes represent a Western blot using 2G12 at 1 μg/ml. In Panel B, the 2G12-reactive proteins were partially purified using ConA-agarose. The Triton-soluble fraction (Lane 1) from Δmnn1Δmnn4Δoch1 cells were incubated with ConA-agarose beads and the flowthrough was collected (Lane 2). After washing with binding buffer (Lane 3), proteins were eluted with either 0.5 M methyl manno-pyranoside (Lane 4, 5), or 2 mM EDTA+1.0% SDS (Lane 6). All lanes represent a Western blot using 2G12 at 1 μg/ml. In Panel C, the 2G12-reactive proteins were separated using 2D electrophoresis. The elute fractions from the ConA purification (Panel B, Lane 4-6) were run onto Invitrogen IPG ZOOM® 4-7 IPG strips followed by size separation on the IPG ZOOM® system using 4-12%. One gel was stained by Western blotting using 2G12 at 1 μg/ml. Two large spots that showed a positive signal by Western blot were excised from the Sypro® Ruby gel, digested with Trypsin, and analyzed by nano LC/MS/MS on a Micromass Q-Tof 2 for peptide identification. Three glycoproteins (ECM33, Gas1, and Gas5) in the upper spot and a single glycoprotein (YJL171c) in the lower spot were identified using MS/MS.

In order to verify that the reactivity of the triple mutant proteins towards 2G12 is due to the genotype of the yeast strain, and that no other protein with complementary function are expressed, different triple mutant clones were analyzed. A total of six Δmnn1Δmnn4Δoch1 yeast strains were obtained from the Δmnn1Δmnn4×Δmnn1Δoch1 cross. Each was picked from a separate haploid colony growing on YPD+KCl plates and was verified to contain the three deletions (see FIG. 21 for clones 2-5 and 2-6). In FIG. 26, all six clones show 2G12 reactivity to the same proteins by Western blot. This indicates that the reactivity of these proteins to 2G12 is most likely due to the genotype of the triple mutant resulting in mutated glycans.

Verification of the Glycans on the Triple Mutant.

As a final confirmation of the oligosaccharides present on the Δmnn1Δmnn4Δoch1 glycoproteins, MALDI-TOF and NP-HPLC profiling were conducted on N-linked glycans extracted from whole yeast cell extract. In FIG. 26, the MALDI-TOF results show that $Man_8GlcNAc_2$ is predominant glycan in the triple mutant extract, with a very minor amount of $Man_9GlcNAc_2$ and $Man_5GlcNAc_2$. The level of Man8 glycans is 20 times more than that of either Man9 or Man5, such that $Man_8GlcNAc_2$ represents over 90% of the total glycans in the triple mutant. The NP-HPLC results appear consistent with the MALDI-TOF, such that Man8 is the predominant N-linked glycan present in the Δmnn1Δmnn4Δoch1 cell extract.

Figure 29:
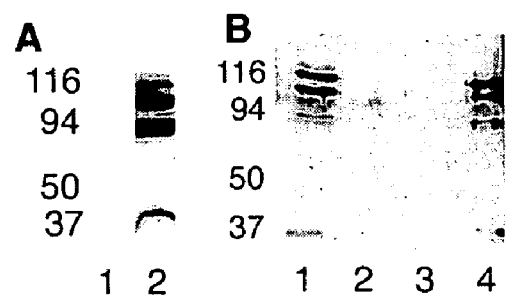
FIG. 29 shows expression and partial purification of 2G12-reactive glycoproteins in the culture media of triple mutant yeast. In Panel A, 100 μl of culture supernatant from log phase INVSc1 and Δmnn1Δmnn4Δoch1 yeast were subjected to acetone precipitation by incubating with two-times the volume of ice-cold acetone for 30 min at –80° C. The resulting pellets were resuspended in 10 μl of SDS sample buffer and loaded onto 4-20% SDS-PAGE gradient gels. After transfer to nitrocellulose, proteins were probed with 2G12 at 2 μg/ml. The triple mutant yeast has at least four proteins with strong reactivity to the 2G12 MAb (Lane 2), while the wild-type yeast supernatant shows no signal (Lane 1). In Panel B, the 2G12-reactive proteins were partially purified using ConA-agarose. The culture supernatant (Lane 1) from log-phase Δmnn1Δmnn4Δoch1 cells was directly incubated with ConA-agarose beads. The flowthrough (Lane 2) was collected and the beads were washed with binding buffer (Lane 3). The bound 2G12-reactive proteins (lane 4) were eluted by boiling the ConA beads with SDS-PAGE loading buffer. The proteins were detected by Western blot using 2G12 at 1 μg/ml. Two glycoproteins (ECM33 and GP38) were identified using MS/MS from an aliquot of 2G12 precipitates shown on lane 4.

Taken together, these results verify that the types of glycans present in the Δmnn1Δmnn4Δoch1 cells, are predominantly $Man_8GlcNAc_2$, similar to those found on core N-linked glycans. This indicates not only the loss of the highly immunogenic terminal α1,3-linked mannose residues, but also the loss of the hypermannosylated outer chain. The resulting exposure of terminal α1,2-linked mannose residues is most likely the reason behind the affinity of 2G12 for specific cell wall proteins found in this mutant.

II. Identification and Verification of 2G12 Cross-Reactive Glycoproteins in the Yeast Triple Mutant 2D Separation of 2G12-Reactive Proteins from Yeast Cells.

These proteins in Δmnn1Δmnn2Δoch1 yeast that show binding to 2G12 by ELISA, immunofluorescence and Western blot are promising antigens for the production of 2G12-like antibodies. They would represent the first such antigens produced in yeast with the ability to mimic the 2G12 epitope, which consists of a conformation of α1,2-linked mannose residues found on a cluster of N-linked glycans. Thus, this study was continued with the partial purification and identification of these proteins. Due to the predominance of glycoproteins in the cell wall and plasma membrane, differential centrifugation was used to largely separate the membrane-associated proteins from the cytoplasmic proteins. Log-phase Δmnn1Δmnn4Δoch1-DIP cells were lysed and subjected to centrifugation to remove cytoplasmic, Golgi complex and endosomal proteins. The pellet, containing mostly vacuolar, nuclear, ER and plasma membrane proteins, was resolubilized in 1% Triton X-100 to separate out the highly insoluble proteins. As seen in FIG. 28A, the 2G12-binding proteins were found mainly in the membrane fraction, and a small majority of these proteins were found to be soluble in Triton. These results are consistent with the whole-cell ELISA and immunofluorescence, in that these proteins appear to be mainly cell wall- or plasma membrane-associated.

In addition to being membrane-associated, previous results also implied that these 2G12-reactive proteins are highly glycosylated. Therefore, Concanavalin A (ConA) lectin affinity chromatography was used to purify the 2G12-reactive proteins found in the Triton-soluble fraction. FIG. 28B shows that these proteins have a high affinity for ConA, such that the majority of proteins cannot be fully eluted by competitive binding (using 0.5M methyl manno-pyranoside), requiring harsher conditions to elute (1% SDS).

The resulting proteins from the ConA eluate would represent the highly glycosylated membrane proteins found in the Δmnn1Δmnn4Δoch1 cells, including those that bind to 2G12. In order to efficiently separate these proteins for identification, 2-D gel electrophoresis was used on this fraction. Two separate aliquots were run onto pH4.0-7.0 IPG strips followed by SDS-PAGE separation on 4-12% gradient gels. One gel was stained by Sypro® Ruby while the other gel was transferred to nitrocellulose for a Western blot using 2G12. FIG. 28C shows that two large spots were identified by Western blot, which corresponded to two spots visualized on the Sypro® Ruby stained gel (not shown). These spots were excised for Trypsin digestion and nano LC/MS/MS identification. The higher 2D spot (at ~110 kDa) identified peptides from three yeast glycoproteins, Gas5 (5 peptides), ECM33 (4 peptides), and Gas1 (2 peptides). The lower 2D spot (at ~95 kDa) identified 7 peptides from a single yeast glycoprotein , YJL171c. These proteins represent all or most of the higher molecular weight proteins with 2G12-reactivity. There may be more such proteins at this size range that were not identified, but there is definitely an ~35 kDa protein (see FIGS. 25 and 28) that was not identified in this screen. The identity of this protein is not known, but is currently under investigation.

1-D Separation of 2G12-Reactive Proteins from the Culture Supernatant.

In addition to the cell lysate, the culture supernatant of the yeast triple mutant was found to contain glycoproteins with 2G12-reactivity. The culture media from INVSc1 and Δmnn1Δmnn4Δoch1 cells were tested for 2G12-reactivity by Western blot. FIG. 29A shows the expression of at least four bands with strong reactivity to the 2G12 MAb in the culture media of the triple mutant, while the wild-type yeast supernatant shows no signal.

These 2G12-reactive proteins in the media may represent secreted glycoproteins, or cell wall proteins released into the media, either naturally or due to changes in cell wall structure of the triple mutant. In fact, the sizes of these four proteins appear similar to the 2G12-reactive proteins found in the cell lysate (see FIGS. 25A & 28A), with a predominance of signal seen between 90 to 115 kDa and one band at ~37 kDa. This suggests that these could be the same proteins found in the cell lysate. Regardless, the fact that these proteins may represent other antigens that mimic the 2G12 epitope warrants their identification. The supernatant from Δmnn1Δmnn4Δoch1 yeast was applied directly to a ConA column for partial purification of the glycoproteins. The proteins in the culture supernatant showed a very high affinity to the ConA column and could not be eluted thought competitive binding using methyl manno-pyranoside. Therefore, the 2G12-reactive proteins were eluted by boiling the ConA beads with SDS-PAGE loading buffer (FIG. 29B). This SDS elute was separated using a large-format (10 cm×16 cm) 10% SDS-PAGE gel. A Coomassie blue stain of the gel showed five separate protein bands, each of which was excised from the gel (data not shown). These bands were tested for 2G12 reactivity by re-loading onto an SDS-PAGE minigel and probing with 2G12 by Western blot. Two protein bands (at 110 kDa and 95 kDa) were found to bind 2G12 (results not shown) and excised. These proteins were digested with Trypsin, and analyzed by nano LC/MS/MS on a Micromass Q-T of 2 for peptide identification. The 110 kDa band identified only one protein in the gel slice, with 4 peptides matching ECM33, the same protein identified by 2D at 110 kDa in the membrane fraction. The 95 kDa band identified only one protein in the gel slice, with 4 peptides matching the yeast glycoprotein, Gp38.

These two proteins probably represent only half of the 2G12-reactive proteins in the culture media (see FIG. 29A); in fact there are four bands that appear to be 2G12-reactive in the culture supernatant. These two unidentified proteins may be the same as those found in the cell lysate, or, like GP38, may represent unknown proteins with the ability to bind 2G12. These unidentified proteins are still under investigation.

Verification of 2G12-Reactive Proteins by Immunoprecipitation.

Figure 30:
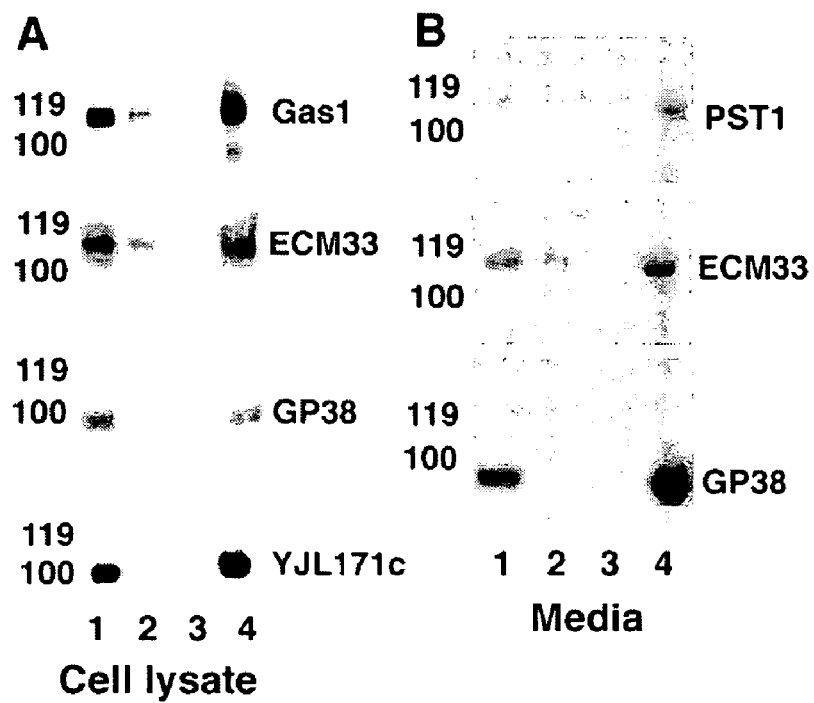
FIG. 30 shows immunoprecipitation of 2G12-reactive proteins. The cell lysate and culture media of triple mutant cells were immunoprecipitated with 2G12 and blotted with antibodies against the identified 2G12-reactive proteins. Cell lysate (Panel A) and culture media (Panel B) from Δmnn1Δmnn4Δoch1 cells (Lane 1) were pre-cleared by incubation with Protein A-Sepharose® 4B. 2G12 was added to the samples, incubated for 1 hour, followed by Protein A-Sepharose®. The unbound proteins were removed as the supernatant (Lane 2) and washed with PBS (Lane 3). Bound proteins were eluted by boiling with 40 μl of 1×SDS sample buffer (Lane 4). All samples were loaded onto 4-20% gradient SDS-PAGE gels and blotted for Western analysis using anti-ECM33, anti-gp38, anti-YJL171C, anti-Gas1, and anti-PST1.

The identification of ECM33, Gas1, Gas5, GP38 and YJL171c as 2G12-reactive yeast glycoproteins was conducted indirectly; LC/MS/MS was used to identify bands in gel electrophoresis that bound to 2G12 by Western blotting. In order to confirm the affinity of these proteins to 2G12, the cell lysate and culture media of $\Delta mnn1\Delta mnn4\Delta och1$ cells were immunoprecipitated with 2G12 and probed the resulting Western blots with antibodies against these proteins. FIG. 30A shows the identification of 4 proteins, Gas1, ECM33, YJL171c, and GP38, that were precipitated from the culture supernatant by 2G12. Gas1, ECM33 and YJL171c were identified in the cell lysate of the triple mutant by 2D separation, and show a similar size in both experiments, ~115 kDa, ~110 kDa, and ~95 kDa, respectively. GP38 was originally identified in the culture supernatant of the triple mutant, but here shows that can be also be precipitated from the cell lysate by 2G12. Gas5 was also precipitated with 2G12 with relatively low affinity (data not shown), which could be due to the less number and lower density of N-linked glycans than those from other identified proteins (FIG. 38).

FIG. 30B shows the identification of 3 proteins, PST1, ECM33, and GP38, with immunoblots. These proteins were precipitated from the culture supernatant by 2G12. ECM33 and GP38 were also identified in the culture media of the triple mutant by 1D separation, and show a similar size in both experiments, ~110 kDa and ~95 kDa, respectively. Interestingly, PST1 was originally identified as a 2G12-binding protein in the culture supernatant of $\Delta pmr1$ yeast (Example 2). It can be seen here that the expression level of PST1 is very low in the supernatant of the triple mutant (FIG. 30B, Lane1) when compared to ECM33 and GP38, which may explain why this protein wasn't originally identified in this mutant.

These results confirm the ability of ECM33, Gas1, Gas5, GP38, PST1 and YJL171c to bind 2G12 under the native conditions of this immunoprecipitation experiment. When analyzed with our previous experiments, it appears that these yeast glycoproteins have the ability to mimic the 2G12 epitope found on the HIV-1 gp120 glycoproteins, thereby causing binding to this antibody by Western blotting, immunoprecipitation, immunofluorescence and ELISA.

Glycoprotein Size Shifts for Two 2G12-Reactive Yeast Proteins.

Figure 31:
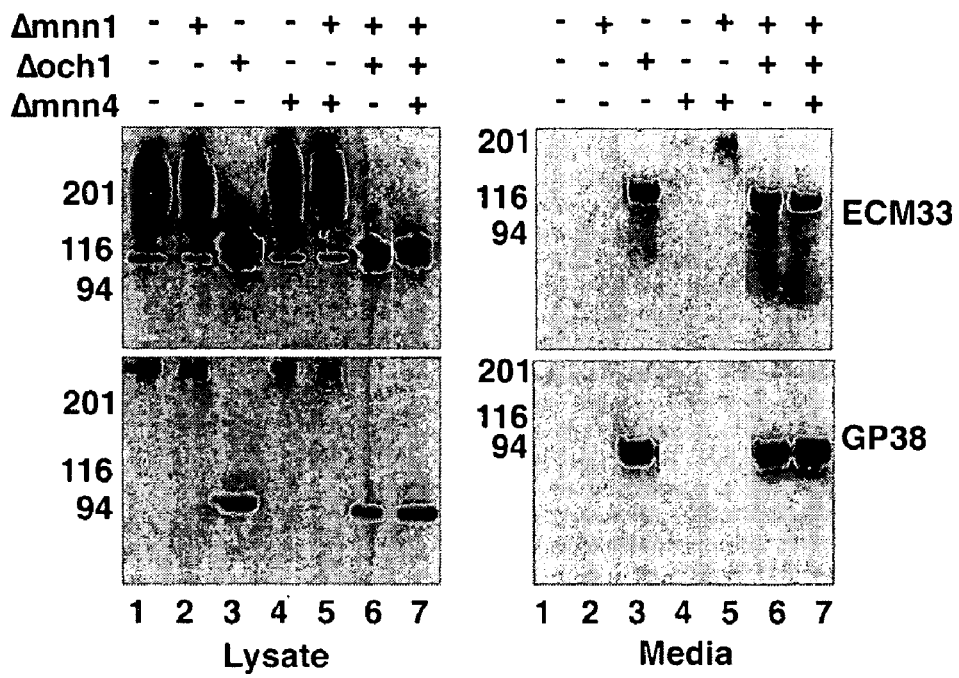
FIG. 31 shows migration shift of glycoproteins in the mutant of different genes. Yeast cells were grown to log phase and the cells and culture media were collected. Cells were lysed in RIPA buffer and loaded onto a 4-20% SDS-PAGE gradient gel at 2.4 μg/lane. The culture media was precipitated with acetone and proteins were also loaded onto a 4-20% SDS-PAGE gradient gel. Lane 1 is WT. Lane 2 is Δmnn1. Lane 3 is Δoch1. Lane 4 is Δmnn4. Lane 5 is Δmnn1mnn4. Lane 6 is Δmnn1Δoch1. Lane 7 is Δmnn1Δmnn4Δoch1. After blotting to nitrocellulose, the membranes are probed with anti-ECM33 (upper panels) or anti-GP38 (lower panels), followed by goat anti-rabbit IgG-HRP.

The discovery and identification of six yeast glycoproteins with the potential to mimic the 2G12 epitope warrants further investigation into the glycan structures on these proteins. Two of these proteins, ECM33 and GP38, were analyzed against a panel of yeast glycosylation mutants by Western blot. ECM33 is a glycosyl phosphatidyl inositol (GPI)-anchored protein important for cell wall stability (Pardo, Microbiology 150: 4157-70, 2004), and gp38 is a cell wall-related secretory protein (Destruelle, *Mol. Cell. Biol.* 14(4):2740-54, 1994). FIG. 31 (left panels) shows the results. In the cell lysate, both of these proteins are present in all the strains, albeit at different levels. In addition, these proteins are hypermannosylated in any strain without the $\Delta och1$ genotype. In fact, the $\Delta och1$ genotype causes a drastic shift in size of greater that 80 kDa for both protein, with GP38 showing a more significant change. A closer analysis of the these strains shows that in both proteins there is a noticeable size shift between the $\Delta och1$ and $\Delta och1\Delta mnn1$ strain, indicating a loss of terminal $\alpha1,3$-linked manse residues. The final protein sizes in the $\Delta mnn1\Delta mnn4\Delta och1$ mutant appear to be the same size as the proteins precipitated by 2G12; ~110 kDa for ECM33 and ~95 kDa for GP38 (see FIG. 31). Any size shift caused by the loss of phosphomannose in $\Delta mnn4$ mutants is not seen on the SDS-PAGE gels, suggesting that the change is too slight.

In the culture supernatant (FIG. 31, right panels), there is little to no GP38 or ECM33 present from any strains with the OCH1 gene. It appears that the weak cell walls of $\Delta och1$ containing yeast mutants results in the release of these proteins into the media. However, a similar size shift can be seen in ECM33 by comparing the ~200 kDa band found in the $\Delta mnn1\Delta mnn4$ mutant and the 110-115 kDa band found in $\Delta och1$ containing mutants. Again, this shows the lack of outer chain hypermannosylation. Also, a similar size shift from the $\Delta mnn1$ mutation can be seen between $\Delta och1$ and $\Delta och1\Delta mnn1$ mutants or triple mutants.

Taken together, these results help us visualize the loss of hypermannosylation and $\alpha b$ 1,3-linked mannose caps as the yeast strains are mutated. By comparing these results with FIG. 25, 2G12 reactivity is not present unless both of these changes in glycan structure are present. Thus, the ability of ECM33 and GP38 to bind 2G12, along with Gas1, Gas5, YJL171c, and PST1, is dependent upon the presence of core Man8 oligosaccharides preserved in the yeast triple mutant and $\Delta och1\Delta mnn1$ double mutants.

Production of $\alpha1,2$-Mannose Specific Anti-Sera in Rabbits that Cross-Reacts with gp120 by ELISA.

Figure 32:
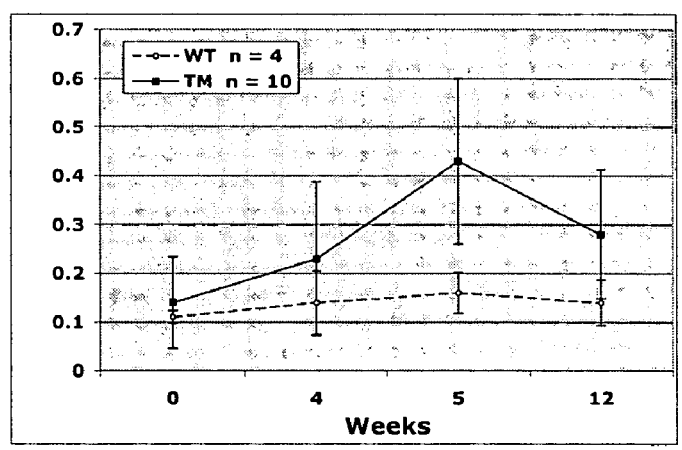
FIG. 32 shows the analysis of antibodies against α-1,2-linked mannoses raised in rabbits immunized with triple mutant yeast cells. Rabbits were immunized with whole cells from wild type (WT) and triple mutant (TM) of *S. cerevisiae*. Microwell plates were coated with 5 μg/ml of HIV-1 gp120 from JRFL strain produced in 293T cells. The immune sera were diluted to 1:500 and the antibodies against α1,2-Man were detected with 2G12.
Figure 39:
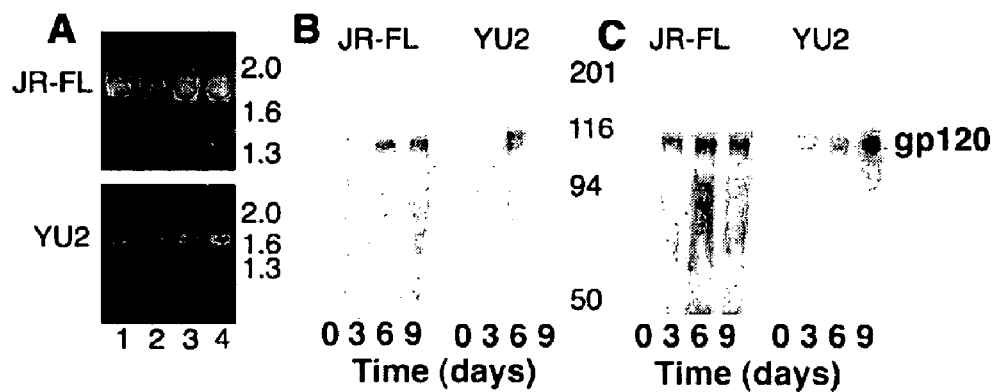
FIG. 39 shows cloning and expression of gp120 glycoproteins in triple mutant yeast. Panel A shows colony PCR results on yeast transformants run onto a 1.0% agarose gel. Four separate yeast clones of Δmnn1Δmnn4Δoch1, transformed with YU2-gp120 or JRFL-gp120, were picked from –ura/glucose plates and incubated with PCR master mix. The PCR mixture contained the primers MFα1-Kpn-5 and JRFL-Xba-3 for pJRFL-gp120 verification and MFα1-Kpn-5 and YU2-Xba-3 for the pYU2-gp120. The expected PCR product sizes were 1724 kB and 1697 kB for JRFL and YU2 transformants, respectively. Panel B shows the detection of gp120 using anti-gp120-IIIB (Virostat Inc.). One Δmnn1Δmnn4Δoch1 transformant of each plasmid (JRFL-gp120 and YU2-gp120) was induced for gp120 expression by growth in –ura/galactose media. A sample of the culture media was collected at four different time points: 0, 3, 6, and 9 days. Proteins were precipitated with acetone, run onto a 4-20% SDS-PAGE gel, and detected using anti-gp120-IIIB. Panel C shows the detection of gp120 using anti-gp120-YU2. The same Δmnn1Δmnn4Δoch1 transformants were induced for the indicated days. Proteins were precipitated with acetone, run onto a 4-20% SDS-PAGE gel, and detected using anti-gp120-YU2. The resulting proteins detected by both anti-gp120 show a clear band at 110 kDa, with optimal expression at 6 days to 9 days.
Figure 40:
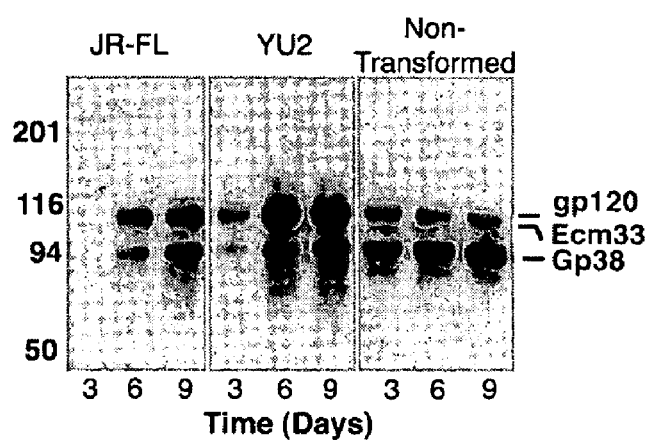
FIG. 40 shows detection of expressed gp120 with 2G12. One Δmnn1Δmnn4Δoch1 transformant of each plasmid (JRFL-gp120 and YU2-gp120) was induced for gp120 expression by growth in –ura/galactose media, and one clone of non-transformed Δmnn1Δmnn4Δoch1 was grown in SC/galactose. A sample of the culture media was collected at 3, 6, and 9 days, as indicated. Proteins were precipitated with acetone, run onto a 4-20% SDS-PAGE gel, and detected using 2G12. These gp120 glycoproteins have a predicted molecular weight of 96.4 and 99.6 kDa for JR-FL and YU-2 gp120, respectively.

We identified at least six yeast glycoproteins, PST1, ECM33, Gas1, Gas5, GP38 and YJL171c, from $\Delta mnn1\Delta mnn4\Delta och1$ cells that showed cross-reactivity to the HIV MAb 2G12. In addition, the cell wall of the yeast triple mutant was able to cross-react with 2G12 by whole cell ELISA and immunofluorescence. Therefore, in order to attempt to induce antibodies similar to 2G12-such that they are specific to $\alpha1,2$-linked terminal mannose sugars-whole cell, heat-killed triple mutant cells were used to immunize rabbits. Serum samples from 0, 4, 5, and 12 weeks were tested for HIV Env-specific total IgG antibodies. As shown in FIG. 32, the levels of antibodies specific to gp120 show a significant increase from week 0 to week 5, and a subsequent decrease at week 12. There was a significant increase in the gp120 binding in the sera from week 5 when compared to week 0 ($P<0.001$), while the binding at week 12 showed a significant increase too ($P<0.05$) although the titer is lower.

For comparison, rabbits were immunized in parallel with whole cell, heat-killed WT cells. The resulting sera showed that there is no significant increase in the levels of gp120 specific antibodies from week 0 to week 12 (see FIG. 32). By comparing the parallel bleeds from WT and triple mutant immunized rabbits, we again see a significant increase in gp120-specific IgG in the triple mutant, particularly at week 5 ($P<0.001$), when compared to WT. All of these p values were calculated by the Student's two-tailed t test. Altogether, these results may present the first instance of the production of antibodies in animals that are able to cross-react with the $\alpha1,2$-linked terminal mannose residues on gp120.

III. Bioinformatic Analyses of N-Linked and O-Linked Glycosylation Sites in the Glycoproteins Recognized by 2G12 in the Yeast Triple Mutant.

FIGS. 33-38 show the analyses of potential N-linked and O-linked glycosylation sites of PST1, ECM33, GP38, YJL171c, Gas1, and Gas5. Table 2 below shows a summary of identified 2G12-reactive glycoproteins in yeast mutants. There are several noticeable features of the identified 2G12 cross-reactive glycoproteins. All have a high number and density of N-linked and/or O-linked glycosylation sites. Among them, PST1 and ECM33 are members in the same family and have high number and density of both N-linked and O-linked glycosylation sites. GP38 and YJL171c have only high number and density of N-linked glycosylation sites, and Gas1 and Gas5 in the same family have high number and density of O-linked glycosylation sites and lower percentage (approximately 50% versus 60% of the other four) of molecular mass from glycans.

Example 4

Production and Characterization of HIV-1 gp120 Glycoproteins with Homogenous Man8 type Glycans in Och1/Mnn1/Mnn4 Triple Mutant Unlike in the mammalian expression system, the carbohydrates on glycoproteins produced in *S. cerevisiae* contain only mannose residues built upon the core GlcNAc$_2$ sugars. Full-length gp120 proteins have been successfully expressed in *S. cerevisiae*, although they appear to by hyperglycosylated. In order to create gp120 proteins in yeast with strictly Man$_8$GlcNAc$_2$, the glycosylation pathway had to be mutated. Three proteins are responsible for creating N-linked glycans that are specific to *S. cerevisiae*: OCH1p initiates the first α1,6 mannose residue necessary for hypermannosylation (Lehle, et al., *FEBS Lett.*, 370(1-2):41-5, 1995), MNN1p is responsible for all terminal α1,3-linked mannose capping of α1,2 residues (Nakajima et al., *Proc Nat Acad Sci USA*, 3912-3916, 1975), and MNN4p is a positive regulator of mannosylphosphorylation (Jigami, et al., *Biochim Biophys Acta*, 1426(2):335-45, 1999). By deleting these three genes in *S. cerevisiae*, a strain for the production of gp120 with strictly Man8 oligosaccharides was created.

In order for gp120 to be efficiently glycosylated in the ER and secreted into the culture media, we first cloned the signal sequence of the *S. cerevisiae* alpha-mating factor (MFα) into the pYES2/CT vector (Invitrogen), which contains the GAL1 promoter for high-level expression of recombinant proteins

TABLE 2

Summary of identified 2G12-reactive glycoproteins in yeast mutants.
Characterization of 2G12 Cross-Reactive Glycoproteins in Yeast Mutants

| ID | Name | Precursor aa No. | Mature Protein aa No. | Mature Protein MW | Mature Protein PI | N-sites No. (%) | O-sites No. (%) | Moleculsar weight (kDa) PAGE | Moleculsar weight (kDa) MW | Moleculsar weight (kDa) Glycan (%) | GPI |
|---|---|---|---|---|---|---|---|---|---|---|---|
| P38616 | GP38 | 354 | 315 | 33,124 | 4.67 | 15 (4.8) | 4 (1.3) | 90 | 33 | 57 (63) | No |
| P46992 | YJL171c | 396 | 349 | 37,723 | 4.69 | 11 (3.2) | 0 (0) | 90 | 38 | 52 (58) | Yes |
| Q12355 | PST1 | 444 | 399 | 41,260 | 9.25 | 15 (3.8) | 14 (3.5) | 100 | 41 | 59 (59) | Yes |
| P38248 | ECM33 | 469 | 386 | 39,628 | 4.68 | 13 (3.4) | 21 (5.4) | 100 | 40 | 60 (60) | Yes |
| P22146 | Gas1 | 559 | 506 | 54,325 | 4.37 | 10 (2.0) | 26 (5.1) | 105 | 54 | 51 (49) | Yes |
| Q08193 | Gas5 | 484 | 440 | 47,298 | 4.43 | 6 (1.4) | 35 (8) | 100 | 47 | 53 (53) | Yes |

Table 3 below shows the homologs of 2G12 cross-reactive glycoproteins among 18 genomes. The protein sequences of the six 2G12 cross-reactive glycoproteins were used to search homolog genes from HomoloGene database (release 50.1) of National Center for Biotechnology Information (NCBI). HomoloGene is a system for automated detection of homologs among the annotated genes of several completely sequenced eukaryotic genomes. Currently HomoloGene database contains 165,820 HomoloGene groups from 18 species. The HomoloGene of interest is obtained by entering protein Reference Sequence (RefSeq) number at NCBI home page. Multiple alignment of the HomoloGene was performed by clustalw program. The homologs of each gene were obtained from HomeloGene database searching and listed in the table. Homologs in *Candida glabrata* of the six genes were found in NCBI database but the genome of *Candida glabrata* is not included in the HomoloGene database.

TABLE 3

Homologs of 2G12 cross-reactive glycoproteins among 18 genomes.
Homologs of 2G12 Cross-Reactive Glycoproteins among 18 Genomes

| | Genome | Species | PST1 | ECM33 | Gas1 | Gas5 | GP38 | YJL171c |
|---|---|---|---|---|---|---|---|---|
| Mammalian | *Homo sapiens* | Human | − | − | − | − | − | − |
| | *Pan troglodytes* | Chimpanzee | − | − | − | − | − | − |
| | *Canis familiaris* | Dog | − | − | − | − | − | − |
| | *Mus musculus* | House mouse | − | − | − | − | − | − |
| | *Rattus norvegicus* | Rat | − | − | − | − | − | − |
| Bird | *Gallus gallus* | Chicken | − | − | − | − | − | − |
| Insect | *Drosophila melanogaster* | Fly | − | − | − | − | − | − |
| | *Anopheles gambiae* | Mosquito | − | − | − | − | − | − |
| Worm | *Caenorhabditis elegans* | Small soil nematode | − | − | − | − | − | − |
| Fungus | *Saccharomyces cerevisiae* | Yeast | + | + | + | + | + | + |
| | *Schizosaccharomyces pombe* | Yeast | + | + | + | + | − | − |
| | *Kluyveromyces lactis* | Yeast | − | + | + | + | − | + |
| | *Eremothecium gossypii* | Cotton pathogen | + | − | − | + | − | − |
| | *Magnaporthe grisea* | Rice blast fungus | − | + | + | − | − | − |
| | *Neurospora crassa* | Red bread mold | − | + | + | + | − | − |
| Plant | *Arabidopsis thaliana* | Small flowering plant | − | − | − | − | − | − |
| | *Oryza sativa* | Japanese rice | − | − | − | − | − | − |
| Parasite | *Plasmodium falciparum* | malaria parasite | − | − | − | − | − | − | following galactose induction. Then, HIV-1 gp120 genes from strains of JR-FL and YU2 (ARRRP) were PCR cloned into the pYES2/CT-α plasmid. The resulting gp120 expression plasmids were transformed into the haploid yeast strain Δmnn1Δmnn4Δoch1, using a quick lithium acetate transformation protocol. As seen in Panel A of FIG. 40, four separate clones of Δmnn1Δmnn4Δoch1-2-5, transformed with pYU2-gp120 or pJRFL-gp120, were verified to contain their respective plasmids by colony PCR. JRFL-gp120 transformants show an expected PCR product size of 724 kB while YU2-gp120 transformants show a product at 1697kB.

These yeast transformants containing the pYU2-gp120 and pJRFL-gp120 were induced for protein expression by transferring the cells to galactose containing media. Western blotting using anti-gp120-IIIB (Virostat Inc.) and anti-gp120-YU2 were used to detect the induction and secretion of gp120 glycoproteins in the media. The Δmnn1Δmnn4Δoch1 yeast transformants were found to secrete the greatest amount of gp120 by growth at 30° C. for 6 to 9 days (FIG. 39, Panel B and C). As seen in the Western blot, these gp120 proteins migrate to their predicted molecular mass of 96.4 and 99.6 kDa for JR-FL and YU-2 gp120, respectively, assuming they contain mainly Man8 oligosaccharides.

In addition to being reactive to anti-gp120 antibodies, these expressed gp120 proteins also show reactivity to 2G12 (FIG. 40). Two Δmnn1Δmnn4Δoch1 transformants (with pYU2-gp120-pJR-FL-gp120) and a non-transformed strain were grown in parallel, with uracil added to the media of the non-transformant. Due to the presence of other 2G12-reactive proteins in the culture supernatant of Δmnn1Δmnn4Δoch1 cells, one of which has a molecular weight of ~110 kDa, the induction of gp120 can only be seen indirectly when testing with 2G12. The non-d transformed yeast shows a steady basal expression level from 3-9 days, strongly suggesting that the basal level protein at ~110 kDa (ECM33) does not increase in this time period. By contrast, both of the gp120 transformed yeast show a marked increase in the expression of the 110 kDa protein from 3-9 days, suggesting the induction of gp120 glycoproteins that are recognized by the 2G12 antibody.

LITERATURE CITED

1. UN AIDS Report on Global AIDS Epidemic. 2004.
2. McMichael A J, Hanke T. HIV vaccines 1983-2003. Nat. Med. 2003; 9(7):874-80.
3. Garber D A, Silvestri G, Feinberg M B. Prospects for an AIDS vaccine: three big questions, no easy answers. Lancet Infect Dis. 2004; 4(7):397-413.
4. see worldwide web at niaid.nih.gov/daids/vaccine
5. see worldwide web at iavi.org
6. Gaschen B, Taylor J, Yusim K, Foley B, Gao F, Lang D, Novitsky V, Haynes B, Hahn B H, Bhattacharya T, Korber B. Diversity considerations in HIV-1 vaccine selection. Science. 2002; 296(5577):2354-60.
7. Burton D R, Desrosiers R C, Doms R W, Koff W C, Kwong P D, Moore J P, Nabel G J, Sodroski J, Wilson I A, Wyatt R T. HIV vaccine design and the neutralizing antibody problem. Nat. Immunol. 2004; 5(3):233-6.
8. Zolla-Pazner S. Identifying epitopes of HIV-1 that induce protective antibodies. Nat Rev Immunol. 2004; 4(3): 199-210.
9. Geijtenbeek T B, Kwon D S, Torensma R, van Vliet S J, van Duijnhoven G C, Middel J, Cornelissen I L, Nottet H S, KewalRamani V N, Littman D R, Figdor C G, van Kooyk Y. DC-SIGN, a dendritic cell-specific HIV-1-binding protein that enhances trans-infection of T cells. *Cell.* 2000; 100:587-97.
10. Pohlmann S, Baribaud F, Lee B, Leslie G J, Sanchez M D, Hiebenthal-Millow K, Munch J, Kirchhoff F, Doms R W. DC-SIGN interactions with human immunodeficiency virus type 1 and 2 and simian immunodeficiency virus. *J. Virol.* 2001; 75(10):4664-72.
11. Pohlmann S, Soilleux E J, Baribaud F, Leslie G J, Morris L S, Trowsdale J, Lee B, Coleman N, Doms R W. DC-SIGNR, a DC-SIGN homologue expressed in endothelial cells, binds to human and simian immunodeficiency viruses and activates infection in trans. *Proc Natl Acad Sci USA.* 2001; 98(5):2670-2675.
12. Curtis B M, Scharnowske S, Watson A J. Sequence and expression of a membrane-associated C-type lectin that exhibits CD4-independent binding of human immunodeficiency virus envelope glycoprotein gp120. *Proc Natl Acad Sci USA.* 1992; 89:8356-60.
13. Bashirova A A, Geijtenbeek T B, van Duijnhoven G C, van Vliet S J, Eilering J B, Martin M P, Wu L, Martin T D, Viebig N. Knolle P A, KewalRamani V N, van Kooyk Y, Carrington M. A dendritic cell-specific intercellular adhesion molecule 3-grabbing nonintegrin (DC-SIGN)-related protein is highly expressed on human liver sinusoidal endothelial cells and promotes HIV-1 infection. *J Exp Med.* 2001; 193(6):671-8.
14. Mitchell D A, Fadden A J, Drickamer K. A novel mechanism of carbohydrate recognition by the C-type lectins DC-SIGN and DC-SIGNR. Subunit organization and binding to multivalent ligands. *J Biol. Chem.* 2001; 276(31): 28939-45.
15. Feinberg H, Mitchell D A, Drickamer K, Weis W I. Structural basis for selective recognition of oligosaccharides by DC-SIGN and DC-SIGNR. *Science.* 2001; 294(5549):2163-6.
16. Pohlmann S, Doms R W. Evaluation of current approaches to inhibit HIV entry. Curr Drug Targets Infect Disord. 2002; 2(1):9-16.
17. Trkola A, Purtscher M, Muster T, Ballaun C, Buchacher A, Sullivan N, Srinivasan K, Sodroski J, Moore J P, Katinger H. Human monoclonal antibody 2G12 defines a distinctive neutralization epitope on the gp120 glycoprotein of human immunodeficiency virus type 1. *J. Virol.* 1996; 70(2): 1100-8.
18. Scanlan C N, Pantophlet R, Wormald M R, Ollmann Saphire E, Stanfield R, Wilson I A, Katinger H, Dwek R A, Rudd P M, Burton D R. The broadly neutralizing anti-human immunodeficiency virus type 1 antibody 2G12 recognizes a cluster of alpha1 —>2 mannose residues on the outer face of gp120. *J Virol.* 2002; 76(14):7306-21.
19. Sanders R W, Venturi M, Schiffner L, Kalyanaraman R, Katinger H, Lloyd K O, Kwong P D, Moore J P. The mannose-dependent epitope for neutralizing antibody 2G12 on human immunodeficiency virus type 1 glycoprotein gp120. *J Virol.* 2002; 76(14):7293-305.
20. Shattock R J, Moore J P. Inhibiting sexual transmission of HIV-1 infection. Nat Rev Microbiol. 2003; 1(1):25-34.
21. Boyd M R, Gustafson K R, McMahon J B, Shoemaker R H, O'Keefe B R, Mori T, Gulakowski R J, Wu L, Rivera M I, Laurencot C M, Currens M J, Cardellina J H 2nd, Buckheit R W Jr, Nara P L, Pannell L K, Sowder R C 2nd, Henderson L E. Discovery of cyanovirin-N, a novel human immunodeficiency virus-inactivating protein that binds viral surface envelope glycoprotein gp120: potential applications to microbicide development. Antimicrob Agents Chemother. July; 41(7):1521-30.
22. Esser M T, Mori T, Mondor I, Sattentau Q J, Dey B, Berger E A, Boyd M R, Lifson J D. Cyanovirin-N binds to gp120 to interfere with CD4-dependent human immunodeficiency virus type 1 virion binding, fusion, and infectivity but does not affect the CD4 binding site on gp120 or soluble CD4-induced conformational changes in gp120. J Virol. 1999; 73(5):4360-71.
23. Dey B, Lerner D L, Lusso P, Boyd M R, Elder J H, Berger E A. Multiple antiviral activities of cyanovirin-N: blocking of human immunodeficiency virus type 1 gp120 interaction with CD4 and coreceptor and inhibition of diverse enveloped viruses. J Virol. 2000; 74(10):4562-9.
24. Tsai C C, Emau P, Jiang Y, Agy M B, Shattock R J, Schmidt A, Morton W R, Gustafson K R, Boyd M R. Cyanovirin-N inhibits AIDS virus infections in vaginal transmission models. AIDS Res Hum Retroviruses. 2004; 20(1): 11-8.
25. Tsai C C, Emau P, Jiang Y, Tian B, Morton W R, Gustafson K R, Boyd M R. Cyanovirin-N gel as a topical microbicide prevents rectal transmission of SHIV89.6P in macaques. AIDS Res Hum Retroviruses. 2003; 19(7):535-41.
26. Bewley C A, Otero-Quintero S. The potent anti-HIV protein cyanovirin-N contains two novel carbohydrate binding sites that selectively bind to Man(8) DID3 and Man(9) with nanomolar affinity: implications for binding to the HIV envelope protein gp120. J Am Chem. Soc. 2001; 123(17):3892-902.
27. Sandstrom C, Berteau O, Gemma E, Oscarson S, Kenne L, Gronenborn A M. Atomic Mapping of the Interactions between the Antiviral Agent Cyanovirin-N and Oligomannosides by Saturation-Transfer Difference N M R. Biochemistry. 2004; 43(44): 13926-13931.
28. Li H, Wang L X. Design and synthesis of a template-assembled oligomannose cluster as an epitope mimic for human HIV-neutralizing antibody 2G12. Org Biomol Chem. 2004; 2(4):483-8.
29. Wang L X, Ni J, Singh S, Li H. Binding of high-mannose-type oligosaccharides and synthetic oligomannose clusters to human antibody 2G12: implications for HIV-1 vaccine design. Chem. Biol. 2004; 1(1):127-34.
30. Lee H K, Scanlan C N, Huang C Y, Chang A Y, Calarese D A, Dwek R A, Rudd P M, Burton D R, Wilson I A, Wong C H. Reactivity-based one-pot synthesis of oligomannoses: defining antigens recognized by 2G12, a broadly neutralizing anti-HIV-1 antibody. Angew Chem Int Ed Engl. 2004; 43(8):1000-3.
31. Calarese D A, Scanlan C N, Zwick M B, Deechongkit S, Mimura Y, Kunert R, Zhu P, Wormald M R, Stanfield R L, Roux K H, Kelly J W, Rudd P M, Dwek R A, Katinger H, Burton D R, Wilson I A. Antibody domain exchange is an immunological solution to carbohydrate cluster recognition. Science. 2003; 300(5628):2065-71.
32. Roux K H, Zhu P, Seavy M, Katinger H, Kunert R, Seamon V. Electron microscopic and immunochemical analysis of the broadly neutralizing HIV-1-specific, anti-carbohydrate antibody, 2G12. Mol Immunol. 2004; 41(10):1001-11.
33. Veazey R S, Shattock R J, Pope M, Kirijan J C, Jones J, Hu Q, Ketas T, Marx P A, Klasse P J, Burton D R, Moore J P. Prevention of virus transmission to macaque monkeys by a vaginally applied monoclonal antibody to HIV-1 gp120. Nat Med. 200; 9(3):343-6.
34. Dacheux L, Moreau A, Ataman-Onal Y, Biron F, Verrier B, Barin F. Evolutionary Dynamics of the Glycan Shield of the Human Immunodeficiency Virus Envelope during Natural Infection and Implications for Exposure of the 2G12 Epitope. J Virol. 2004; 78(22): 12625-37.
35. Binley J M, Wrin T, Korber B, Zwick M B, Wang M, Chappey C, Stiegler G, Kunert R, Zolla-Pazner S, Katinger H, Petropoulos C J, Burton D R. Comprehensive cross-clade neutralization analysis of a panel of anti-human immunodeficiency virus type 1 monoclonal antibodies. J Virol. 2004; 78(23):13232-52.
36. Hindsgaul 0.1999. Protein-glycan interactions. In Essentials of Glycobiology (ed Varki A, et al), pp. 41-56, Cold Spring Harbor Laboratory Press, New York.
37. Winzeler E A, Shoemaker D D, Astromoff A, et al. Functional characterization of the S. cerevisiae genome by gene deletion and parallel analysis. Science. 1999; 285(5429): 901-6.
38. Muller W E, Schroder H C, Reuter P, Maidhof A, Uhlenbruck G, Winkler I. Polyclonal antibodies to mannan from yeast also recognize the carbohydrate structure of gp120 of the AIDS virus: an approach to raise neutralizing antibodies to HIV-1 infection in vitro. AIDS. 1990; 4(2):159-62.
39. Ozinsky A, Underhill D M, Fontenot J D, Hajjar A M, Smith K D, Wilson C B, Schroeder L, Aderem A. The repertoire for pattern recognition of pathogens by the innate immune system is defined by cooperation between toll-like receptors. Proc Natl Acad Sci USA. 2000; 97(25): 13766-71.
40. Sato M, Sano H, Iwaki D, Kudo K, Konishi M, Takahashi H, Takahashi T, Imaizumi H, Asai Y, Kuroki Y. Direct binding of Toll-like receptor 2 to zymosan, and zymosan-induced NF-kappa B activation and TNF-alpha secretion are down-regulated by lung collectin surfactant protein A. J Immunol. 2003; 171(1):417-25.
41. Mond J J, Lees A, Snapper C M. T cell-independent antigens type 2. *Annu Rev Immunol.* 1995; 13:655-92.
42. Berland R, Wortis H H. Origins and functions of B-1 cells with notes on the role of CD5. *Annu Rev Immunol.* 2002; 20:253-300.
43. Lesinski G B, Westerink M A. Novel vaccine strategies to T-independent antigens. *J Microbiol Methods.* 2001; 47(2): 135-49.
44. Lockhart S. Conjugate vaccines. Expert Rev Vaccines. 2003; 2(5):633-48.
45. Ada G, Isaacs D. Carbohydrate-protein conjugate vaccines. Clin Microbiol Infect. 2003; 9(2):79-85.
46. Weis W I, Taylor M E, Drickainer K. The C-type lectin superfamily in the immune system. Immunol Rev. 1998; 163:19-34.
47. Cutalo J M, Deterding L J, Tomer K B. Characterization of glycopeptides from HIV-1(SF2) gp120 by liquid chromatography mass spectrometry. J Am Soc Mass Spectrom. 200; 15(11):1545-55.
48. Ji X, Gewurz H, Spear G T. Mannose binding lectin (MBL) and HIV. Mol Immunol. 2005; 42(2): 145-52.
49. Botos I, Wlodawer A. Proteins that bind high-mannose sugars of the HIV envelope. Prog Biophys Mol Biol. 2005; 88(2):233-82.
50. Funatsu O, Sato T, Kotovuori P, Gahmberg C G, Ikekita M, Furukawa K. Structural study of N-linked oligosaccharides of human intercellular adhesion molecule-3 (CD50). *Eur J Biochem.* 2001; 268(4):1020-9.
51. Herscovics A. Importance of glycosidases in mammalian glycoprotein biosynthesis. Biochim Biophys Acta. 1999 Dec. 6; 1473(1):96-107.
52. Hitzeman, R. A., Chen, C. Y., Dowbenko, D. J., Renz, M. E., Lui, C., Pai, R., Simpson, N. J., Kohr, W. J., Singh, A., Chisolm, V., Hamilton, R. and Chang, C. N. Use of heterologous and homologous signal sequences for secretion of heterologous proteins from yeast. *Methods Enzymol.* 1990; 185:421-440.
53. Barr, P. J., Steimer, K. S., Sabin, E. A., Parkes, D., George-Nascimento, C., Stephans, J. C., Powers, M. A., Gyenes, A., Van Nest, G. A., Miller, E. T., Higgins, K. W. and Luciw, P. A. Antigenicity and immunogenicity of domains of the human immunodeficiency virus (HIV) envelope polypeptide expressed in the yeast *Saccharomyces cerevisiae*. *Vaccine* 1987; 5:90-101.
54. Liu, W. F., Gao, D. and Wang, Z. N. Expression of the extracellular domain of the human immunodeficiency virus type 1 envelope protein and its fusion with β-galactosidase in *Saccharoniyces cerevisiae*. *Clin Diagn lab Immunol*. 1998; 5:592-594.
55. Herscovics A. Processing glycosidases of *Saccharomyces cerevisiae*. Biochim Biophys Acta. 1999; 1426(2):275-85.
56. Camirand A, Heysen A, Grondin B, Herscovics A. Glycoprotein biosynthesis in *Saccharomyces cerevisiae*. Isolation and characterization of the gene encoding a specific processing alpha-mannosidase. J Biol Chem. 1991; 266 (23):15120-7.
57. Smith, R. A., Duncan, M. J. and Moir, D. T. Heterologous protein secretion from yeast. *Science* 1985; 229:1219-1224.
58. Rudolph, H. K., Antebi, A., Fink, G. R., Buckley, C. M., Dorman, T. E., LeVitre, J., Davidow, S., Mao, J., Moir, D. T. The yeast secretory pathway is perturbed by mutations in PMR1, a member of a $Ca^{2+}$ ATPase family. *Cell*. 1989; 58:133-145.
59. Livi, G. P., Ferrara, A., Roskin, R., Simon, P. L. and Young P. R. Secretion of N-glycosylated human recombinant interleukin-1α in *Saccharomyces cerevisiae*. *Gene* 1990; 88:297-301.
60. Harmsen, M. M., Langedijk, A. C., van Tuinen, E., Geerse, R. H., Raué, H. A. and Maat, J. Effect of a pmr1 disruption and different signal sequences on the intracellular processing and secretion of *Cyamopsis tetragonoloba* α-galactosidase by *Saccharomyces cerevisiae*. *Gene* 1993; 125:115-123.

---

The invention claimed is:

1. A composition for eliciting antibodies specific for a protein comprising an epitope recognized by antibody 2G12 in a subject, said composition comprising a glycosylated polypeptide comprising at least two N-linked high mannose oligosaccharides that are recognized by antibody 2G12, and a pharmaceutically acceptable excipient, wherein greater than 50% of the N-linked glycans on the polypeptide are the high-mannose oligosaccharides, and wherein the high-mannose oligosaccharides are $Man_9GlcNAc_2$, $Man_8GlcNAc_2$, or a combination thereof, and wherein the polypeptide is expressed by a mutant fungus having disrupted och1, mnn1 and mnn4 genes of *Saccharomyces cerevisiae* or disrupted homolog genes of och1, mnn1 and mnn4 genes of *Saccharomyces cerevisiae*, and the polypeptide is isolated from the mutant fungus.

2. The composition of claim 1, wherein the polypeptide comprises at least three N-linked high-mannose oligosaccharides.

3. The composition of claim 1, wherein the polypeptide comprises the amino acid sequence of gp120 or a fragment thereof, wherein the fragment comprises at least two N-linked high mannose oligosaccharides that are recognized by antibody 2G12, and wherein greater than 50% of the N-linked glycans on the fragment are $Man_9GlcNAc_2$, $Man_8GlcNAc_2$, or a combination thereof.

4. The composition of claim 1, wherein the polypeptide comprises the amino acid sequence of a fungus glycoprotein or a fragment thereof, wherein the fragment comprises at least two N-linked high mannose oligosaccharides that are recognized by antibody 2G12, and wherein greater than 50% of the N-linked glycans on the fragment are $Man_9GlcNAc_2$, $Man_8GlcNAc_2$, or a combination thereof.

5. The composition of claim 1, wherein the polypeptide comprises the amino acid sequence of a yeast glycoprotein or a fragment thereof, wherein the fragment comprises at least two N-linked high mannose oligosaccharides that are recognized by antibody 2G12, and wherein greater than 50% of the N-linked glycans on the fragment are $Man_9GlcNAc_2$, $Man_8GlcNAc_2$, or a combination thereof.

6. The composition of claim 5, wherein the yeast is *Saccharomyces cerevisiae.*

7. The composition of claim 5, wherein the yeast glycoprotein is selected from the group consisting of PST1, ECM33, Gas1, Gas5, GP38, and YJL171c.

8. The composition of claim 5, wherein the yeast is *Pichia pastoris.*

9. The composition of claim 5, wherein the yeast is *Candida albicans.*

10. The composition of claim 4, wherein the polypeptide comprises the amino acid sequence of a fungus glycoprotein which is a homolog to PST1, ECM33, Gas1, Gas5, GP38, or YJL171c of *Saccharomyces cerevisiae.*

11. The composition of claim 1, wherein at least 90% of the N-linked glycans on the polypeptide are $Man_9GlcNAc_2$, $Man_8GlcNAc_2$, or a combination thereof.

12. The composition of claim 1, wherein at least 90% of the N-linked glycans on the polypeptide are $Man_8GlcNAc_2$.

13. The composition of claim 1, wherein the pharmaceutically acceptable excipient comprises an adjuvant.

14. A composition for eliciting antibodies specific for a protein having an epitope recognized by antibody 2G12 in a subject, said composition comprising a glycosylated polypeptide isolated from a mutant fungus having disrupted och1, mnn1, and mnn4 genes of *Saccharomyces cerevisiae* or disrupted homolog genes of och1, mnn1, and mnn4 genes of *Saccharomyces cerevisiae*, wherein the glycosylated polypeptide is recognized by antibody 2G12, and a pharmaceutically acceptable excipient.

15. A composition comprising a whole cell of a mutant yeast, and an adjuvant, wherein the mutant yeast has disrupted och1, mnn1, and mnn4 genes of *Saccharomyces cerevisiae*, or disrupted homolog genes of och1, mnn1, and mnn4 genes of *Saccharomyces cerevisiae.*

16. The composition of claim 1, wherein the glycosylated polypeptide is conjugated to stimulatory epitopes of tetanus toxin.

17. The composition of claim 1, wherein the glycosylated polypeptide comprises at least six N-linked high-mannose oligosaccharides.

18. The composition of claim 1, wherein the glycosylated polypeptide comprises at least seven N-linked high-mannose oligosaccharides.

* * * * *

SEQUENCE LISTING

```
<160> NUMBER OF SEQ ID NOS: 25

<210> SEQ ID NO 1
<211> LENGTH: 444
<212> TYPE: PRT
<213> ORGANISM: Yeast

<400> SEQUENCE: 1

Met Gln Leu His Ser Leu Ile Ala Ser Thr Ala Leu Leu Ile Thr Ser
1               5                   10                  15

Ala Leu Ala Ala Thr Ser Ser Ser Ser Ile Pro Ser Ser Cys Thr
            20                  25                  30

Ile Ser Ser His Ala Thr Ala Thr Ala Gln Ser Asp Leu Asp Lys Tyr
        35                  40                  45

Ser Arg Cys Asp Thr Leu Val Gly Asn Leu Thr Ile Gly Gly Gly Leu
    50                  55                  60

Lys Thr Gly Ala Leu Ala Asn Val Lys Glu Ile Asn Gly Ser Leu Thr
65                  70                  75                  80

Ile Phe Asn Ala Thr Asn Leu Thr Ser Phe Ala Ala Asp Ser Leu Glu
                85                  90                  95

Ser Ile Thr Asp Ser Leu Asn Leu Gln Ser Leu Thr Ile Leu Thr Ser
            100                 105                 110

Ala Ser Phe Gly Ser Leu Gln Ser Val Asp Ser Ile Lys Leu Ile Thr
        115                 120                 125

Leu Pro Ala Ile Ser Ser Phe Thr Ser Asn Ile Lys Ser Ala Asn Asn
    130                 135                 140

Ile Tyr Ile Ser Asp Thr Ser Leu Gln Ser Val Asp Gly Phe Ser Ala
145                 150                 155                 160

Leu Lys Lys Val Asn Val Phe Asn Val Asn Asn Lys Lys Leu Thr
                165                 170                 175

Ser Ile Lys Ser Pro Val Glu Thr Val Ser Asp Ser Leu Gln Phe Ser
            180                 185                 190

Phe Asn Gly Asn Gln Thr Lys Ile Thr Phe Asp Asp Leu Val Trp Ala
        195                 200                 205

Asn Asn Ile Ser Leu Thr Asp Val His Ser Val Ser Phe Ala Asn Leu
    210                 215                 220

Gln Lys Ile Asn Ser Ser Leu Gly Phe Ile Asn Asn Ser Ile Ser Ser
225                 230                 235                 240
```

-continued

```
Leu Asn Phe Thr Lys Leu Asn Thr Ile Gly Gln Thr Phe Ser Ile Val
                245                 250                 255

Ser Asn Asp Tyr Leu Lys Asn Leu Ser Phe Ser Asn Leu Ser Thr Ile
            260                 265                 270

Gly Gly Ala Leu Val Val Ala Asn Asn Thr Gly Leu Gln Lys Ile Gly
        275                 280                 285

Gly Leu Asp Asn Leu Thr Thr Ile Gly Gly Thr Leu Glu Val Val Gly
    290                 295                 300

Asn Phe Thr Ser Leu Asn Leu Asp Ser Leu Lys Ser Val Lys Gly Gly
305                 310                 315                 320

Ala Asp Val Glu Ser Lys Ser Ser Asn Phe Ser Cys Asn Ala Leu Lys
                325                 330                 335

Ala Leu Gln Lys Lys Gly Gly Ile Lys Gly Glu Ser Phe Val Cys Lys
            340                 345                 350

Asn Gly Ala Ser Ser Thr Ser Val Lys Leu Ser Ser Thr Ser Lys Ser
        355                 360                 365

Gln Ser Ser Gln Thr Thr Ala Lys Val Ser Lys Ser Ser Lys Ala
    370                 375                 380

Glu Glu Lys Lys Phe Thr Ser Gly Asp Ile Lys Ala Ala Ala Ser Ala
385                 390                 395                 400

Ser Ser Val Ser Ser Gly Ala Ser Ser Ser Ser Lys Ser
                405                 410                 415

Lys Gly Asn Ala Ala Ile Met Ala Pro Ile Gly Gln Thr Thr Pro Leu
            420                 425                 430

Val Gly Leu Leu Thr Ala Ile Ile Met Ser Ile Met
        435                 440
```

<210> SEQ ID NO 2
<211> LENGTH: 444
<212> TYPE: PRT
<213> ORGANISM: Yeast

<400> SEQUENCE: 2

```
Met Gln Leu His Ser Leu Ile Ala Ser Thr Ala Leu Leu Ile Thr Ser
 1                5                  10                  15

Ala Leu Ala Ala Thr Ser Ser Ser Ser Ile Pro Ser Ser Cys Thr
            20                  25                  30

Ile Ser Ser His Ala Thr Ala Thr Ala Gln Ser Asp Leu Asp Lys Tyr
        35                  40                  45

Ser Arg Cys Asp Thr Leu Val Gly Asn Leu Thr Ile Gly Gly Leu
    50                  55                  60

Lys Thr Gly Ala Leu Ala Asn Val Lys Glu Ile Asn Gly Ser Leu Thr
65                  70                  75                  80

Ile Phe Asn Ala Thr Asn Leu Thr Ser Phe Ala Ala Asp Ser Leu Glu
                85                  90                  95

Ser Ile Thr Asp Ser Leu Asn Leu Gln Ser Leu Thr Ile Leu Thr Ser
            100                 105                 110

Ala Ser Phe Gly Ser Leu Gln Ser Val Asp Ser Ile Lys Leu Ile Thr
        115                 120                 125

Leu Pro Ala Ile Ser Ser Phe Thr Ser Asn Ile Lys Ser Ala Asn Asn
    130                 135                 140

Ile Tyr Ile Ser Asp Thr Ser Leu Gln Ser Val Asp Gly Phe Ser Ala
145                 150                 155                 160

Leu Lys Lys Val Asn Val Phe Asn Val Asn Asn Lys Lys Leu Thr
                165                 170                 175
```

```
Ser Ile Lys Ser Pro Val Glu Thr Val Ser Asp Ser Leu Gln Phe Ser
            180                 185                 190

Phe Asn Gly Asn Gln Thr Lys Ile Thr Phe Asp Asp Leu Val Trp Ala
            195                 200                 205

Asn Asn Ile Ser Leu Thr Asp Val His Ser Val Ser Phe Ala Asn Leu
            210                 215                 220

Gln Lys Ile Asn Ser Ser Leu Gly Phe Ile Asn Asn Ser Ile Ser Ser
225                 230                 235                 240

Leu Asn Phe Thr Lys Leu Asn Thr Ile Gly Gln Thr Phe Ser Ile Val
                245                 250                 255

Ser Asn Asp Tyr Leu Lys Asn Leu Ser Phe Ser Asn Leu Ser Thr Ile
                260                 265                 270

Gly Gly Ala Leu Val Val Ala Asn Asn Thr Gly Leu Gln Lys Ile Gly
            275                 280                 285

Gly Leu Asp Asn Leu Thr Thr Ile Gly Gly Thr Leu Glu Val Val Gly
            290                 295                 300

Asn Phe Thr Ser Leu Asn Leu Asp Ser Leu Lys Ser Val Lys Gly Gly
305                 310                 315                 320

Ala Asp Val Glu Ser Lys Ser Asn Phe Ser Cys Asn Ala Leu Lys
                325                 330                 335

Ala Leu Gln Lys Lys Gly Gly Ile Lys Gly Glu Ser Phe Val Cys Lys
            340                 345                 350

Asn Gly Ala Ser Ser Thr Ser Val Lys Leu Ser Ser Thr Ser Lys Ser
            355                 360                 365

Gln Ser Ser Gln Thr Thr Ala Lys Val Ser Lys Ser Ser Lys Ala
370                 375                 380

Glu Glu Lys Lys Phe Thr Ser Gly Asp Ile Lys Ala Ala Ala Ser Ala
385                 390                 395                 400

Ser Ser Val Ser Ser Gly Ala Ser Ser Ser Ser Lys Ser Ser
            405                 410                 415

Lys Gly Asn Ala Ala Ile Met Ala Pro Ile Gly Gln Thr Thr Pro Leu
            420                 425                 430

Val Gly Leu Leu Thr Ala Ile Ile Met Ser Ile Met
            435                 440
```

<210> SEQ ID NO 3
<211> LENGTH: 469
<212> TYPE: PRT
<213> ORGANISM: Yeast

<400> SEQUENCE: 3

```
Met Gln Phe Lys Asn Ala Leu Thr Ala Thr Ala Ile Leu Ser Ala Ser
1               5                   10                  15

Ala Leu Ala Ala Ala Asn Ser Thr Thr Ser Ile Pro Ser Ser Cys Ser
            20                  25                  30

Ile Gly Thr Ser Ala Thr Ala Thr Ala Gln Ala Asp Leu Asp Lys Ile
            35                  40                  45

Ser Gly Cys Ser Thr Ile Val Gly Asn Leu Thr Ile Thr Gly Asp Leu
        50                  55                  60

Gly Ser Ala Ala Leu Ala Ser Ile Gln Glu Ile Asp Gly Ser Leu Thr
65                  70                  75                  80

Ile Phe Asn Ser Ser Leu Ser Ser Phe Ser Ala Asp Ser Ile Lys
                85                  90                  95

Lys Ile Thr Gly Asp Leu Asn Met Gln Glu Leu Ile Ile Leu Thr Ser
            100                 105                 110
```

```
Ala Ser Phe Gly Ser Leu Gln Glu Val Asp Ser Ile Asn Met Val Thr
            115                 120                 125

Leu Pro Ala Ile Ser Thr Phe Ser Thr Asp Leu Gln Asn Ala Asn Asn
130                 135                 140

Ile Ile Val Ser Asp Thr Thr Leu Glu Ser Val Glu Gly Phe Ser Thr
145                 150                 155                 160

Leu Lys Lys Val Asn Val Phe Asn Ile Asn Asn Arg Tyr Leu Asn
                165                 170                 175

Ser Phe Gln Ser Ser Leu Glu Ser Val Ser Asp Ser Leu Gln Phe Ser
            180                 185                 190

Ser Asn Gly Asp Asn Thr Thr Leu Ala Phe Asp Asn Leu Val Trp Ala
            195                 200                 205

Asn Asn Ile Thr Leu Arg Asp Val Asn Ser Ile Ser Phe Gly Ser Leu
            210                 215                 220

Gln Thr Val Asn Ala Ser Leu Gly Phe Ile Asn Asn Thr Leu Pro Ser
225                 230                 235                 240

Leu Asn Leu Thr Gln Leu Ser Lys Val Gly Gln Ser Leu Ser Ile Val
                245                 250                 255

Ser Asn Asp Glu Leu Ser Lys Ala Ala Phe Ser Asn Leu Thr Thr Val
            260                 265                 270

Gly Gly Gly Phe Ile Ile Ala Asn Asn Thr Gln Leu Lys Val Ile Asp
            275                 280                 285

Gly Phe Asn Lys Val Gln Thr Val Gly Gly Ala Ile Glu Val Thr Gly
            290                 295                 300

Asn Phe Ser Thr Leu Asp Leu Ser Ser Leu Lys Ser Val Arg Gly Gly
305                 310                 315                 320

Ala Asn Phe Asp Ser Ser Ser Asn Phe Ser Cys Asn Ala Leu Lys
                325                 330                 335

Lys Leu Gln Ser Asn Gly Ala Ile Gln Gly Asp Ser Phe Val Cys Lys
            340                 345                 350

Asn Gly Ala Thr Ser Thr Ser Val Lys Leu Ser Ser Thr Ser Thr Glu
            355                 360                 365

Ser Ser Lys Ser Ser Ala Thr Ser Ser Ala Ser Ser Ser Gly Asp Ala
370                 375                 380

Ser Asn Ala Gln Ala Asn Val Ser Ala Ser Ala Ser Ser Ser Ser Ser
385                 390                 395                 400

Ser Ser Lys Lys Ser Lys Gly Ala Ala Pro Glu Leu Val Pro Ala Thr
            405                 410                 415

Ser Phe Met Gly Val Val Ala Ala Val Gly Val Ala Tyr Tyr Lys Ile
            420                 425                 430

Lys Ala Thr Ile Cys Val Ser Ile Ile Thr Leu Ile Ser Ser Leu Met
            435                 440                 445

Ile Ser Leu Pro Phe Leu Phe Tyr Tyr Glu Thr Val Gly Ser Ser Leu
            450                 455                 460

Asn Phe Ile Cys Arg
465

<210> SEQ ID NO 4
<211> LENGTH: 354
<212> TYPE: PRT
<213> ORGANISM: Yeast
```

```
<400> SEQUENCE: 4

Met Lys Phe Gln Val Val Leu Ser Ala Leu Leu Ala Cys Ser Ser Ala
  1               5                  10                  15

Val Val Ala Ser Pro Ile Glu Asn Leu Phe Lys Tyr Arg Ala Val Lys
             20                  25                  30

Ala Ser His Ser Lys Asn Ile Asn Ser Thr Leu Pro Ala Trp Asn Gly
         35                  40                  45

Ser Asn Ser Ser Asn Val Thr Tyr Ala Asn Gly Thr Asn Ser Thr Thr
     50                  55                  60

Asn Thr Thr Thr Ala Glu Ser Ser Gln Leu Gln Ile Ile Val Thr Gly
 65                  70                  75                  80

Gly Gln Val Pro Ile Thr Asn Ser Ser Leu Thr His Thr Asn Tyr Thr
                 85                  90                  95

Arg Leu Phe Asn Ser Ser Ser Ala Leu Asn Ile Thr Glu Leu Tyr Asn
            100                 105                 110

Val Ala Arg Val Val Asn Glu Thr Ile Gln Asp Lys Ser Ser Ala Gly
            115                 120                 125

Ala Val Val Ala Asn Ala Lys Ser Leu Glu Ala Val Ser Phe Phe
        130                 135                 140

Phe Ser Ile Ile Phe Asp Thr Glu Lys Pro Ile Val Thr Glu Asp
145                 150                 155                 160

Ser Ala Tyr Ala Ile Pro Val Ala Asn Asn Lys Asn Ala Thr Lys Arg
                165                 170                 175

Gly Val Leu Ser Val Thr Ser Asp Lys Leu Val Tyr Ser Gly Val Phe
            180                 185                 190

Thr Pro Pro Thr Ala Cys Ser Tyr Gly Ala Gly Leu Pro Val Ala Ile
            195                 200                 205

Val Asp Asp Gln Asp Glu Val Lys Trp Phe Phe Asp Ala Ser Lys Pro
        210                 215                 220

Thr Leu Ile Ser Ser Asp Ser Ile Ile Arg Lys Glu Tyr Ser Asn Phe
225                 230                 235                 240

Thr Thr Pro Tyr Gly Leu Leu Glu Asn Gly Val Pro Ile Val Pro Ile
                245                 250                 255

Val Tyr Asp Gly Gly Tyr Ser Ser Leu Ile Asp Ser Leu Ser Ser
        260                 265                 270

Ala Val Gln Gly Leu Val Val Ser Ser Gly Ser Thr Asn Ser Thr
        275                 280                 285

Ser Ser Thr Ile Glu Ser Thr Glu Ile Pro Val Val Tyr Ala Gln Ala
    290                 295                 300

Asn Thr Pro Leu Asn Phe Ile Asp Asn Lys Asp Val Pro Lys Asn Ala
305                 310                 315                 320

Val Gly Ala Gly Tyr Leu Ser Pro Ile Lys Ala Gln Ile Leu Leu Ser
                325                 330                 335

Ile Ala Ala Val Asn Gly Val Thr Ser Lys Ser Ala Leu Glu Ser Ile
            340                 345                 350

Phe Pro

<210> SEQ ID NO 5
<211> LENGTH: 396
<212> TYPE: PRT
<213> ORGANISM: Yeast
```

<400> SEQUENCE: 5

```
Met Leu Gln Ser Ile Val Leu Ser Val Cys Met Phe Met Leu His Thr
  1               5                  10                  15

Val Ala Ala Ser Gly Pro Gln Ser Tyr Gln Lys Leu Asp Phe Thr Asn
             20                  25                  30

Val Gly Phe Thr Gly Ser Tyr Val Asp Val Asn Lys Phe Lys Asp Ile
         35                  40                  45

Thr Asn Asn Glu Ser Cys Thr Cys Glu Val Gly Asp Arg Val Trp Phe
     50                  55                  60

Ser Gly Lys Asn Ala Pro Leu Ala Asp Tyr Leu Ser Val His Phe Arg
 65                  70                  75                  80

Gly Pro Leu Lys Leu Lys Gln Phe Ala Phe Tyr Thr Ser Pro Gly Phe
                 85                  90                  95

Thr Val Asn Asn Ser Arg Ser Ser Ser Asp Trp Asn Arg Leu Ala Tyr
            100                 105                 110

Tyr Glu Ser Ser Lys Thr Ala Asp Asn Val Thr Phe Leu Asn His
            115                 120                 125

Gly Gly Glu Ala Ser Pro Cys Leu Gly Asn Ala Leu Ser Tyr Ala Ser
130                 135                 140

Ser Asn Gly Thr Gly Ser Ala Ser Glu Ala Thr Val Leu Ala Asp Gly
145                 150                 155                 160

Thr Leu Ile Ser Ser Asp Gln Glu Tyr Ile Ile Tyr Ser Asn Val Ser
                165                 170                 175

Cys Pro Lys Ser Gly Tyr Asp Lys Gly Cys Gly Val Tyr Arg Ser Gly
            180                 185                 190

Ile Pro Ala Tyr Tyr Gly Tyr Gly Gly Thr Thr Lys Met Phe Leu Phe
            195                 200                 205

Glu Phe Glu Met Pro Thr Glu Thr Glu Lys Asn Ser Ser Ser Ile Gly
            210                 215                 220

Tyr Tyr Asp Leu Pro Ala Ile Trp Leu Leu Asn Asp His Ile Ala Arg
225                 230                 235                 240

Thr Ser Gln Tyr Pro Thr Asn Ala Asn Cys Ser Cys Trp Ala Ser Gly
                245                 250                 255

Cys Gly Glu Tyr Asp Ile Phe Glu Ala Met Asn Gly Thr Glu Lys Asn
            260                 265                 270

His Leu Tyr Ser Thr Phe His Thr Phe Gln Gly Ile Glu Asp Leu Gly
            275                 280                 285

Thr Gly Ile Gln Ser Tyr Gly Tyr Ile Thr Arg Asn Thr Thr Gly Thr
290                 295                 300

Met Lys Gly Gly Val Val Phe Asp Ser Ser Gly Asn Val Val Ser Phe
305                 310                 315                 320

Ile Ser Asp Ala Thr Pro Phe Asn Gly Thr Val Ser Ala Asp Thr Val
                325                 330                 335

Asn Asp Leu Leu Ala Ala Ile Pro Glu Asn Glu Thr Tyr Ser Ser Gln
            340                 345                 350

Leu Met Ser Ile Ser Ala Thr Ala Pro Ser Thr Thr Ser Leu Ser Asn
            355                 360                 365

Gly Val Arg Leu Thr Asn Met Gln Asn Gly Val Trp Tyr Tyr Ile Leu
370                 375                 380

Ala Ile Phe Thr Ala Phe Thr Gln Val Val Leu Ile
385                 390                 395
```

<210> SEQ ID NO 6
<211> LENGTH: 559
<212> TYPE: PRT
<213> ORGANISM: Yeast

<400> SEQUENCE: 6

Met Leu Phe Lys Ser Leu Ser Lys Leu Ala Thr Ala Ala Ala Phe Phe
1               5                   10                  15

Ala Gly Val Ala Thr Ala Asp Asp Val Pro Ala Ile Glu Val Val Gly
            20                  25                  30

Asn Lys Phe Phe Tyr Ser Asn Asn Gly Ser Gln Phe Tyr Ile Arg Gly
        35                  40                  45

Val Ala Tyr Gln Ala Asp Thr Ala Asn Glu Thr Ser Gly Ser Thr Val
    50                  55                  60

Asn Asp Pro Leu Ala Asn Tyr Glu Ser Cys Ser Arg Asp Ile Pro Tyr
65                  70                  75                  80

Leu Lys Lys Leu Asn Thr Asn Val Ile Arg Val Tyr Ala Ile Asn Thr
                85                  90                  95

Thr Leu Asp His Ser Glu Cys Met Lys Ala Leu Asn Asp Ala Asp Ile
            100                 105                 110

Tyr Val Ile Ala Asp Leu Ala Ala Pro Ala Thr Ser Ile Asn Arg Asp
        115                 120                 125

Asp Pro Thr Trp Thr Val Asp Leu Phe Asn Ser Tyr Lys Thr Val Val
130                 135                 140

Asp Thr Phe Ala Asn Tyr Thr Asn Val Leu Gly Phe Ala Gly Asn
145                 150                 155                 160

Glu Val Thr Asn Asn Tyr Thr Asn Thr Asp Ala Ser Ala Phe Val Lys
                165                 170                 175

Ala Ala Ile Arg Asp Val Arg Gln Tyr Ile Ser Asp Lys Asn Tyr Arg
            180                 185                 190

Lys Ile Pro Val Gly Tyr Ser Ser Asn Asp Asp Glu Asp Thr Arg Val
        195                 200                 205

Lys Met Ala Asp Tyr Phe Ala Cys Gly Asp Asp Asp Val Lys Ala Asp
    210                 215                 220

Phe Tyr Gly Ile Asn Met Tyr Glu Trp Cys Gly Lys Ser Asp Phe Lys
225                 230                 235                 240

Thr Ser Gly Tyr Ala Asp Arg Thr Ala Glu Phe Lys Asn Leu Ser Ile
                245                 250                 255

Pro Val Phe Phe Ser Glu Tyr Gly Cys Asn Glu Val Thr Pro Arg Leu
            260                 265                 270

Phe Thr Glu Val Glu Ala Leu Tyr Gly Ser Asn Met Thr Asp Val Trp
        275                 280                 285

Ser Gly Gly Ile Val Tyr Met Tyr Phe Glu Glu Thr Asn Lys Tyr Gly
    290                 295                 300

Leu Val Ser Ile Asp Gly Asn Asp Val Lys Thr Leu Asp Asp Phe Asn
305                 310                 315                 320

Asn Tyr Ser Ser Glu Ile Asn Lys Ile Ser Pro Thr Ser Ala Asn Thr
                325                 330                 335

Lys Ser Tyr Ser Ala Thr Thr Ser Asp Val Ala Cys Pro Ala Thr Gly
            340                 345                 350

Lys Tyr Trp Ser Ala Ala Thr Glu Leu Pro Pro Thr Pro Asn Gly Gly
        355                 360                 365

Leu Cys Ser Cys Met Asn Ala Ala Asn Ser Cys Val Val Ser Asp Asp
    370                 375                 380

```
Val Asp Ser Asp Asp Tyr Glu Thr Leu Phe Asn Trp Ile Cys Asn Glu
385                 390                 395                 400

Val Asp Cys Ser Gly Ile Ser Ala Asn Gly Thr Ala Gly Lys Tyr Gly
            405                 410                 415

Ala Tyr Ser Phe Cys Thr Pro Lys Glu Gln Leu Ser Phe Val Met Asn
        420                 425                 430

Leu Tyr Tyr Glu Lys Ser Gly Gly Ser Lys Ser Asp Cys Ser Phe Ser
    435                 440                 445

Gly Ser Ala Thr Leu Gln Thr Ala Thr Gln Ala Ser Cys Ser Ser
    450                 455                 460

Ala Leu Lys Glu Ile Gly Ser Met Gly Thr Asn Ser Ala Ser Gly Ser
465                 470                 475                 480

Val Asp Leu Gly Ser Gly Thr Glu Ser Ser Thr Ala Ser Ser Asn Ala
            485                 490                 495

Ser Gly Ser Ser Ser Lys Ser Asn Ser Gly Ser Ser Gly Ser Ser Ser
            500                 505                 510

Ser Ser Ser Ser Ser Ser Ala Ser Ser Ser Ser Ser Lys Lys Asn
            515                 520                 525

Ala Ala Thr Asn Val Lys Ala Asn Leu Ala Gln Val Val Phe Thr Ser
530                 535                 540

Ile Ile Ser Leu Ser Ile Ala Ala Gly Val Gly Phe Ala Leu Val
545                 550                 555

<210> SEQ ID NO 7
<211> LENGTH: 484
<212> TYPE: PRT
<213> ORGANISM: Yeast

<400> SEQUENCE: 7

Met Leu Leu Arg Ser Leu Thr Ser Ala Phe Val Leu Ser Ala Gly Leu
1               5                   10                  15

Ala Gln Ala Ala Ser Ser Ser Asn Ser Ser Thr Pro Ser Ile Glu Ile
            20                  25                  30

Lys Gly Asn Ala Phe Phe Asn Ser Glu Ser Gly Glu Arg Phe Tyr Ile
        35                  40                  45

Arg Gly Val Asp Tyr Gln Pro Gly Gly Ser Ser Asn Leu Thr Asp Pro
    50                  55                  60

Leu Ala Asp Ala Ser Val Cys Asp Arg Asp Val Pro Val Leu Lys Asp
65                  70                  75                  80

Leu Gly Ile Asn Thr Val Arg Val Tyr Thr Val Asp Asn Ser Gln Asp
                85                  90                  95

His Ser His Cys Met Lys Leu Leu Gln Glu Asn Gly Ile Tyr Leu Ile
            100                 105                 110

Leu Asp Val Asn Thr Pro Thr Ser Ala Ile Ser Arg Tyr Asp Pro Ala
        115                 120                 125

Cys Ser Tyr Asn Ala Asp Tyr Leu Gln Asn Val Phe Ala Thr Ile Asp
    130                 135                 140

Thr Phe Ala Asp Tyr Asp Asn Val Leu Gly Phe Phe Ala Gly Asn Glu
145                 150                 155                 160

Val Ile Asn Ser Val Asn Thr Thr Asn Thr Ala Thr Tyr Val Lys Ala
                165                 170                 175

Val Val Arg Asp Met Lys Lys Tyr Ile Lys Ala Arg Lys Tyr Arg Gln
            180                 185                 190

Ile Pro Val Gly Tyr Ser Ala Ala Asp Ile Val Ala Asn Arg Gln Leu
        195                 200                 205
```

```
Ala Ala Glu Tyr Phe Asn Cys Gly Asp Glu Ala Asp Ala Arg Ile Asp
        210                 215                 220
Met Phe Gly Val Asn Asp Tyr Ser Trp Cys Gly Glu Ser Ser Phe Val
225                 230                 235                 240
Val Ser Gly Tyr Ser Thr Lys Met Lys Leu Tyr Gln Asp Tyr Ser Val
                245                 250                 255
Pro Val Phe Leu Ser Glu Phe Gly Cys Asn Gln Val Lys Ser Ser Arg
            260                 265                 270
Pro Phe Thr Glu Ile Glu Ala Ile Tyr Ser Thr Gln Met Ser Ser Val
        275                 280                 285
Phe Ser Gly Gly Leu Val Tyr Glu Tyr Ser Asn Glu Thr Asn Asn Tyr
    290                 295                 300
Gly Leu Val Gln Ile Asp Gly Asp Lys Val Thr Lys Leu Thr Asp Phe
305                 310                 315                 320
Glu Asn Leu Lys Asn Glu Tyr Ser Lys Val Ser Asn Pro Glu Gly Asn
                325                 330                 335
Gly Gly Tyr Ser Thr Ser Asn Asn Tyr Ser Thr Cys Pro Asp Tyr Glu
            340                 345                 350
Lys Gly Val Trp Glu Ala Asn Asn Thr Leu Pro Ala Met Pro Ser Ala
        355                 360                 365
Ala Ser Ala Tyr Phe Thr Ser Gly Ala Gly Ser Pro Met Gly Thr Gly
    370                 375                 380
Ile Ala Thr Gln Gln Ser Cys Asp Ala Lys Asp Asp Asp Glu Glu
385                 390                 395                 400
Asp Asp Asp Thr Ser Ser Ser Ser Ser Ser Ser Ser Ser Ser Ser Ser
                405                 410                 415
Ser Ala Ser Ser Ser Ser Glu Ser Ser Ser Thr Ser Lys Ala Ser
            420                 425                 430
Ser Ser Ser Pro Ser Ala Ser Glu Thr Ser Leu Leu Lys Ser Ala Ala
        435                 440                 445
Ser Ala Thr Ser Ser Ser Gln Ser Ser Ser Lys Ser Lys Gly Ala Ala
    450                 455                 460
Gly Ile Ile Glu Ile Pro Leu Ile Phe Arg Ala Leu Ala Glu Leu Tyr
465                 470                 475                 480
Asn Leu Val Leu

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
ctgcagcgag gagccgtaat                                            20

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9 tgatttgat gacgagcgta at                                          22
```

```
<210> SEQ ID NO 10
<211> LENGTH: 17
<212> TYPE: PRT
<213> ORGANISM: Artificial Sequence
<220> FEATURE:
<223> OTHER INFORMATION: Synthetic construct

<400> SEQUENCE: 10

Cys Asp Ser Leu Glu Ser Ile Thr Asp Ser Leu Asn Leu Gln Ser Leu
1               5                   10                  15

Thr

<210> SEQ ID NO 11
<211> LENGTH: 15
<212> TYPE: PRT
<213> ORGANISM: Artificial Sequence
<220> FEATURE:
<223> OTHER INFORMATION: Synthetic construct

<400> SEQUENCE: 11

Cys Asp Ser Ile Lys Lys Ile Thr Gly Asp Leu Asn Met Gln Glu
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Synthetic construct

<400> SEQUENCE: 12

Cys Ala Val Asn Gly Val Thr Ser Lys Ser Ala Leu Glu Ser Ile Phe
1               5                   10                  15

Pro

<210> SEQ ID NO 13
<211> LENGTH: 24
<212> TYPE: PRT
<213> ORGANISM: Artificial Sequence
<220> FEATURE:
<223> OTHER INFORMATION: Synthetic construct

<400> SEQUENCE: 13

Cys Thr Pro Lys Glu Gln Leu Ser Phe Val Met Asn Leu Tyr Tyr Glu
1               5                   10                  15

Lys Ser Gly Gly Ser Lys Ser Asp
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic construct

<400> SEQUENCE: 14

Cys Pro Ala Thr Gly Lys Tyr Trp Ser Ala Ala Thr Glu Leu Pro Pro
1               5                   10                  15

Thr Pro Asn Gly
            20

<210> SEQ ID NO 15
<211> LENGTH: 29
<212> TYPE: PRT
<213> ORGANISM: Artificial Sequence
```

```
<220> FEATURE:
<223> OTHER INFORMATION: Synthetic construct

<400> SEQUENCE: 15

Cys Pro Ala Met Pro Ser Ala Ala Ser Ala Tyr Phe Thr Ser Gly Ala
1               5                   10                  15

Gly Ser Pro Met Gly Thr Gly Ile Ala Thr Gln Gln Ser
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic construct

<400> SEQUENCE: 16

Cys Glu Ile Lys Gly Asn Ala Phe Phe Asn Ser Glu Ser Gly Glu Arg
1               5                   10                  15

Phe Tyr Ile Arg Gly Val Asp Tyr Gln Pro Gly Gly Ser
            20                  25

<210> SEQ ID NO 17
<211> LENGTH: 20
<212> TYPE: PRT
<213> ORGANISM: Artificial Sequence
<220> FEATURE:
<223> OTHER INFORMATION: Synthetic construct

<400> SEQUENCE: 17

Cys Ser Gly Pro Gln Ser Tyr Gln Lys Leu Asp Phe Thr Asn Val Gly
1               5                   10                  15

Phe Thr Gly Ser
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic construct

<400> SEQUENCE: 18

Cys Glu Val Gly Asp Arg Val Trp Phe Ser Gly Lys Asn Ala Pro Leu
1               5                   10                  15

Ala Asp Tyr

<210> SEQ ID NO 19
<211> LENGTH: 17
<212> TYPE: PRT
<213> ORGANISM: Artificial Sequence
<220> FEATURE:
<223> OTHER INFORMATION: Synthetic construct

<400> SEQUENCE: 19

Cys Glu Gln Met His Glu Asp Ile Ile Ser Leu Trp Asp Gln Ser Leu
1               5                   10                  15

Lys

<210> SEQ ID NO 20
<211> LENGTH: 31
<212> TYPE: DNA
<213> ORGANISM: Artificial Sequence
<220> FEATURE:
<223> OTHER INFORMATION: Synthetic construct
```

-continued

```
<400> SEQUENCE: 20
atggtaccaa agaatgagat ttccttcaat t                                    31

<210> SEQ ID NO 21
<211> LENGTH: 29
<212> TYPE: DNA
<213> ORGANISM: Artificial Sequence
<220> FEATURE:
<223> OTHER INFORMATION: Synthetic construct

<400> SEQUENCE: 21
atggatccag cttcagcctc tcttttatc                                      29

<210> SEQ ID NO 22
<211> LENGTH: 28
<212> TYPE: DNA
<213> ORGANISM: Artificial Sequence
<220> FEATURE:
<223> OTHER INFORMATION: Synthetic construct

<400> SEQUENCE: 22
tggaattctg tgggtgactg tatactat                                       28

<210> SEQ ID NO 23
<211> LENGTH: 29
<212> TYPE: DNA
<213> ORGANISM: Artificial Sequence
<220> FEATURE:
<223> OTHER INFORMATION: Synthetic construct

<400> SEQUENCE: 23
tatctagacc ccacagcgcg cttctccct                                      29

<210> SEQ ID NO 24
<211> LENGTH: 31
<212> TYPE: DNA
<213> ORGANISM: Artificial Sequence
<220> FEATURE:
<223> OTHER INFORMATION: Synthetic construct

<400> SEQUENCE: 24
tggaattctg ttgtgggtca cagtctatta t                                    31

<210> SEQ ID NO 25
<211> LENGTH: 29
<212> TYPE: DNA
<213> ORGANISM: Artificial Sequence
<220> FEATURE:
<223> OTHER INFORMATION: Synthetic construct

<400> SEQUENCE: 25
attctagatt ctctttgcac cactcttct                                      29
```